US009303254B2

(12) United States Patent
Power et al.

(10) Patent No.: US 9,303,254 B2
(45) Date of Patent: Apr. 5, 2016

(54) CHIMERIC ALPHA-AMYLASE VARIANTS

(71) Applicant: Danisco US Inc., Palo Alto, CA (US)

(72) Inventors: Scott D. Power, San Bruno, CA (US); Andrew Shaw, San Francisco, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 14/038,405

(22) Filed: Sep. 26, 2013

(65) Prior Publication Data

US 2014/0106409 A1  Apr. 17, 2014

Related U.S. Application Data

(62) Division of application No. 12/990,201, filed as application No. PCT/US2009/041498 on Apr. 23, 2009, now abandoned.

(60) Provisional application No. 61/126,066, filed on Apr. 30, 2008.

(51) Int. Cl.
| C12N 9/28 | (2006.01) |
| C12N 9/96 | (2006.01) |
| C12P 19/14 | (2006.01) |
| A23L 1/03 | (2006.01) |
| C11D 3/386 | (2006.01) |

(52) U.S. Cl.
CPC . *C12N 9/96* (2013.01); *A23L 1/034* (2013.01); *C11D 3/38618* (2013.01); *C12N 9/2417* (2013.01); *C12P 19/14* (2013.01); *Y02E 50/17* (2013.01)

(58) Field of Classification Search
None
See application file for complete search history.

(56) References Cited

U.S. PATENT DOCUMENTS

| 4,435,307 | A | | 3/1984 | Barbesgaard et al. |
| RE32,153 | E | | 5/1986 | Tamura et al. |
| 4,587,215 | A | | 5/1986 | Hirsh |
| 5,234,823 | A | * | 8/1993 | Diderichsen et al. ........... 435/99 |
| 5,427,936 | A | | 6/1995 | Moeller et al. |
| 5,457,046 | A | | 10/1995 | Wöldike et al. |
| 5,648,263 | A | | 7/1997 | Schülein et al. |
| 5,686,593 | A | | 11/1997 | Wöldike et al. |
| 5,691,178 | A | | 11/1997 | Schülein et al. |
| 5,736,499 | A | | 4/1998 | Mitchinson et al. |
| 5,763,254 | A | | 6/1998 | Wöldike et al. |
| 5,776,757 | A | | 7/1998 | Schülein et al. |
| 5,830,837 | A | | 11/1998 | Bisg.ang.rd-Frantzen et al. |
| 6,143,708 | A | | 11/2000 | Svendsen et al. |
| 6,187,576 | B1 | | 2/2001 | Svendsen et al. |
| 6,287,841 | B1 | | 9/2001 | Mulleners et al. |
| 6,939,703 | B2 | | 9/2005 | Van Der Laan et al. |
| 7,163,816 | B2 | | 1/2007 | Svendsen et al. |
| 2003/0021795 | A1 | | 1/2003 | Houston |

FOREIGN PATENT DOCUMENTS

| CA | 2202553 A1 | 4/1996 |
| EP | 0 218 272 A1 | 4/1987 |
| EP | 0 238 023 A2 | 9/1987 |
| EP | 0 305 216 A1 | 3/1989 |
| EP | 0 407 225 A1 | 1/1991 |
| EP | 0 495 257 A1 | 7/1992 |
| EP | 0 260 105 A2 | 5/1994 |
| EP | 0 258 068 A2 | 8/1994 |
| EP | 0 531 372 B1 | 2/1995 |
| EP | 0 721 981 A1 | 7/1996 |
| EP | 0 214 761 A2 | 3/1997 |
| EP | 0 531 315 B1 | 3/1997 |
| EP | 0 331 376 A2 | 10/1997 |
| EP | 0 812 910 A1 | 12/1997 |
| GB | 1372034 A | 10/1974 |
| IE | 1991/1797 A1 | 12/1990 |
| WO | WO 84/02921 A2 | 8/1984 |
| WO | WO 86/01831 A1 | 3/1986 |
| WO | WO 88/02775 A1 | 4/1988 |
| WO | WO 89/01032 A2 | 2/1989 |
| WO | WO 89/06270 A1 | 7/1989 |
| WO | WO 89/06279 A1 | 7/1989 |
| WO | WO 89/09259 A1 | 10/1989 |
| WO | WO 91/19782 A1 | 12/1991 |
| WO | WO 92/00381 A1 | 1/1992 |
| WO | WO 92/01793 A1 | 2/1992 |
| WO | WO 92/05249 A1 | 4/1992 |
| WO | WO 92/17573 A1 | 10/1992 |
| WO | WO 92/19729 A1 | 11/1992 |
| WO | WO 93/24618 A1 | 12/1993 |

(Continued)

OTHER PUBLICATIONS

Aurora, R., et al., "Helix capping."*Protein Science*, 7(1): 21-38, (1998).
Boel, E., et al. "Glucoamylases GI and G2 from *Aspergillus niger* are synthesized from two different but closely related mRNAs." *EMBO J*. 3(5): 1097-1102, (1984).
Chen, H.-M., et al. "Substitution of asparagine residues in Aspergillus awamori glucoamylase by site-directed mutagenesis to eliminate N-glycosylation and inactivation by deamidation." *Biochem. J.* 301: 275-281, (1994).
Chen, H.-M., et al., "Effect of replacing helical glycine residues with alanines on reversible and irreversible stability and production of Aspergillus awamori glucoamylase." *Prot. Eng.* 9(6): 499-505, (1996).
Chen, H.-M., et al., "Identification and elimination by site-directed mutagenesis of thermolabile aspartyl bonds in Aspergillus awamori glucoamylase." *Prot. Eng.* 8(6): 575-582, (1995).

(Continued)

*Primary Examiner* — Richard Hutson
(74) *Attorney, Agent, or Firm* — Danisco US Inc.

(57) ABSTRACT

Chimeric alpha-amylases having the characteristics of high thermostability and good performance in starch degradation, especially high-temperature liquefaction processes, are provided. The alpha-amylases are chimeras of AmyL and AmyS enzymes, and are useful in starch degradation processes. Methods of making the chimeric enzymes, and methods of using the chimeric alpha-amylases for liquefaction, cleaning starch residue from a surface, and treating woven material to remove coatings. Kits for practicing the methods are provided. Polynucleotides encoding the chimeric amylases, vectors, and expression hosts also are provided.

26 Claims, 18 Drawing Sheets

(56) References Cited

FOREIGN PATENT DOCUMENTS

| | | |
|---|---|---|
| WO | WO 94/01541 A1 | 1/1994 |
| WO | WO 94/07998 A1 | 4/1994 |
| WO | WO 94/25578 A1 | 11/1994 |
| WO | WO 94/25583 A1 | 11/1994 |
| WO | WO 95/10602 A1 | 4/1995 |
| WO | WO 95/14783 A1 | 6/1995 |
| WO | WO 95/22615 A1 | 8/1995 |
| WO | WO 95/24471 A1 | 9/1995 |
| WO | WO 95/30744 A2 | 11/1995 |
| WO | WO 95/35381 A1 | 12/1995 |
| WO | WO 96/00292 A1 | 1/1996 |
| WO | WO 96/11262 A1 | 4/1996 |
| WO | WO 96/13580 A1 | 5/1996 |
| WO | WO 96/23874 | 8/1996 |
| WO | WO 96/29397 A1 | 9/1996 |
| WO | WO 96/34108 A2 | 10/1996 |
| WO | WO 96/39528 | 12/1996 |
| WO | WO 97/04079 A1 | 2/1997 |
| WO | WO 97/07202 A1 | 2/1997 |
| WO | WO 98/08940 A1 | 3/1998 |
| WO | WO 98/12307 A1 | 3/1998 |
| WO | WO 98/15257 A1 | 4/1998 |
| WO | WO 98/20115 A1 | 5/1998 |
| WO | WO 98/22613 A1 | 5/1998 |
| WO | WO 99/01544 A1 | 1/1999 |
| WO | WO 99/25846 A2 | 5/1999 |
| WO | WO 99/28448 A1 | 6/1999 |
| WO | WO 00/04136 A1 | 1/2000 |
| WO | WO 01/14629 A2 | 3/2001 |
| WO | WO 01/34899 A1 | 5/2001 |
| WO | WO 01/96368 | 12/2001 |
| WO | WO 02/02776 | 3/2002 |
| WO | WO 2005/111203 A2 | 11/2005 |
| WO | WO 2007/079938 | 7/2007 |

OTHER PUBLICATIONS

Christophersen, C., et al., "Enzymatic Characterisation of Novamyl®, a Thermostable α-Amylase." *Starch* 50:39-45, (1999).

Dartois, V. et al., "Cloning, nucleotide sequence and expression in *Escherichia coli* of a lipase gene from Bacillus subtilis 168." *Biochemica Biophysica Acta* 1131: 253-360, (1992).

Ferrari, F.A., et al., "Construction and Properties of an Integrable Plasmid for Bacillus subtilis." *J. Bacteriology*, 154:1513-1515, (1983).

Fierobe, H.-P., et al. "Mutational Modulation of Substrate Bond-Type Specificity and Thermostability of Glucoamylase from Aspergillus awamori by Replacement with Short Homologue Active Site Sequences and Thiol/Disulfide Engineering." *Biochemistry*, 35: 8698-8704, (1996).

Fogarty, W.M. et al., "Starch-Degrading Enzymes of Microbial Origin." In *Progress in Industrial Microbiology*, vol. 15, pp. 112-115, (1979).

Igarashi, K., et al., "Improved Thermostability of a *Bacillus* α-Amylase by Deletion of an Arginine-Glycine Residue Is Caused by Enhanced Calcium Binding." *Biochem. Biophys. Res. Comm.* 248: 372-377, (1998).

International Search Report and the Written Opinion of the International Searching Authority of International Application No. PCT/US2009/041498.

Jensen, C.L., et al., "Cell-associated degradation affect the yield of secreted engineered and heterologous proteins in the Bacillus subtilis expression system." *Microbiology* 146(1): 2583-2594, (2000).

Jorgensen, P.L., et al., "In vivo genetic engineering: homologous recombination as a tool for plasmid reconstruction." *Gene* 96: 37-41, (1990).

Li, Y., et al., "Effect of introducing proline residues on the stability of Aspergillus awamori." *Protein Eng.* 10(10): 1199-1204, (1997).

Presta, L.G., et al., "Helix signals in proteins." *Science* 240: 1632-1641, (1988).

Sajedi, R.H., et al., "Nucleotide Sequence, Structural Investigation and Homology Modeling Studies of a Ca2+-independent α-amylase with Acidic pH-profile" *J. Biochem. Mol. Biol.* 40: 315-324, (2006).

Semimaru, T., et al., "Functional Analysis of the Threonine- and Serine-Rich Gp-I Domain of Glucoamylase I from *Aspergillus awamori* var. *kawachi*." *Agric. Biol. Chemo* 55(4): 941-949, (1991), Mar. 4, 2015.

Shiau, R.J., et al. "Improving the Thermostability of Raw-Starch-Digesting Amylase from a *Cytophaga* sp. By Site-Directed Mutagenesis." *Appl. Environ. Micro.* 69:2383, (2003).

Suzuki, Y., et al. "Amino Acid Residues Stabilizing a Bacillus a-Amylase against Irreversible Thermoinactivation." *J. Biol. Chem.* 264:18933-18938, (1989).

* cited by examiner

Sequence ID "1"     *B. licheniformis* AmyL

```
  1  TNLNGTLMQY FEWYTPNDGQ HWKRLQNDSA YLAEHGITAV WIPPAYKGTS
 51  QADVGYGAYD LYDLGEFHQK GTVRTKYGTK GELQSAIKSL HSRDINVYGD
101  VVINHKGGAD ATEDVTAVEV DPADRNRVIS GEYLIKAWTH FHFPGRGSTY
151  SDFKWHWYHF DGTDWDESRK LNRIYKFQGK AWDWEVSSEN GNYDYLMYAD
201  IDYDHPDVVA EIKRWGTWYA NELQLDGFRL DAVKHIKFSF LRDWVNHVRE
251  KTGKEMFTVA EYWQNDLGAL ENYLNKTNFN HSVFDVPLHY QFHAASTQGG
301  GYDMRKLLNG TVVSKHPLKS VTFVDNHDTQ PGQSLESTVQ TWFKPLAYAF
351  ILTRESGYPQ VFYGDMYGTK GDSQREIPAL KHKIEPILKA RKQYAYGAQH
401  DYFDHHDIVG WTREGDSSVA NSGLAALITD GPGGAKRMYV GRQNAGETWH
451  DITGNRSEPV VINSEGWGEF HVNGGSVSIY VQR
```

Sequence ID "2"     *B. stearothermophilus* AmyS

```
  1  AAPFNGTMMQ YFEWYLPDDG TLWTKVANEA NNLSSLGITA LWLPPAYKGT
 51  SRSDVGYGVY DLYDLGEFNQ KGTVRTKYGT KAQYLQAIQA AHAAGMQVYA
101  DVVFDHKGGA DGTEWVDAVE VNPSDRNQEI SGTYQIQAWT KFDFPGRGNT
151  YSSFKWRWYH FDGVDWDESR KLSRIYKFRG IGKAWDWEVD TENGNYDYLM
201  YADLDMDHPE VVTELKNWGK WYVNTTNIDG FRLDAVKHIK FSFFPDWLSY
251  VRSQTGKPLF TVGEYWSYDI NKLHNYITKT NGTMSLFDAP LHNKFYTASK
301  SGGAFDMRTL MTNTLMKDQP TLAVTFVDNH DTEPGQALQS WVDPWFKPLA
351  YAFILTRQEG YPCVFYGDYY GIPQYNIPSL KSKIDPLLIA RRDYAYGTQH
401  DYLDHSDIIG WTREGVTEKP GSGLAALITD GPGGSKWMYV GKQHAGKVFY
451  DLTGNRSDTV TINSDGWGEF KVNGGSVSVW VPRKTT
```

Sequence ID "3"     "AmyS control." Note that this protein is the mature form of a translation product that has been naturally processed to trim off the last 29 aa for the C-terminus. The precursor is encoded by SEQ ID NO: 20.

```
  1  AAPFNGTMMQ YFEWYLPDDG TLWTKVANEA NNLSSLGITA LWLPPAYKGT
 51  SRSDVGYGVY DLYDLGEFNQ KGTVRTKYGT KAQYLQAIQA AHAAGMQVYA
101  DVVFDHKGGA DGTEWVDAVE VNPSDRNQEI SGTYQIQAWT KFDFPGRGNT
151  YSSFKWRWYH FDGVDWDESR KLSRIYKFIG KAWDWEVDTE NGNYDYLMYA
201  DLDMDHPEVV TELKNWGKWY VNTTNIDGFR LDAVKHIKFS FFPDWLSYVR
251  SQTGKPLFTV GEYWSYDINK LHNYITKTNG TMSLFDAPLH NKFYTASKSG
301  GAFDMRTLMT NTLMKDQPTL AVTFVDNHDT EPGQALQSWV DPWFKPLAYA
351  FILTRQEGYP CVFYGDYYGI PQYNIPSLKS KIDPLLIARR DYAYGTQHDY
401  LDHSDIIGWT REGVTEKPGS GLAALITDGP GGSKWMYVGK QHAGKVFYDL
451  TGNRSDTVTI NSDGWGEFKV NGGSVSVWVP RKTT
```

FIG. 7A

Sequence ID "4"      186

```
  1   TNLNGTLMQY FEWYTPNDGQ HWKRLQNDSA YLAEHGITAV WIPPAYKGTS
 51   QADVGYGAYD LYDLGEFHQK GTVRTKYGTK GELQSAIKSL HSRDINVYGD
101   VVINHKGGAD ATEDVTAVEV DPADRNRVIS GEYLIKAWTH FHFPGRGSTY
151   SDFKWHWYHF DGTDWDESRK LNRIYKFQGK AWDWEVDTEN GNYDYLMYAD
201   LDMDHPEVVT ELKNWGKWYV NTTNIDGFRL DAVKHIKFSF FPDWLSYVRS
251   QTGKPLFTVG EYWSYDINKL HNYITKTNGT MSLFDAPLHN KFYTASKSGG
301   AFDMRTLMTN TLMKDQPTLA VTFVDNHDTE PGQALQSWVD PWFKPLAYAF
351   ILTRQEGYPC VFYGDYYGIP QYNIPSLKSK IDPLLIARRD YAYGTQHDYL
401   DHSDIIGWTR EGVTEKPGSG LAALITDGPG GSKWMYVGKQ HAGKVFYDLT
451   GNRSDTVTIN SDGWGEFKVN GGSVSVWVPR KTT
```

Sequence ID "5"      187

```
  1   TNLNGTLMQY FEWYTPNDGQ HWKRLQNDSA YLAEHGITAV WIPPAYKGTS
 51   QADVGYGAYD LYDLGEFHQK GTVRTKYGTK GELQSAIKSL HSRDINVYGD
101   VVINHKGGAD ATEDVTAVEV DPADRNRVIS GEYLIKAWTH FHFPGRGSTY
151   SDFKWHWYHF DGTDWDESRK LNRIYKFQGK AWDWEVSTEN GNYDYLMYAD
201   LDMDHPEVVT ELKNWGKWYV NTTNIDGFRL DAVKHIKFSF FPDWLSYVRS
251   QTGKPLFTVG EYWSYDINKL HNYITKTNGT MSLFDAPLHN KFYTASKSGG
301   AFDMRTLMTN TLMKDQPTLA VTFVDNHDTE PGQALQSWVD PWFKPLAYAF
351   ILTRQEGYPC VFYGDYYGIP QYNIPSLKSK IDPLLIARRD YAYGTQHDYL
401   DHSDIIGWTR EGVTEKPGSG LAALITDGPG GSKWMYVGKQ HAGKVFYDLT
451   GNRSDTVTIN SDGWGEFKVN GGSVSVWVPR KTT
```

Sequence ID "6"      200

```
  1   TNLNGTLMQY FEWYTPNDGQ HWKRLQNDSA YLAEHGITAV WIPPAYKGTS
 51   QADVGYGAYD LYDLGEFHQK GTVRTKYGTK GELQSAIKSL HSRDINVYGD
101   VVINHKGGAD ATEDVTAVEV DPADRNRVIS GEYLIKAWTH FHFPGRGSTY
151   SDFKWHWYHF DGTDWDESRK LNRIYKFQGK AWDWEVSSEN GNYDYLMYAD
201   LDMDHPEVVT ELKNWGKWYV NTTNIDGFRL DAVKHIKFSF FPDWLSYVRS
251   QTGKPLFTVG EYWSYDINKL HNYITKTNGT MSLFDAPLHN KFYTASKSGG
301   AFDMRTLMTN TLMKDQPTLA VTFVDNHDTE PGQALQSWVD PWFKPLAYAF
351   ILTRQEGYPC VFYGDYYGIP QYNIPSLKSK IDPLLIARRD YAYGTQHDYL
401   DHSDIIGWTR EGVTEKPGSG LAALITDGPG GSKWMYVGKQ HAGKVFYDLT
451   GNRSDTVTIN SDGWGEFKVN GGSVSVWVPR KTT
```

Sequence ID "7"      200SB

```
  1   TNLNGTLMQY FEWYTPNDGQ HWKRLQNDSA YLAEHGITAV WIPPAYKGTS
 51   QADVGYGAYD LYDLGEFHQK GTVRTKYGTK GELQSAIKSL HSRDINVYGD
101   VVINHKGGAD ATEDVTAVEV DPADRNRVIS GEYLIKAWTH FHFPGRGSTY
151   SDFKWHWYHF DGTDWDESRK LNRIYKFQGK AWDWEVDTEN GNYDYLMYAD
201   LDMDHPEVVT ELKNWGKWYV NTTNIDGFRL DAVKHIKFSF FPDWLSYVRS
251   QTGKPLFTVG EYWSYDINKL HNYITKTNGT MSLFDAPLHN KFYTASKSGG
301   AFDMRTLMTN TLMKDQPTLA VTFVDNHDTE PGQALQSWVD PWFKPLAYAF
351   ILTRQEGYPC VFYGDYYGIP QYNIPSLKSK IDPLLIARRD YAYGTQHDYL
401   DHSDIIGWTR EGVTEKPGSG LAALITDGPG GSKWMYVGKQ HAGKVFYDLT
451   GNRSDTVTIN SDGWGEFKVN GGSVSVWVPR KTT
```

*FIG. 7B*

Sequence ID "8"      202
```
  1    TNLNGTLMQY FEWYTPNDGQ HWKRLQNDSA YLAEHGITAV WIPPAYKGTS
 51    QADVGYGAYD LYDLGEFHQK GTVRTKYGTK GELQSAIKSL HSRDINVYGD
101    VVINHKGGAD ATEDVTAVEV DPADRNRVIS GEYLIKAWTH FHFPGRGSTY
151    SDFKWHWYHF DGTDWDESRK LNRIYKFQGK AWDWEVSSEN GNYDYLMYAD
201    IDMDHPEVVT ELKNWGKWYV NTTNIDGFRL DAVKHIKFSF FPDWLSYVRS
251    QTGKPLFTVG EYWSYDINKL HNYITKTNGT MSLFDAPLHN KFYTASKSGG
301    AFDMRTLMTN TLMKDQPTLA VTFVDNHDTE PGQALQSWVD PWFKPLAYAF
351    ILTRQEGYPC VFYGDYYGIP QYNIPSLKSK IDPLLIARRD YAYGTQHDYL
401    DHSDIIGWTR EGVTEKPGSG LAALITDGPG GSKWMYVGKQ HAGKVFYDLT
451    GNRSDTVTIN SDGWGEFKVN GGSVSVWVPR KTT
```

Sequence ID "9"      202SB
```
  1    TNLNGTLMQY FEWYTPNDGQ HWKRLQNDSA YLAEHGITAV WIPPAYKGTS
 51    QADVGYGAYD LYDLGEFHQK GTVRTKYGTK GELQSAIKSL HSRDINVYGD
101    VVINHKGGAD ATEDVTAVEV DPADRNRVIS GEYLIKAWTH FHFPGRGSTY
151    SDFKWHWYHF DGTDWDESRK LNRIYKFQGK AWDWEVDTEN GNYDYLMYAD
201    IDMDHPEVVT ELKNWGKWYV NTTNIDGFRL DAVKHIKFSF FPDWLSYVRS
251    QTGKPLFTVG EYWSYDINKL HNYITKTNGT MSLFDAPLHN KFYTASKSGG
301    AFDMRTLMTN TLMKDQPTLA VTFVDNHDTE PGQALQSWVD PWFKPLAYAF
351    ILTRQEGYPC VFYGDYYGIP QYNIPSLKSK IDPLLIARRD YAYGTQHDYL
401    DHSDIIGWTR EGVTEKPGSG LAALITDGPG GSKWMYVGKQ HAGKVFYDLT
451    GNRSDTVTIN SDGWGEFKVN GGSVSVWVPR KTT
```

Sequence ID "10"     228
```
  1    TNLNGTLMQY FEWYTPNDGQ HWKRLQNDSA YLAEHGITAV WIPPAYKGTS
 51    QADVGYGAYD LYDLGEFHQK GTVRTKYGTK GELQSAIKSL HSRDINVYGD
101    VVINHKGGAD ATEDVTAVEV DPADRNRVIS GEYLIKAWTH FHFPGRGSTY
151    SDFKWHWYHF DGTDWDESRK LNRIYKFQGK AWDWEVSSEN GNYDYLMYAD
201    IDYDHPDVVA EIKRWGTWYA NELQLDGFRL DAVKHIKFSF FPDWLSYVRS
251    QTGKPLFTVG EYWSYDINKL HNYITKTNGT MSLFDAPLHN KFYTASKSGG
301    AFDMRTLMTN TLMKDQPTLA VTFVDNHDTE PGQALQSWVD PWFKPLAYAF
351    ILTRQEGYPC VFYGDYYGIP QYNIPSLKSK IDPLLIARRD YAYGTQHDYL
401    DHSDIIGWTR EGVTEKPGSG LAALITDGPG GSKWMYVGKQ HAGKVFYDLT
451    GNRSDTVTIN SDGWGEFKVN GGSVSVWVPR KTT
```

Sequence ID "11"     228SB
```
  1    TNLNGTLMQY FEWYTPNDGQ HWKRLQNDSA YLAEHGITAV WIPPAYKGTS
 51    QADVGYGAYD LYDLGEFHQK GTVRTKYGTK GELQSAIKSL HSRDINVYGD
101    VVINHKGGAD ATEDVTAVEV DPADRNRVIS GEYLIKAWTH FHFPGRGSTY
151    SDFKWHWYHF DGTDWDESRK LNRIYKFQGK AWDWEVDTEN GNYDYLMYAD
201    IDYDHPDVVA EIKRWGTWYA NELQLDGFRL DAVKHIKFSF FPDWLSYVRS
251    QTGKPLFTVG EYWSYDINKL HNYITKTNGT MSLFDAPLHN KFYTASKSGG
301    AFDMRTLMTN TLMKDQPTLA VTFVDNHDTE PGQALQSWVD PWFKPLAYAF
351    ILTRQEGYPC VFYGDYYGIP QYNIPSLKSK IDPLLIARRD YAYGTQHDYL
401    DHSDIIGWTR EGVTEKPGSG LAALITDGPG GSKWMYVGKQ HAGKVFYDLT
451    GNRSDTVTIN SDGWGEFKVN GGSVSVWVPR KTT
```

*FIG. 7C*

Sequence ID "12"    249

```
  1   TNLNGTLMQY FEWYTPNDGQ HWKRLQNDSA YLAEHGITAV WIPPAYKGTS
 51   QADVGYGAYD LYDLGEFHQK GTVRTKYGTK GELQSAIKSL HSRDINVYGD
101   VVINHKGGAD ATEDVTAVEV DPADRNRVIS GEYLIKAWTH FHFPGRGSTY
151   SDFKWHWYHF DGTDWDESRK LNRIYKFQGK AWDWEVSSEN GNYDYLMYAD
201   IDYDHPDVVA EIKRWGTWYA NELQLDGFRL DAVKHIKFSF LRDWVNHVRS
251   QTGKPLFTVG EYWSYDINKL HNYITKTNGT MSLFDAPLHN KFYTASKSGG
301   AFDMRTLMTN TLMKDQPTLA VTFVDNHDTE PGQALQSWVD PWFKPLAYAF
351   ILTRQEGYPC VFYGDYYGIP QYNIPSLKSK IDPLLIARRD YAYGTQHDYL
401   DHSDIIGWTR EGVTEKPGSG LAALITDGPG GSKWMYVGKQ HAGKVFYDLT
451   GNRSDTVTIN SDGWGEFKVN GGSVSVWVPR KTT
```

Sequence ID "13"    249SB

```
  1   TNLNGTLMQY FEWYTPNDGQ HWKRLQNDSA YLAEHGITAV WIPPAYKGTS
 51   QADVGYGAYD LYDLGEFHQK GTVRTKYGTK GELQSAIKSL HSRDINVYGD
101   VVINHKGGAD ATEDVTAVEV DPADRNRVIS GEYLIKAWTH FHFPGRGSTY
151   SDFKWHWYHF DGTDWDESRK LNRIYKFQGK AWDWEVDTEN GNYDYLMYAD
201   IDYDHPDVVA EIKRWGTWYA NELQLDGFRL DAVKHIKFSF LRDWVNHVRS
251   QTGKPLFTVG EYWSYDINKL HNYITKTNGT MSLFDAPLHN KFYTASKSGG
301   AFDMRTLMTN TLMKDQPTLA VTFVDNHDTE PGQALQSWVD PWFKPLAYAF
351   ILTRQEGYPC VFYGDYYGIP QYNIPSLKSK IDPLLIARRD YAYGTQHDYL
401   DHSDIIGWTR EGVTEKPGSG LAALITDGPG GSKWMYVGKQ HAGKVFYDLT
451   GNRSDTVTIN SDGWGEFKVN GGSVSVWVPR KTT
```

Sequence ID "14"    254

```
  1   TNLNGTLMQY FEWYTPNDGQ HWKRLQNDSA YLAEHGITAV WIPPAYKGTS
 51   QADVGYGAYD LYDLGEFHQK GTVRTKYGTK GELQSAIKSL HSRDINVYGD
101   VVINHKGGAD ATEDVTAVEV DPADRNRVIS GEYLIKAWTH FHFPGRGSTY
151   SDFKWHWYHF DGTDWDESRK LNRIYKFQGK AWDWEVSSEN GNYDYLMYAD
201   IDYDHPDVVA EIKRWGTWYA NELQLDGFRL DAVKHIKFSF LRDWVNHVRE
251   KTGKPLFTVG EYWSYDINKL HNYITKTNGT MSLFDAPLHN KFYTASKSGG
301   AFDMRTLMTN TLMKDQPTLA VTFVDNHDTE PGQALQSWVD PWFKPLAYAF
351   ILTRQEGYPC VFYGDYYGIP QYNIPSLKSK IDPLLIARRD YAYGTQHDYL
401   DHSDIIGWTR EGVTEKPGSG LAALITDGPG GSKWMYVGKQ HAGKVFYDLT
451   GNRSDTVTIN SDGWGEFKVN GGSVSVWVPR KTT
```

Sequence ID "15"    254SB

```
  1   TNLNGTLMQY FEWYTPNDGQ HWKRLQNDSA YLAEHGITAV WIPPAYKGTS
 51   QADVGYGAYD LYDLGEFHQK GTVRTKYGTK GELQSAIKSL HSRDINVYGD
101   VVINHKGGAD ATEDVTAVEV DPADRNRVIS GEYLIKAWTH FHFPGRGSTY
151   SDFKWHWYHF DGTDWDESRK LNRIYKFQGK AWDWEVDTEN GNYDYLMYAD
201   IDYDHPDVVA EIKRWGTWYA NELQLDGFRL DAVKHIKFSF LRDWVNHVRE
251   KTGKPLFTVG EYWSYDINKL HNYITKTNGT MSLFDAPLHN KFYTASKSGG
301   AFDMRTLMTN TLMKDQPTLA VTFVDNHDTE PGQALQSWVD PWFKPLAYAF
351   ILTRQEGYPC VFYGDYYGIP QYNIPSLKSK IDPLLIARRD YAYGTQHDYL
401   DHSDIIGWTR EGVTEKPGSG LAALITDGPG GSKWMYVGKQ HAGKVFYDLT
451   GNRSDTVTIN SDGWGEFKVN GGSVSVWVPR KTT
```

*FIG. 7D*

Sequence ID "16"    259
  1 TNLNGTLMQY FEWYTPNDGQ HWKRLQNDSA YLAEHGITAV WIPPAYKGTS
 51 QADVGYGAYD LYDLGEFHQK GTVRTKYGTK GELQSAIKSL HSRDINVYGD
101 VVINHKGGAD ATEDVTAVEV DPADRNRVIS GEYLIKAWTH FHFPGRGSTY
151 SDFKWHWYHF DGTDWDESRK LNRIYKFQGK AWDWEVSSEN GNYDYLMYAD
201 IDYDHPDVVA EIKRWGTWYA NELQLDGFRL DAVKHIKFSF LRDWVNHVRE
251 KTGKEMFTVG EYWSYDINKL HNYITKTNGT MSLFDAPLHN KFYTASKSGG
301 AFDMRTLMTN TLMKDQPTLA VTFVDNHDTE PGQALQSWVD PWFKPLAYAF
351 ILTRQEGYPC VFYGDYYGIP QYNIPSLKSK IDPLLIARRD YAYGTQHDYL
401 DHSDIIGWTR EGVTEKPGSG LAALITDGPG GSKWMYVGKQ HAGKVFYDLT
451 GNRSDTVTIN SDGWGEFKVN GGSVSVWVPR KTT Sequence ID "17"    259SB 1 TNLNGTLMQY FEWYTPNDGQ HWKRLQNDSA YLAEHGITAV WIPPAYKGTS
 51 QADVGYGAYD LYDLGEFHQK GTVRTKYGTK GELQSAIKSL HSRDINVYGD
101 VVINHKGGAD ATEDVTAVEV DPADRNRVIS GEYLIKAWTH FHFPGRGSTY
151 SDFKWHWYHF DGTDWDESRK LNRIYKFQGK AWDWEV<u>DTEN</u> GNYDYLMYAD
201 IDYDHPDVVA EIKRWGTWYA NELQLDGFRL DAVKHI<u>K</u>FSF LRDWVNHVRE
251 KTGKEMFTVG EYWSYDINKL HNYITKTNGT MSLFDAPLHN KFYTASKSGG
301 AFDMRTLMTN TLMKDQPTLA VTFVDNHDTE PGQALQSWVD PWFKPLAYAF
351 ILTRQEGYPC VFYGDYYGIP QYNIPSLKSK IDPLLIARRD YAYGTQHDYL
401 DHSDIIGWTR EGVTEKPGSG LAALITDGPG GSKWMYVGKQ HAGKVFYDLT
451 GNRSDTVTIN SDGWGEFKVN GGSVSVWVPR KTT

FIG. 7E

Sequence ID No.18 Nucleotide sequence of gene coding for B. licheniformis AmyL protein (SEQ ID NO: 1)
ACAAATCTTAATGGGACGCTGATGCAGTATTTTGAATGGTACACGCCCAATGACGGCCAACATTG
GAAGCGTCTGCAAAAACGACTCGGCATATTTGGCTGAACACGGTATTACTGCCGTCTGGATTCCCC
CGGCATATAAGGGAACGAGCCAAGCGGATGTGGGCTACGGTGCTTACGACCTTTATGATTTAGGG
GAGTTTCATCAAAAAGGGACGGTTCGGACAAAGTACGGCACAAAAGGAGAGCTGCAATCTGCGAT
CAAAAGTCTTCATTCCCGCGACATTAACGTTTACGGGGATGTGGTCATCAACCACAAAGGCGGCG
CTGATGCGACCGAAGATGTAACCGCGGTTGAAGTCGATCCCGCTGACCGCAACCGCGTAATTTCC
GGAGAATACCTAATTAAAGCCTGGACACATTTTCATTTTCCGGGGCGCGGCAGCACATACAGCGA
TTTTAAATGGCATTGGTACCATTTTGACGGAACCGATTGGGACGAGTCCCGAAAGCTGAACCGCA
TCTATAAGTTTCAAGGAAAGGCTTGGGATTGGGAAGTTTCCAGTGAAAACGGCAACTATGATTAT
TTGATGTATGCCGACATCGATTATGACCATCCTGATGTCGTAGCAGAAATTAAGAGATGGGGCAC
TTGGTATGCCAATGAGCTCCAATTGGACGGTTTCCGTCTTGATGCTGTCAAACACATTAAATTTT
CTTTTTTGCGGGATTGGGTTAATCATGTCAGGGAAAAACGGGGAAGGAAATGTTTACGGTAGCT
GAATATTGGCAGAATGACTTGGGCGCGCTGGAAAACTATTTGAACAAAACAAATTTTAATCATTC
AGTGTTTGACGTGCCGCTTCATTATCAGTTCCATGCTGCATCGACACAGGGAGGCGGCTATGATA
TGAGGAAATTGCTGAACGGTACGGTCGTTTCCAAGCATCCGTTGAAATCGGTTACATTTGTCGAT
AACCATGATACACAGCCGGGGCAGTCGCTTGAGTCGACTGTCCAAACATGGTTTAAGCCGCTTGC
TTACGCTTTTATTCTCACAAGGGAATCTGGATACCCTCAGGTTTTCTACGGGGATATGTACGGGA
CGAAAGGAGACTCCCAGCGCGAAATTCCTGCCTTGAAACACAAAATTGAACCGATCTTAAAAGCG
AGAAAACAGTATGCGTACGGAGCACAGCATGATTATTTCGACCACCATGACATTGTCGGCTGGAC
AAGGGAAGGCGACAGCTCGGTTGCAAATTCAGGTTTGGCGGCATTAATAACAGACGGACCCGGTG
GGGCAAAGCGAATGTATGTCGGCCGGCAAAACGCCGGTGAGACATGGCATGACATTACCGGAAAC
CGTTCGGAGCCGGTTGTCATCAATTCGGAAGGCTGGGGAGAGTTTCACGTAAACGGCGGGTCGGT
TTCAATTTATGTTCAAAGA Sequence ID No. 19 Nucleotide sequence of gene coding for B. stearothermophilus AmyS protein (SEQ ID NO: 2).
GCCGCACCGTTTAACGGTACCATGATGCAGTATTTTGAATGGTACTTGCCGGATGATGGCACGTT
ATGGACCAAAGTGGCCAATGAAGCCAACAACTTATCCAGCCTTGGCATCACCGCTCTTTGGCTGC
CGCCCGCTTACAAAGGAACAAGCCGCAGCGACGTAGGGTACGGAGTATACGACTTGTATGACCTC
GGCGAATTCAATCAAAAAGGGACCGTCCGCACAAAATATGGAACAAAAGCTCAATATCTTCAAGC
CATTCAAGCCGCCCACGCCGCTGGAATGCAAGTGTACGCCGATGTCGTGTTCGACCATAAAGGCG
GCGCTGACGGCACGGAATGGGTGGACGCCGTCGAAGTCAATCCGTCCGACCGCAACCAAGAAATC
TCGGGCACCTATCAAATCCAAGCATGGACGAAATTTGATTTTCCCGGCGGGGCAACACCTACTC
CAGCTTTAAGTGGCGCTGGTACCATTTTGACGGCGTTGATTGGGACGAAAGCCGAAAATTAAGCC
GCATTTACAAATTCAGGGGCATCGGCAAAGCGTGGGATTGGGAAGTAGACACAGAAAACGGAAAC
TATGACTACTTAATGTATGCCGACCTTGATATGGATCATCCCGAAGTCGTGACCGAGCTGAAAAA
CTGGGGGAAATGGTATGTCAACACAACGAACATTGATGGGTTCCGGCTTGATGCCGTCAAGCATA
TTAAGTTCAGTTTTTTTCCTGATTGGTTGTCGTATGTGCGTTCTCAGACTGGCAAGCCGCTATTT
ACCGTCGGGGAATATTGGAGCTATGACATCAACAAGTTGCACAATTACATTACGAAAACAAACGG
AACGATGTCTTTGTTTGATGCCCCGTTACACAACAAATTTTATACCGCTTCCAAATCAGGGGGCG
CATTTGATATGCGCACGTTAATGACCAATACTCTCATGAAAGATCAACCGACATTGGCCGTCACC
TTCGTTGATAATCATGACACCGAACCCGGCCAAGCGCTTCAGTCATGGGTCGACCCATGGTTCAA
ACCGTTGGCTTACGCCTTTATTCTAACTCGGCAGGAAGGATACCCGTGCGTCTTTTATGGTGACT
ATTATGGCATTCCACAATATAACATTCCTTCGCTGAAAAGCAAAATCGATCCGCTCCTCATCGCG
CGCAGGGATTATGCTTACGGAACGCAACATGATTATCTTGATCACTCCGACATCATCGGGTGGAC
AAGGGAAGGGGTCACTGAAAAACCAGGATCCGGGCTGGCCGCACTGATCACCGATGGGCCGGGAG
GAAGCAAATGGATGTACGTTGGCAAACAACACGCTGGAAAGTGTTCTATGACCTTACCGGCAAC
CGGAGTGACACCGTCACCATCAACAGTGATGGATGGGGGGAATTCAAGTCAATGGCGGTTCGGT
TTCGGTTTGGGTTCCTAGAAAAACGACC

*FIG. 8A*

Sequence ID no. 20  Nucleotide sequence of gene coding for precursor
of AmyS control protein (precursor)
GCCGCACCGTTTAACGGTACCATGATGCAGTATTTTGAATGGTACTTGCCGGATGATGGCACGTT
ATGGACCAAAGTGGCCAATGAAGCCAACAACTTATCCAGCCTTGGCATCACCGCTCTTTGGCTGC
CGCCCGCTTACAAAGGAACAAGCCGCAGCGACGTAGGGTACGGAGTATACGACTTGTATGACCTC
GGCGAATTCAATCAAAAAGGGACCGTCCGCACAAAATATGGAACAAAAGCTCAATATCTTCAAGC
CATTCAAGCCGCCCACGCCGCTGGAATGCAAGTGTACGCCGATGTCGTGTTCGACCATAAAGGCG
GCGCTGACGGCACGGAATGGGTGGACGCCGTCGAAGTCAATCCGTCCGACCGCAACCAAGAAATC
TCGGGCACCTATCAAATCCAAGCATGGACGAAATTTGATTTTCCCGGGCGGGGCAACACCTACTC
CAGCTTTAAGTGGCGCTGGTACCATTTTGACGGCGTTGACTGGGACGAAAGCCGAAAATTAAGCC
GCATTTACAAATTCATCGGCAAAGCGTGGGATTGGGAAGTAGACACAGAAAACGGAAACTATGAC
TACTTAATGTATGCCGACCTTGATATGGATCATCCCGAAGTCGTGACCGAGCTGAAAAACTGGGG
GAAATGGTATGTCAACACAACGAACATTGATGGGTTCCGGCTTGATGCCGTCAAGCATATTAAGT
TCAGTTTTTTTCCTGATTGGTTGTCGTATGTGCGTTCTCAGACTGGCAAGCCGCTATTTACCGTC
GGGGAATATTGGAGCTATGACATCAACAAGTTGCACAATTACATTACGAAAACAAACGGAACGAT
GTCTTTGTTTGATGCCCCGTTACACAACAAATTTTATACCGCTTCCAAATCAGGGGGCGCATTTG
ATATGCGCACGTTAATGACCAATACTCTCATGAAAGATCAACCGACATTGGCCGTCACCTTCGTT
GATAATCATGACACCGAACCCGGCCAAGCGCTTCAGTCATGGGTCGACCCATGGTTCAAACCGTT
GGCTTACGCCTTTATTCTAACTCGGCAGGAAGGATACCCGTGCGTCTTTTATGGTGACTATTATG
GCATTCCACAATATAACATTCCTTCGCTGAAAAGCAAAATCGATCCGCTCCTCATCGCGCGCAGG
GATTATGCTTACGGAACGCAACATGATTATCTTGATCACTCCGACATCATCGGGTGGACAAGGGA
AGGGGTCACTGAAAAACCAGGATCCGGGCTGGCCGCACTGATCACCGATGGGCCGGGAGGAAGCA
AATGGATGTACGTTGGCAAACAACACGCTGGAAAAGTGTTCTATGACCTTACCGGCAACCGGAGT
GACACCGTCACCATCAACAGTGATGGATGGGGGAATTCAAAGTCAATGGCGGTTCGGTTTCGGT
TTGGGTTCCTAGAAAAACGACCGTTTCTACCATCGCTCGGCCGATCACAACCCGACCGTGGACTG
GTGAATTCGTCCGTTGGACCGAACCACGGTTGGTGGCATGGCCT Sequence ID no. 21. Nucleotide sequence of gene coding hybrid 186
protein
ACAAATCTTAATGGGACGCTGATGCAGTATTTTGAATGGTACACGCCCAATGACGGCCAACATTG
GAAGCGTCTGCAAAACGACTCGGCATATTTGGCTGAACACGGTATTACTGCCGTCTGGATTCCCC
CGGCATATAAGGGAACGAGCCAAGCGGATGTGGGCTACGGTGCTTACGACCTTTATGATTTAGGG
GAGTTTCATCAAAAAGGGACGGTTCGGACAAAGTACGGCACAAAAGGAGAGCTGCAATCTGCGAT
CAAAAGTCTTCATTCCCGCGACATTAACGTTTACGGGGATGTGGTCATCAACCACAAAGGCGGCG
CTGATGCGACCGAAGATGTAACCGCGGTTGAAGTCGATCCCGCTGACCGCAACCGCGTAATTTCC
GGAGAATACCTAATTAAAGCCTGGACACATTTTCATTTTCCGGGGCGCGGCAGCACATACAGCGA
TTTTAAATGGCATTGGTACCATTTTGACGGAACCGATTGGGACGAGTCCCGAAAGCTGAACCGCA
TCTATAAGTTTCAAGGAAAGGCTTGGGATTGGGAAGTTGACACAGAAAACGGAAACTATGACTAC
TTAATGTATGCCGACCTTGATATGGATCATCCCGAAGTCGTGACCGAGCTGAAAAACTGGGGGAA
ATGGTATGTCAACACAACGAACATTGATGGGTTCCGGCTTGATGCCGTCAAGCATATTAAGTTCA
GTTTTTTTCCTGATTGGTTGTCGTATGTGCGTTCTCAGACTGGCAAGCCGCTATTTACCGTCGGG
GAATATTGGAGCTATGACATCAACAAGTTGCACAATTACATTACGAAAACAAACGGAACGATGTC
TTTGTTTGATGCCCCGTTACACAACAAATTTTATACCGCTTCCAAATCAGGGGGCGCATTTGATA
TGCGCACGTTAATGACCAATACTCTCATGAAAGATCAACCGACATTGGCCGTCACCTTCGTTGAT
AATCATGACACCGAGCCCGGCCAAGCGCTTCAGTCATGGGTCGACCCATGGTTCAAACCGTTGGC
TTACGCCTTTATTCTAACTCGGCAGGAAGGATACCCGTGCGTCTTTTATGGTGACTATTATGGCA
TTCCACAATATAACATTCCTTCGCTGAAAAGCAAAATCGATCCGCTCCTCATCGCGCGCAGGGAT
TATGCTTACGGAACGCAACATGATTATCTTGATCACTCCGACATCATCGGGTGGACAAGGGAAGG
GGTCACTGAAAAACCAGGATCCGGGCTGGCCGCACTGATCACCGATGGGCCGGGAGGAAGCAAAT
GGATGTACGTTGGCAAACAACACGCTGGAAAAGTGTTCTATGACCTTACCGGCAACCGGAGTGAC
ACCGTCACCATCAACAGTGATGGATGGGGGAATTCAAAGTCAATGGCGGTTCGGTTTCGGTTTG
GGTTCCTAGAAAAACGACC

*FIG. 8B*

Sequence ID No. 22. Nucleotide sequence of gene coding hybrid
187 protein
ACAAATCTTAATGGGACGCTGATGCAGTATTTTGAATGGTACACGCCCAATGACGGCCAACATTG
GAAGCGTCTGCAAAACGACTCGGCATATTTGGCTGAACACGGTATTACTGCCGTCTGGATTCCCC
CGGCATATAAGGGAACGAGCCAAGCGGATGTGGGCTACGGTGCTTACGACCTTTATGATTTAGGG
GAGTTTCATCAAAAAGGGACGGTTCGGACAAAGTACGGCACAAAAGGAGAGCTGCAATCTGCGAT
CAAAAGTCTTCATTCCCGCGACATTAACGTTTACGGGGATGTGGTCATCAACCACAAAGGCGGCG
CTGATGCGACCGAAGATGTAACCGCGGTTGAAGTCGATCCCGCTGACCGCAACCGCGTAATTTCC
GGAGAATACCTAATTAAAGCCTGGACACATTTTCATTTTCCGGGGCGCGGCAGCACATACAGCGA
TTTTAAATGGCATTGGTACCATTTTGACGGAACCGATTGGGACGAGTCCCGAAAGCTGAACCGCA
TCTATAAGTTTCAAGGAAAGGCTTGGGATTGGGAAGTTTCCACAGAAAACGGAAACTATGACTAC
TTAATGTATGCCGACCTTGATATGGATCATCCCGAAGTCGTGACCGAGCTGAAAAACTGGGGGAA
ATGGTATGTCAACACAACGAACATTGATGGGTTCCGGCTTGATGCCGTCAAGCATATTAAGTTCA
GTTTTTTTCCTGATTGGTTGTCGTATGTGCGTTCTCAGACTGGCAAGCCGCTATTTACCGTCGGG
GAATATTGGAGCTATGACATCAACAAGTTGCACAATTACATTACGAAAACAAACGGAACGATGTC
TTTGTTTGATGCCCCGTTACACAACAAATTTTATACCGCTTCCAAATCAGGGGGCGCATTTGATA
TGCGCACGTTAATGACCAATACTCTCATGAAAGATCAACCGACATTGGCCGTCACCTTCGTTGAT
AATCATGACACCGAGCCCGGCCAAGCGCTTCAGTCATGGGTCGACCCATGGTTCAAACCGTTGGC
TTACGCCTTTATTCTAACTCGGCAGGAAGGATACCCGTGCGTCTTTTATGGTGACTATTATGGCA
TTCCACAATATAACATTCCTTCGCTGAAAAGCAAAATCGATCCGCTCCTCATCGCGCGCAGGGAT
TATGCTTACGGAACGCAACATGATTATCTTGATCACTCCGACATCATCGGGTGGACAAGGGAAGG
GGTCACTGAAAAACCAGGATCCGGGCTGGCCGCACTGATCACCGATGGGCCGGGAGGAAGCAAAT
GGATGTACGTTGGCAAACAACACGCTGGAAAAGTGTTCTATGACCTTACCGGCAACCGGAGTGAC
ACCGTCACCATCAACAGTGATGGATGGGGGGAATTCAAAGTCAATGGCGGTTCGGTTTCGGTTTG
GGTTCCTAGAAAAACGACC Sequence ID No. 23. Nucleotide sequence of gene coding hybrid
200 protein
ACAAATCTTAATGGGACGCTGATGCAGTATTTTGAATGGTACACGCCCAATGACGGCCAACATTG
GAAGCGTCTGCAAAACGACTCGGCATATTTGGCTGAACACGGTATTACTGCCGTCTGGATTCCCC
CGGCATATAAGGGAACGAGCCAAGCGGATGTGGGCTACGGTGCTTACGACCTTTATGATTTAGGG
GAGTTTCATCAAAAAGGGACGGTTCGGACAAAGTACGGCACAAAAGGAGAGCTGCAATCTGCGAT
CAAAAGTCTTCATTCCCGCGACATTAACGTTTACGGGGATGTGGTCATCAACCACAAAGGCGGCG
CTGATGCGACCGAAGATGTAACCGCGGTTGAAGTCGATCCCGCTGACCGCAACCGCGTAATTTCC
GGAGAATACCTAATTAAAGCCTGGACACATTTTCATTTTCCGGGGCGCGGCAGCACATACAGCGA
TTTTAAATGGCATTGGTACCATTTTGACGGAACCGATTGGGACGAGTCCCGAAAGCTGAACCGCA
TCTATAAGTTTCAAGGAAAGGCTTGGGATTGGGAAGTTTCCAGTGAAAACGGCAACTATGATTAT
TTGATGTATGCCGACCTTGATATGGATCATCCCGAAGTCGTGACCGAGCTGAAAAACTGGGGGAA
ATGGTATGTCAACACAACGAACATTGATGGGTTCCGGCTTGATGCCGTCAAGCATATTAAGTTCA
GTTTTTTTCCTGATTGGTTGTCGTATGTGCGTTCTCAGACTGGCAAGCCGCTATTTACCGTCGGG
GAATATTGGAGCTATGACATCAACAAGTTGCACAATTACATTACGAAAACAAACGGAACGATGTC
TTTGTTTGATGCCCCGTTACACAACAAATTTTATACCGCTTCCAAATCAGGGGGCGCATTTGATA
TGCGCACGTTAATGACCAATACTCTCATGAAAGATCAACCGACATTGGCCGTCACCTTCGTTGAT
AATCATGACACCGAGCCCGGCCAAGCGCTTCAGTCATGGGTCGACCCATGGTTCAAACCGTTGGC
TTACGCCTTTATTCTAACTCGGCAGGAAGGATACCCGTGCGTCTTTTATGGTGACTATTATGGCA
TTCCACAATATAACATTCCTTCGCTGAAAAGCAAAATCGATCCGCTCCTCATCGCGCGCAGGGAT
TATGCTTACGGAACGCAACATGATTATCTTGATCACTCCGACATCATCGGGTGGACAAGGGAAGG
GGTCACTGAAAAACCAGGATCCGGGCTGGCCGCACTGATCACCGATGGGCCGGGAGGAAGCAAAT
GGATGTACGTTGGCAAACAACACGCTGGAAAAGTGTTCTATGACCTTACCGGCAACCGGAGTGAC
ACCGTCACCATCAACAGTGATGGATGGGGGGAATTCAAAGTCAATGGCGGTTCGGTTTCGGTTTG
GGTTCCTAGAAAAACGACC

*FIG. 8C*

Sequence ID No. 24. Nucleotide sequence of gene coding hybrid
200SB protein
ACAAATCTTAATGGGACGCTGATGCAGTATTTTGAATGGTACACGCCCAATGACGGCCAACATTG
GAAGCGTCTGCAAAACGACTCGGCATATTTGGCTGAACACGGTATTACTGCCGTCTGGATTCCCC
CGGCATATAAGGGAACGAGCCAAGCGGATGTGGGCTACGGTGCTTACGACCTTTATGATTTAGGG
GAGTTTCATCAAAAAGGGACGGTTCGGACAAAGTACGGCACAAAAGGAGAGCTGCAATCTGCGAT
CAAAAGTCTTCATTCCCGCGACATTAACGTTTACGGGGATGTGGTCATCAACCACAAAGGCGGCG
CTGATGCGACCGAAGATGTAACCGCGGTTGAAGTCGATCCCGCTGACCGCAACCGCGTAATTTCC
GGAGAATACCTAATTAAAGCCTGGACACATTTTCATTTTCCGGGGCGCGGCAGCACATACAGCGA
TTTTAAATGGCATTGGTACCATTTTGACGGAACCGATTGGGACGAGTCCCGAAAGCTGAACCGCA
TCTATAAGTTTCAAGGAAAGGCTTGGGATTGGGAAGTTGACACAGAAAACGGCAACTATGATTAT
TTGATGTATGCCGACCTTGATATGGATCATCCCGAAGTCGTGACCGAGCTGAAAAACTGGGGGAA
ATGGTATGTCAACACAACGAACATTGATGGGTTCCGGCTTGATGCCGTCAAGCATATTAAGTTCA
GTTTTTTTCCTGATTGGTTGTCGTATGTGCGTTCTCAGACTGGCAAGCCGCTATTTACCGTCGGG
GAATATTGGAGCTATGACATCAACAAGTTGCACAATTACATTACGAAAACAAACGGAACGATGTC
TTTGTTTGATGCCCCGTTACACAACAAATTTTATACCGCTTCCAAATCAGGGGGCGCATTTGATA
TGCGCACGTTAATGACCAATACTCTCATGAAAGATCAACCGACATTGGCCGTCACCTTCGTTGAT
AATCATGACACCGAGCCCGGCCAAGCGCTTCAGTCATGGGTCGACCCATGGTTCAAACCGTTGGC
TTACGCCTTTATTCTAACTCGGCAGGAAGGATACCCGTGCGTCTTTTATGGTGACTATTATGGCA
TTCCACAATATAACATTCCTTCGCTGAAAAGCAAAATCGATCCGCTCCTCATCGCGCGCAGGGAT
TATGCTTACGGAACGCAACATGATTATCTTGATCACTCCGACATCATCGGGTGGACAAGGGAAGG
GGTCACTGAAAAACCAGGATCCGGGCTGGCCGCACTGATCACCGATGGGCCGGGAGGAAGCAAAT
GGATGTACGTTGGCAAACAACACGCTGGAAAAGTGTTCTATGACCTTACCGGCAACCGGAGTGAC
ACCGTCACCATCAACAGTGATGGATGGGGGGAATTCAAAGTCAATGGCGGTTCGGTTTCGGTTTG
GGTTCCTAGAAAAACGACC Sequence ID No. 25. Nucleotide sequence of gene coding hybrid
202 protein.
ACAAATCTTAATGGGACGCTGATGCAGTATTTTGAATGGTACACGCCCAATGACGGCCAACATTG
GAAGCGTCTGCAAAACGACTCGGCATATTTGGCTGAACACGGTATTACTGCCGTCTGGATTCCCC
CGGCATATAAGGGAACGAGCCAAGCGGATGTGGGCTACGGTGCTTACGACCTTTATGATTTAGGG
GAGTTTCATCAAAAAGGGACGGTTCGGACAAAGTACGGCACAAAAGGAGAGCTGCAATCTGCGAT
CAAAAGTCTTCATTCCCGCGACATTAACGTTTACGGGGATGTGGTCATCAACCACAAAGGCGGCG
CTGATGCGACCGAAGATGTAACCGCGGTTGAAGTCGATCCCGCTGACCGCAACCGCGTAATTTCC
GGAGAATACCTAATTAAAGCCTGGACACATTTTCATTTTCCGGGGCGCGGCAGCACATACAGCGA
TTTTAAATGGCATTGGTACCATTTTGACGGAACCGATTGGGACGAGTCCCGAAAGCTGAACCGCA
TCTATAAGTTTCAAGGAAAGGCTTGGGATTGGGAAGTTTCCAGTGAAAACGGCAACTATGATTAT
TTGATGTATGCCGACATCGATATGGATCATCCCGAAGTCGTGACCGAGCTGAAAAACTGGGGGAA
ATGGTATGTCAACACAACGAACATTGATGGGTTCCGGCTTGATGCCGTCAAGCATATTAAGTTCA
GTTTTTTTCCTGATTGGTTGTCGTATGTGCGTTCTCAGACTGGCAAGCCGCTATTTACCGTCGGG
GAATATTGGAGCTATGACATCAACAAGTTGCACAATTACATTACGAAAACAAACGGAACGATGTC
TTTGTTTGATGCCCCGTTACACAACAAATTTTATACCGCTTCCAAATCAGGGGGCGCATTTGATA
TGCGCACGTTAATGACCAATACTCTCATGAAAGATCAACCGACATTGGCCGTCACCTTCGTTGAT
AATCATGACACCGAGCCCGGCCAAGCGCTTCAGTCATGGGTCGACCCATGGTTCAAACCGTTGGC
TTACGCCTTTATTCTAACTCGGCAGGAAGGATACCCGTGCGTCTTTTATGGTGACTATTATGGCA
TTCCACAATATAACATTCCTTCGCTGAAAAGCAAAATCGATCCGCTCCTCATCGCGCGCAGGGAT
TATGCTTACGGAACGCAACATGATTATCTTGATCACTCCGACATCATCGGGTGGACAAGGGAAGG
GGTCACTGAAAAACCAGGATCCGGGCTGGCCGCACTGATCACCGATGGGCCGGGAGGAAGCAAAT
GGATGTACGTTGGCAAACAACACGCTGGAAAAGTGTTCTATGACCTTACCGGCAACCGGAGTGAC
ACCGTCACCATCAACAGTGATGGATGGGGGGAATTCAAAGTCAATGGCGGTTCGGTTTCGGTTTG
GGTTCCTAGAAAAACGACC

FIG. 8D

Sequence ID No. 26. Nucleotide sequence of gene coding hybrid
202SB protein.
ACAAATCTTAATGGGACGCTGATGCAGTATTTTGAATGGTACACGCCCAATGACGGCCAACATTG
GAAGCGTCTGCAAAACGACTCGGCATATTTGGCTGAACACGGTATTACTGCCGTCTGGATTCCCC
CGGCATATAAGGGAACGAGCCAAGCGGATGTGGGCTACGGTGCTTACGACCTTTATGATTTAGGG
GAGTTTCATCAAAAAGGGACGGTTCGGACAAAGTACGGCACAAAAGGAGAGCTGCAATCTGCGAT
CAAAAGTCTTCATTCCCGCGACATTAACGTTTACGGGGATGTGGTCATCAACCACAAAGGCGGCG
CTGATGCGACCGAAGATGTAACCGCGGTTGAAGTCGATCCCGCTGACCGCAACCGCGTAATTTCC
GGAGAATACCTAATTAAAGCCTGGACACATTTTCATTTTCCGGGGCGCGGCAGCACATACAGCGA
TTTTAAATGGCATTGGTACCATTTTGACGGAACCGATTGGGACGAGTCCCGAAAGCTGAACCGCA
TCTATAAGTTTCAAGGAAAGGCTTGGGATTGGGAAGTT<u>GACACA</u>GAAAACGGCAACTATGATTAT
TTGATGTATGCCGACATCGAT**ATGGATCATCCCGAAGTCGTGACCGAGCTGAAAAACTGGGGGAA
ATGGTATGTCAACACAACGAACATTGATGGGTTCCGGCTTGATGCCGTCAAGCATATTAAGTTCA
GTTTTTTTCCTGATTGGTTGTCGTATGTGCGTTCTCAGACTGGCAAGCCGCTATTTACCGTCGGG
GAATATTGGAGCTATGACATCAACAAGTTGCACAATTACATTACGAAAACAAACGGAACGATGTC
TTTGTTTGATGCCCCGTTACACAACAAATTTTATACCGCTTCCAAATCAGGGGCGCATTTGATA
TGCGCACGTTAATGACCAATACTCTCATGAAAGATCAACCGACATTGGCCGTCACCTTCGTTGAT
AATCATGACACCGAGCCCGGCCAAGCGCTTCAGTCATGGGTCGACCCATGGTTCAAACCGTTGGC
TTACGCCTTTATTCTAACTCGGCAGGAAGGATACCCGTGCGTCTTTTATGGTGACTATTATGGCA
TTCCACAATATAACATTCCTTCGCTGAAAAGCAAAATCGATCCGCTCCTCATCGCGCGCAGGGAT
TATGCTTACGGAACGCAACATGATTATCTTGATCACTCCGACATCATCGGGTGGACAAGGGAAGG
GGTCACTGAAAAACCAGGATCCGGGCTGGCCGCACTGATCACCGATGGGCCGGGAGGAAGCAAAT
GGATGTACGTTGGCAAACAACACGCTGGAAAAGTGTTCTATGACCTTACCGGCAACCGGAGTGAC
ACCGTCACCATCAACAGTGATGGATGGGGGGAATTCAAAGTCAATGGCGGTTCGGTTTCGGTTTG
GGTTCCTAGAAAAACGACC**

Sequence ID No. 27. Nucleotide sequence of gene coding hybrid
228 protein.
ACAAATCTTAATGGGACGCTGATGCAGTATTTTGAATGGTACACGCCCAATGACGGCCAACATTG
GAAGCGTCTGCAAAACGACTCGGCATATTTGGCTGAACACGGTATTACTGCCGTCTGGATTCCCC
CGGCATATAAGGGAACGAGCCAAGCGGATGTGGGCTACGGTGCTTACGACCTTTATGATTTAGGG
GAGTTTCATCAAAAAGGGACGGTTCGGACAAAGTACGGCACAAAAGGAGAGCTGCAATCTGCGAT
CAAAAGTCTTCATTCCCGCGACATTAACGTTTACGGGGATGTGGTCATCAACCACAAAGGCGGCG
CTGATGCGACCGAAGATGTAACCGCGGTTGAAGTCGATCCCGCTGACCGCAACCGCGTAATTTCC
GGAGAATACCTAATTAAAGCCTGGACACATTTTCATTTTCCGGGGCGCGGCAGCACATACAGCGA
TTTTAAATGGCATTGGTACCATTTTGACGGAACCGATTGGGACGAGTCCCGAAAGCTGAACCGCA
TCTATAAGTTTCAAGGAAAGGCTTGGGATTGGGAAGTTTCCAGTGAAAACGGCAACTATGATTAT
TTGATGTATGCCGACATCGATTATGACCATCCTGATGTCGTAGCAGAAATTAAGAGATGGGGCAC
TTGGTATGCCAATGAGCTCCAATTGGACGGTTTC**CGGCTTGATGCCGTCAAGCATATTAAGTTCA
GTTTTTTTCCTGATTGGTTGTCGTATGTGCGTTCTCAGACTGGCAAGCCGCTATTTACCGTCGGG
GAATATTGGAGCTATGACATCAACAAGTTGCACAATTACATTACGAAAACAAACGGAACGATGTC
TTTGTTTGATGCCCCGTTACACAACAAATTTTATACCGCTTCCAAATCAGGGGCGCATTTGATA
TGCGCACGTTAATGACCAATACTCTCATGAAAGATCAACCGACATTGGCCGTCACCTTCGTTGAT
AATCATGACACCGAGCCCGGCCAAGCGCTTCAGTCATGGGTCGACCCATGGTTCAAACCGTTGGC
TTACGCCTTTATTCTAACTCGGCAGGAAGGATACCCGTGCGTCTTTTATGGTGACTATTATGGCA
TTCCACAATATAACATTCCTTCGCTGAAAAGCAAAATCGATCCGCTCCTCATCGCGCGCAGGGAT
TATGCTTACGGAACGCAACATGATTATCTTGATCACTCCGACATCATCGGGTGGACAAGGGAAGG
GGTCACTGAAAAACCAGGATCCGGGCTGGCCGCACTGATCACCGATGGGCCGGGAGGAAGCAAAT
GGATGTACGTTGGCAAACAACACGCTGGAAAAGTGTTCTATGACCTTACCGGCAACCGGAGTGAC
ACCGTCACCATCAACAGTGATGGATGGGGGGAATTCAAAGTCAATGGCGGTTCGGTTTCGGTTTG
GGTTCCTAGAAAAACGACC**

FIG. 8E

Sequence ID No. 28. Nucleotide sequence of gene coding hybrid
228SB protein.
GCGAATCTTAATGGGACGCTGATGCAGTATTTTGAATGGTACACGCCCAATGACGGCCAACATTG
GAAGCGTCTGCAAAACGACTCGGCATATTTGGCTGAACACGGTATTACTGCCGTCTGGATTCCCC
CGGCATATAAGGGAACGAGCCAAGCGGATGTGGGCTACGGTGCTTACGACCTTTATGATTTAGGG
GAGTTTCATCAAAAAGGGACGGTTCGGACAAAGTACGGCACAAAAGGAGAGCTGCAATCTGCGAT
CAAAAGTCTTCATTCCCGCGACATTAACGTTTACGGGGATGTGGTCATCAACCACAAAGGCGGCG
CTGATGCGACCGAAGATGTAACCGCGGTTGAAGTCGATCCCGCTGACCGCAACCGCGTAATTTCC
GGAGAATACCTAATTAAAGCCTGGACACATTTTCATTTTCCGGGGCGCGGCAGCACATACAGCGA
TTTTAAATGGCATTGGTACCATTTTGACGGAACCGATTGGGACGAGTCCCGAAAGCTGAACCGCA
TCTATAAGTTTCAAGGAAAGGCTTGGGATTGGGAAGTT<u>GACACA</u>GAAAACGGCAACTATGATTAT
TTGATGTATGCCGACATCGATTATGACCATCCTGATGTCGTAGCAGAAATTAAGAGATGGGGCAC
TTGGTATGCCAATGAGCTCCAATTGGACGGTTTC**CGGCTTGATGCCGTCAAGCATATTAAGTTCA
GTTTTTTTCCTGATTGGTTGTCGTATGTGCGTTCTCAGACTGGCAAGCCGCTATTTACCGTCGGG
GAATATTGGAGCTATGACATCAACAAGTTGCACAATTACATTACGAAAACAAACGGAACGATGTC
TTTGTTTGATGCCCCGTTACACAACAAATTTTATACCGCTTCCAAATCAGGGGGCGCATTTGATA
TGCGCACGTTAATGACCAATACTCTCATGAAAGATCAACCGACATTGGCCGTCACCTTCGTTGAT
AATCATGACACCGAGCCCGGCCAAGCGCTTCAGTCATGGGTCGACCCATGGTTCAAACCGTTGGC
TTACGCCTTTATTCTAACTCGGCAGGAAGGATACCCGTGCGTCTTTTATGGTGACTATTATGGCA
TTCCACAATATAACATTCCTTCGCTGAAAAGCAAAATCGATCCGCTCCTCATCGCGCGCAGGGAT
TATGCTTACGGAACGCAACATGATTATCTTGATCACTCCGACATCATCGGGTGGACAAGGGAAGG
GGTCACTGAAAAACCAGGATCCGGGCTGGCCGCACTGATCACCGATGGGCCGGGAGGAAGCAAAT
GGATGTACGTTGGCAAACAACACGCTGGAAAAGTGTTCTATGACCTTACCGGCAACCGGAGTGAC
ACCGTCACCATCAACAGTGATGGATGGGGGGAATTCAAAGTCAATGGCGGTTCGGTTTCGGTTTG
GGTTCCTAGAAAAACGACC**

Sequence ID No. 29. Nucleotide sequence of gene coding hybrid
249 protein.
ACAAATCTTAATGGGACGCTGATGCAGTATTTTGAATGGTACACGCCCAATGACGGCCAACATTG
GAAGCGTCTGCAAAACGACTCGGCATATTTGGCTGAACACGGTATTACTGCCGTCTGGATTCCCC
CGGCATATAAGGGAACGAGCCAAGCGGATGTGGGCTACGGTGCTTACGACCTTTATGATTTAGGG
GAGTTTCATCAAAAAGGGACGGTTCGGACAAAGTACGGCACAAAAGGAGAGCTGCAATCTGCGAT
CAAAAGTCTTCATTCCCGCGACATTAACGTTTACGGGGATGTGGTCATCAACCACAAAGGCGGCG
CTGATGCGACCGAAGATGTAACCGCGGTTGAAGTCGATCCCGCTGACCGCAACCGCGTAATTTCC
GGAGAATACCTAATTAAAGCCTGGACACATTTTCATTTTCCGGGGCGCGGCAGCACATACAGCGA
TTTTAAATGGCATTGGTACCATTTTGACGGAACCGATTGGGACGAGTCCCGAAAGCTGAACCGCA
TCTATAAGTTTCAAGGAAAGGCTTGGGATTGGGAAGTTTCCAGTGAAAACGGCAACTATGATTAT
TTGATGTATGCCGACATCGATTATGACCATCCTGATGTCGTAGCAGAAATTAAGAGATGGGGCAC
TTGGTATGCCAATGAGCTCCAATTGGACGGTTTCCGTCTTGATGCTGTCAAACACATTAAATTTT
CTTTTTTGCGGGATTGGGTTAATCATGTCAGG**TCTCAGACTGGCAAGCCGCTATTTACCGTCGGG
GAATATTGGAGCTATGACATCAACAAGTTGCACAATTACATTACGAAAACAAACGGAACGATGTC
TTTGTTTGATGCCCCGTTACACAACAAATTTTATACCGCTTCCAAATCAGGGGGCGCATTTGATA
TGCGCACGTTAATGACCAATACTCTCATGAAAGATCAACCGACATTGGCCGTCACCTTCGTTGAT
AATCATGACACCGAGCCCGGCCAAGCGCTTCAGTCATGGGTCGACCCATGGTTCAAACCGTTGGC
TTACGCCTTTATTCTAACTCGGCAGGAAGGATACCCGTGCGTCTTTTATGGTGACTATTATGGCA
TTCCACAATATAACATTCCTTCGCTGAAAAGCAAAATCGATCCGCTCCTCATCGCGCGCAGGGAT
TATGCTTACGGAACGCAACATGATTATCTTGATCACTCCGACATCATCGGGTGGACAAGGGAAGG
GGTCACTGAAAAACCAGGATCCGGGCTGGCCGCACTGATCACCGATGGGCCGGGAGGAAGCAAAT
GGATGTACGTTGGCAAACAACACGCTGGAAAAGTGTTCTATGACCTTACCGGCAACCGGAGTGAC
ACCGTCACCATCAACAGTGATGGATGGGGGGAATTCAAAGTCAATGGCGGTTCGGTTTCGGTTTG
GGTTCCTAGAAAAACGACC**

*FIG. 8F*

Sequence ID no. 30. Nucleotide sequence of gene coding hybrid
249SB protein.
ACAAATCTTAATGGGACGCTGATGCAGTATTTTGAATGGTACACGCCCAATGACGGCCAACATTG
GAAGCGTCTGCAAAACGACTCGGCATATTTGGCTGAACACGGTATTACTGCCGTCTGGATTCCCC
CGGCATATAAGGGAACGAGCCAAGCGGATGTGGGCTACGGTGCTTACGACCTTTATGATTTAGGG
GAGTTTCATCAAAAAGGGACGGTTCGGACAAAGTACGGCACAAAGGAGAGCTGCAATCTGCGAT
CAAAAGTCTTCATTCCCGCGACATTAACGTTTACGGGGATGTGGTCATCAACCACAAAGGCGGCG
CTGATGCGACCGAAGATGTAACCGCGGTTGAAGTCGATCCCGCTGACCGCAACCGCGTAATTTCC
GGAGAATACCTAATTAAAGCCTGGACACATTTTCATTTTCCGGGGCGCGGCAGCACATACAGCGA
TTTTAAATGGCATTGGTACCATTTTGACGGAACCGATTGGGACGAGTCCCGAAAGCTGAACCGCA
TCTATAAGTTTCAAGGAAAGGCTTGGGATTGGGAAGTT<u>GACACA</u>GAAAACGGCAACTATGATTAT
TTGATGTATGCCGACATCGATTATGACCATCCTGATGTCGTAGCAGAAATTAAGAGATGGGGCAC
TTGGTATGCCAATGAGCTCCAATTGGACGGTTTCCGTCTTGATGCTGTCAAACACATTAAATTTT
CTTTTTTGCGGGATTGGGTTAATCATGTCAGG**TCTCAGACTGGCAAGCCGCTATTTACCGTCGGG
GAATATTGGAGCTATGACATCAACAAGTTGCACAATTACATTACGAAAACAAACGGAACGATGTC
TTTGTTTGATGCCCCGTTACACAACAAATTTTATACCGCTTCCAAATCAGGGGCGCATTTGATA
TGCGCACGTTAATGACCAATACTCTCATGAAAGATCAACCGACATTGGCCGTCACCTTCGTTGAT
AATCATGACACCGAGCCCGGCCAAGCGCTTCAGTCATGGGTCGACCCATGGTTCAAACCGTTGGC
TTACGCCTTTATTCTAACTCGGCAGGAAGGATACCCGTGCGTCTTTTATGGTGACTATTATGGCA
TTCCACAATATAACATTCCTTCGCTGAAAAGCAAAATCGATCCGCTCCTCATCGCGCGCAGGGAT
TATGCTTACGGAACGCAACATGATTATCTTGATCACTCCGACATCATCGGGTGGACAAGGGAAGG
GGTCACTGAAAAACCAGGATCCGGGCTGGCCGCACTGATCACCGATGGGCCGGGAGGAAGCAAAT
GGATGTACGTTGGCAAACAACACGCTGGAAAAGTGTTCTATGACCTTACCGGCAACCGGAGTGAC
ACCGTCACCATCAACAGTGATGGATGGGGGGAATTCAAAGTCAATGGCGGTTCGGTTTCGGTTTG
GGTTCCTAGAAAAACGACC**

Sequence ID No. 31. Nucleotide sequence of gene coding hybrid
254 protein.
ACAAATCTTAATGGGACGCTGATGCAGTATTTTGAATGGTACACGCCCAATGACGGCCAACATTG
GAAGCGTCTGCAAAACGACTCGGCATATTTGGCTGAACACGGTATTACTGCCGTCTGGATTCCCC
CGGCATATAAGGGAACGAGCCAAGCGGATGTGGGCTACGGTGCTTACGACCTTTATGATTTAGGG
GAGTTTCATCAAAAAGGGACGGTTCGGACAAAGTACGGCACAAAGGAGAGCTGCAATCTGCGAT
CAAAAGTCTTCATTCCCGCGACATTAACGTTTACGGGGATGTGGTCATCAACCACAAAGGCGGCG
CTGATGCGACCGAAGATGTAACCGCGGTTGAAGTCGATCCCGCTGACCGCAACCGCGTAATTTCC
GGAGAATACCTAATTAAAGCCTGGACACATTTTCATTTTCCGGGGCGCGGCAGCACATACAGCGA
TTTTAAATGGCATTGGTACCATTTTGACGGAACCGATTGGGACGAGTCCCGAAAGCTGAACCGCA
TCTATAAGTTTCAAGGAAAGGCTTGGGATTGGGAAGTTTCCAGTGAAAACGGCAACTATGATTAT
TTGATGTATGCCGACATCGATTATGACCATCCTGATGTCGTAGCAGAAATTAAGAGATGGGGCAC
TTGGTATGCCAATGAGCTCCAATTGGACGGTTTCCGTCTTGATGCTGTCAAACACATTAAATTTT
CTTTTTTGCGGGATTGGGTTAATCATGTCAGGGAAAAAACGGGAAG**CCGCTATTTACCGTCGGG
GAATATTGGAGCTATGACATCAACAAGTTGCACAATTACATTACGAAAACAAACGGAACGATGTC
TTTGTTTGATGCCCCGTTACACAACAAATTTTATACCGCTTCCAAATCAGGGGCGCATTTGATA
TGCGCACGTTAATGACCAATACTCTCATGAAAGATCAACCGACATTGGCCGTCACCTTCGTTGAT
AATCATGACACCGAGCCCGGCCAAGCGCTTCAGTCATGGGTCGACCCATGGTTCAAACCGTTGGC
TTACGCCTTTATTCTAACTCGGCAGGAAGGATACCCGTGCGTCTTTTATGGTGACTATTATGGCA
TTCCACAATATAACATTCCTTCGCTGAAAAGCAAAATCGATCCGCTCCTCATCGCGCGCAGGGAT
TATGCTTACGGAACGCAACATGATTATCTTGATCACTCCGACATCATCGGGTGGACAAGGGAAGG
GGTCACTGAAAAACCAGGATCCGGGCTGGCCGCACTGATCACCGATGGGCCGGGAGGAAGCAAAT
GGATGTACGTTGGCAAACAACACGCTGGAAAAGTGTTCTATGACCTTACCGGCAACCGGAGTGAC
ACCGTCACCATCAACAGTGATGGATGGGGGGAATTCAAAGTCAATGGCGGTTCGGTTTCGGTTTG
GGTTCCTAGAAAAACGACC**

*FIG. 8G*

Sequence ID No. 32. Nucleotide sequence of gene coding hybrid
254SB   protein.
ACAAATCTTAATGGGACGCTGATGCAGTATTTTGAATGGTACACGCCCAATGACGGCCAACATTG
GAAGCGTCTGCAAAACGACTCGGCATATTTGGCTGAACACGGTATTACTGCCGTCTGGATTCCCC
CGGCATATAAGGGAACGAGCCAAGCGGATGTGGGCTACGGTGCTTACGACCTTTATGATTTAGGG
GAGTTTCATCAAAAAGGGACGGTTCGGACAAAGTACGGCACAAAAGGAGAGCTGCAATCTGCGAT
CAAAAGTCTTCATTCCCGCGACATTAACGTTTACGGGGATGTGGTCATCAACCACAAAGGCGGCG
CTGATGCGACCGAAGATGTAACCGCGGTTGAAGTCGATCCCGCTGACCGCAACCGCGTAATTTCC
GGAGAATACCTAATTAAAGCCTGGACACATTTTCATTTTCCGGGGCGCGGCAGCACATACAGCGA
TTTTAAATGGCATTGGTACCATTTTGACGGAACCGATTGGGACGAGTCCCGAAAGCTGAACCGCA
TCTATAAGTTTCAAGGAAAGGCTTGGGATTGGGAAGTTGACACAGAAAACGGCAACTATGATTAT
TGATGTATGCCGACATCGATTATGACCATCCTGATGTCGTAGCAGAAATTAAGAGATGGGGCAC
TTGGTATGCCAATGAGCTCCAATTGGACGGTTTCCGTCTTGATGCTGTCAAACACATTAAATTTT
CTTTTTTGCGGGATTGGGTTAATCATGTCAGGGAAAAACGGGGAAGCCGCTATTTACCGTCGGG
GAATATTGGAGCTATGACATCAACAAGTTGCACAATTACATTACGAAAACAAACGGAACGATGTC
TTTGTTTGATGCCCCGTTACACAACAAATTTTATACCGCTTCCAAATCAGGGGGCGCATTTGATA
TGCGCACGTTAATGACCAATACTCTCATGAAAGATCAACCGACATTGGCCGTCACCTTCGTTGAT
AATCATGACACCGAGCCCGGCCAAGCGCTTCAGTCATGGGTCGACCCATGGTTCAAACCGTTGGC
TTACGCCTTTATTCTAACTCGGCAGGAAGGATACCCGTGCGTCTTTTATGGTGACTATTATGGCA
TTCCACAATATAACATTCCTTCGCTGAAAAGCAAAATCGATCCGCTCCTCATCGCGCGCAGGGAT
TATGCTTACGGAACGCAACATGATTATCTTGATCACTCCGACATCATCGGGTGGACAAGGGAAGG
GGTCACTGAAAAACCAGGATCCGGGCTGGCCGCACTGATCACCGATGGGCCGGGAGGAAGCAAAT
GGATGTACGTTGGCAAACAACACGCTGGAAAAGTGTTCTATGACCTTACCGGCAACCGGAGTGAC
ACCGTCACCATCAACAGTGATGGATGGGGGGAATTCAAAGTCAATGGCGGTTCGGTTTCGGTTTG
GGTTCCTAGAAAAACGACC

Sequence ID No. 33. Nucleotide sequence of gene coding hybrid
259 protein.
ACAAATCTTAATGGGACGCTGATGCAGTATTTTGAATGGTACACGCCCAATGACGGCCAACATTG
GAAGCGTCTGCAAAACGACTCGGCATATTTGGCTGAACACGGTATTACTGCCGTCTGGATTCCCC
CGGCATATAAGGGAACGAGCCAAGCGGATGTGGGCTACGGTGCTTACGACCTTTATGATTTAGGG
GAGTTTCATCAAAAAGGGACGGTTCGGACAAAGTACGGCACAAAAGGAGAGCTGCAATCTGCGAT
CAAAAGTCTTCATTCCCGCGACATTAACGTTTACGGGGATGTGGTCATCAACCACAAAGGCGGCG
CTGATGCGACCGAAGATGTAACCGCGGTTGAAGTCGATCCCGCTGACCGCAACCGCGTAATTTCC
GGAGAATACCTAATTAAAGCCTGGACACATTTTCATTTTCCGGGGCGCGGCAGCACATACAGCGA
TTTTAAATGGCATTGGTACCATTTTGACGGAACCGATTGGGACGAGTCCCGAAAGCTGAACCGCA
TCTATAAGTTTCAAGGAAAGGCTTGGGATTGGGAAGTTTCCAGTGAAAACGGCAACTATGATTAT
TGATGTATGCCGACATCGATTATGACCATCCTGATGTCGTAGCAGAAATTAAGAGATGGGGCAC
TTGGTATGCCAATGAGCTCCAATTGGACGGTTTCCGTCTTGATGCTGTCAAACACATTAAATTTT
CTTTTTTGCGGGATTGGGTTAATCATGTCAGGGAAAAACGGGGAAGGAAATGTTTACGGTAGGG
GAATATTGGAGCTATGACATCAACAAGTTGCACAATTACATTACGAAAACAAACGGAACGATGTC
TTTGTTTGATGCCCCGTTACACAACAAATTTTATACCGCTTCCAAATCAGGGGGCGCATTTGATA
TGCGCACGTTAATGACCAATACTCTCATGAAAGATCAACCGACATTGGCCGTCACCTTCGTTGAT
AATCATGACACCGAGCCCGGCCAAGCGCTTCAGTCATGGGTCGACCCATGGTTCAAACCGTTGGC
TTACGCCTTTATTCTAACTCGGCAGGAAGGATACCCGTGCGTCTTTTATGGTGACTATTATGGCA
TTCCACAATATAACATTCCTTCGCTGAAAAGCAAAATCGATCCGCTCCTCATCGCGCGCAGGGAT
TATGCTTACGGAACGCAACATGATTATCTTGATCACTCCGACATCATCGGGTGGACAAGGGAAGG
GGTCACTGAAAAACCAGGATCCGGGCTGGCCGCACTGATCACCGATGGGCCGGGAGGAAGCAAAT
GGATGTACGTTGGCAAACAACACGCTGGAAAAGTGTTCTATGACCTTACCGGCAACCGGAGTGAC
ACCGTCACCATCAACAGTGATGGATGGGGGGAATTCAAAGTCAATGGCGGTTCGGTTTCGGTTTG
GGTTCCTAGAAAAACGACC

*FIG. 8H*

Sequence ID no. 34. Nucleotide sequence of gene coding hybrid
259SB protein.
ACAAATCTTAATGGGACGCTGATGCAGTATTTTGAATGGTACACGCCCAATGACGGCCAACATTG
GAAGCGTCTGCAAAACGACTCGGCATATTTGGCTGAACACGGTATTACTGCCGTCTGGATTCCCC
CGGCATATAAGGGAACGAGCCAAGCGGATGTGGGCTACGGTGCTTACGACCTTTATGATTTAGGG
GAGTTTCATCAAAAAGGGACGGTTCGGACAAAGTACGGCACAAAAGGAGAGCTGCAATCTGCGAT
CAAAAGTCTTCATTCCCGCGACATTAACGTTTACGGGGATGTGGTCATCAACCACAAAGGCGGCG
CTGATGCGACCGAAGATGTAACCGCGGTTGAAGTCGATCCCGCTGACCGCAACCGCGTAATTTCC
GGAGAATACCTAATTAAAGCCTGGACACATTTTCATTTTCCGGGGCGCGGCAGCACATACAGCGA
TTTTAAATGGCATTGGTACCATTTTGACGGAACCGATTGGGACGAGTCCCGAAAGCTGAACCGCA
TCTATAAGTTTCAAGGAAAGGCTTGGGATTGGGAAGTT<u>GACACA</u>GAAAACGGCAACTATGATTAT
TTGATGTATGCCGACATCGATTATGACCATCCTGATGTCGTAGCAGAAATTAAGAGATGGGGCAC
TTGGTATGCCAATGAGCTCCAATTGGACGGTTTCCGTCTTGATGCTGTCAAACACATTAAATTTT
CTTTTTTGCGGGATTGGGTTAATCATGTCAGGGAAAAAACGGGGAAGGAAATGTTTACGGTA**GGG
GAATATTGGAGCTATGACATCAACAAGTTGCACAATTACATTACGAAAACAAACGGAACGATGTC
TTTGTTTGATGCCCCGTTACACAACAAATTTTATACCGCTTCCAAATCAGGGGGCGCATTTGATA
TGCGCACGTTAATGACCAATACTCTCATGAAAGATCAACCGACATTGGCCGTCACCTTCGTTGAT
AATCATGACACCGAGCCCGGCCAAGCGCTTCAGTCATGGGTCGACCCATGGTTCAAACCGTTGGC
TTACGCCTTTATTCTAACTCGGCAGGAAGGATACCCGTGCGTCTTTTATGGTGACTATTATGGCA
TTCCACAATATAACATTCCTTCGCTGAAAAGCAAAATCGATCCGCTCCTCATCGCGCGCAGGGAT
TATGCTTACGGAACGCAACATGATTATCTTGATCACTCCGACATCATCGGGTGGACAAGGGAAGG
GGTCACTGAAAAACCAGGATCCGGGCTGGCCGCACTGATCACCGATGGGCCGGGAGGAAGCAAAT
GGATGTACGTTGGCAAACAACACGCTGGAAAAGTGTTCTATGACCTTACCGGCAACCGGAGTGAC
ACCGTCACCATCAACAGTGATGGATGGGGGAATTCAAAGTCAATGGCGGTTCGGTTTCGGTTTG
GGTTCCTAGAAAAACGACC**

FIG. 8I

CHIMERIC ALPHA-AMYLASE VARIANTS

CROSS-REFERENCE TO RELATED APPLICATIONS

This application is a Divisional of U.S. patent application Ser. No. 12/990,201, filed on Dec. 16, 2010, which is a 371 National Phase of PCT/US2009/041498, filed Apr. 23, 2009, which claims priority to U.S. Patent Application Ser. No. 61/126,066, filed on Apr. 30, 2008, the contents of which are fully incorporated herein by reference.

SEQUENCE LISTING

The sequence listing submitted via EFS, in compliance with 37 C.F.R. §1.52(e), is incorporated herein by reference. The sequence listing text file submitted via EFS contains the file "31024WO_seqlist.txt", created on Dec. 6, 2013, which is 110,592 bytes in size.

FIELD OF THE INVENTION

This pertains generally to α-amylase enzymes for use in industrial processes, such as liquefaction, baking and cleaning applications. More specifically, it pertains to chimeric α-amylases with improved activity in high temperature applications, and/or that provide improved performance for starch degradation.

BACKGROUND

For many industrial processes that use starches, it is desirable to have amylolytic enzymes that can function under high temperature to rapidly breakdown starch to reduce viscosity. Examples of such enzymes are known in the art. For example, the α-amylases from *Bacillus licheniformis* or *Bacillus stearothermophilus*, AmyL and AmyS respectively, facilitate liquefaction of starches at high temperature. In the absence of added calcium, AmyL and variants of AmyL have higher thermostability than AmyS amylase, and thus are preferred for production of glucose and fructose (e.g., HFCS). AmyS and variants of AmyS are preferred in ethanol producing processes because they have higher specific activity on corn-starch at high temperature than does AmyL or its variants. Thus, AmyS has a faster initial rate of substrate viscosity reduction, which is a highly desirable attribute in starch liquefaction processes. However, AmyS has an undesirable characteristic in that its catalytic activity results in a higher final viscosity at the end of the process than that obtained with AmyL or its variants. The higher final viscosity is likely the result of the lower thermostability, i.e. AmyS is simply inactivated more quickly by the high temperature of the liquefaction process.

Methods of increasing the thermostability of enzymes have been studied. The thermostability of Amy Q (*B. amyloliquefaciens* amylase) was enhanced by the deletion of two amino acids, R176-Gly177, (numbering relative to amino acid sequence of AmyQ) as shown by Suzuki et al. (1989)(*J. Biol. Chem.* 264:18933), which are absent from the AmyL sequence. The thermostability of AmyS-type amylases can be increased by the deletion of two amino acid residues, R179-G180, (AmyS numbering) from a loop (F178 to A184) as shown by Igarashi et al. 1998 (*Biochem. Biophys. Res. Comm.* 248:772). However, a mutated AmyS enzyme with this deletion has a lower specific activity for corn starch hydrolysis at high-temperature than the parent enzyme, negating one of the principal advantages of AmyS amylases, as shown by Shiau et al. (2003) (*Appl. Environ. Micro.* 69:2383).

As discussed above, it is known in the art that, in the absence of added calcium, wild-type AmyL amylase is more thermostable than AmyS amylase. It is further known in the art that the AmyQ, an α-amylase from *Bacillus amyloliquefaciens* that is highly homologous to both AmyS and AmyL, is less thermostable than either AmyS or AmyL. Suzuki et al. (1989) demonstrated that for AmyL-AmyQ-derived hybrids, the N-terminal portion of the AmyL enzymes was required to obtain high stability.

SUMMARY

Provided herein are chimeric polypeptides made preferably from AmyL and AmyS α-amylases. The novel chimeric amylases are useful in that a single enzyme provides the relatively higher thermostability seen in AmyL-type amylases, and the relatively higher specific activity seen in AmyS-type amylases.

Accordingly, provided herein are improved amylase enzymes that provide altered performance properties, for example in terms of their ability to reduce viscosity under high temperature conditions of liquefaction. The chimeric amylases display improved specific activity or the ability to provide a rapid reduction of the peak viscosity in starch liquefaction, as generally observed with AmyS-type amylases. In addition, the chimeric α-amylases have good thermostability, and thus, can provide a low final viscosity as typically seen with AmyL-type enzymes. Polypeptides with improved thermostability, thermostable amylases with increased specific activity, and compositions comprising the polypeptides and enzymes, as well as methods of using the novel enzymes or compositions are provided herein. Nucleic acids encoding the chimeric enzymes, including expression vectors, and host cells that express the chimeric amylases also are provided.

The chimeric α-amylases provide a benefit in that a single chimeric enzyme can provide many of the advantages provided in two separate enzymes. Production benefits for the manufacturer and economic benefits for both the end-user and the manufacturer may flow from the availability of the chimeric amylases described herein.

The chimeric α-amylases are particularly useful in ethanol production processes and other starch degradation processes at high temperature, such as liquefaction processes for syrup production or for fermentation, cleaning applications (e.g. washing, dishwashing), baking, or desizing of woven materials. The enzymes are relatively thermostable, and have good activity across a range of pH conditions, calcium ion concentrations, and redox conditions.

In one aspect, provided are chimeric polypeptides comprising an amino-terminal domain and a carboxy-terminal domain. The amino-terminal domain comprises about 180 or more contiguous amino acid residues of an AmyL amylase. Preferably, the amino-terminal portion comprises an N-terminal portion of the AmyL amylase. The carboxy-terminal domain of the chimeric polypeptides comprises a carboxy-terminal portion of an AmyS amylase. The chimeric polypeptides have an overall length of about 480-515 amino acid residues. The chimeric polypeptides provided herein do not have the primary amino acid sequence of either the AmyL amylase or the AmyS amylase, nor of any other known polypeptide. The chimeric polypeptides have enhanced thermostability relative at least to the AmyS amylase. Thermostability that is equivalent to, or even better than, that of the AmyL is observed in some embodiments.

In another aspect, provided are thermostable chimeric α-amylases. The chimeric amylases comprise an N-terminal portion and a C-terminal portion; the N-terminal portion comprises a contiguous amino acid sequence from an N-terminal portion of an AmyL amylase. The C-terminal portion of the chimeric amylases comprises a contiguous amino acid sequence from a C-terminal portion of an AmyS amylase. The chimeric α-amylases generally have a specific activity greater than that of AmyL amylase. The chimeric amylases also have greater thermostability at 95° C. than AmyS amylase. The primary amino acid sequence of the chimeric amylases is about 475-520 amino acid residues long.

Provided herein are compositions comprising one or more chimeric polypeptides or thermostable chimeric α-amylases as described above, or a combination thereof. The compositions can further comprise one or more additional polypeptides or enzymes. Also provided are food-grade lyophilized compositions comprising the compositions.

In another aspect, provided are polynucleotides that encode a chimeric polypeptide or thermostable α-amylase as provided above, vectors comprising the polynucleotides, and host cells comprising the vectors or polynucleotides. In one embodiment, the polynucleotide encodes a polypeptide having at least about 95% sequence identity to any of SEQ ID NOS: 1-17, but not having the precise sequence of SEQ ID NO: 1 or 2.

Provided as well are methods of making and using the chimeric polypeptides, thermostable α-amylases and the compositions disclosed herein. The methods of using provided herein contemplate the possibility of using one or more additional enzymes, including one or more additional amylases therewith. In one aspect, methods of producing a composition comprising a chimeric polypeptide or a thermostable α-amylase are provided. The methods comprise utilizing a host cell selected from the group consisting of *Bacillus licheniformis, B. subtilis*, and *B. stearothermophilus*, for a fermentation process wherein a protein is expressed, said protein comprising: (a) a chimeric polypeptide having a length of about 480-515 amino acid residues, and comprising an amino-terminal domain comprising about 180 or more contiguous amino acid residues of an N-terminal portion of an AmyL amylase, and a carboxy-terminal domain comprises a carboxy-terminal portion of an AmyS amylase; said chimeric polypeptide having enhanced thermostability relative at least to the AmyS amylase, or (b) a thermostable chimeric α-amylase about 475-520 amino acid residues long, and comprising an N-terminal portion comprising a contiguous amino acid sequence from an N-terminal portion of an AmyL amylase, and a C-terminal portion comprising a contiguous amino acid sequence from a C-terminal portion of an AmyS amylase, said chimeric α-amylase having a specific activity greater than the AmyL amylase and greater thermostability at 95° C. than the AmyS amylase. The methods entail at least partially purifying the expressed protein, to produce the composition.

A method is provided for liquefying a starch slurry comprising: making a slurry comprising a starch, heating the slurry to an acceptable temperature for liquefaction, adding to the slurry a composition comprising one or more of a chimeric polypeptide or thermostable chimeric α-amylase as provided herein, or a combination thereof. Incubating the slurry with the composition for a time and at a temperature sufficient to liquefy the starch slurry completes the method. The method can be used as part of process for producing fuel alcohol.

Also provided is a method of cleaning a surface to remove an unwanted or undesirable starch residue. The method comprises the steps of providing a surface that has starch residue to be removed, contacting the surface with a composition comprising a chimeric polypeptide, thermostable chimeric α-amylase as disclosed herein, or a combination thereof, for a time and at a temperature sufficient to result in removal of the starch residue.

Provided also is a method of treating a woven material that has been previously subjected to contact with a coating comprising starch or a starch-derivative. The method comprises contacting the woven material with a liquid comprising a chimeric α-amylase as provided hereinabove, for a time and under conditions sufficient to substantially remove the coating from the woven material.

Kits for facilitating liquefaction of starch slurry, said kit comprising at least one of: (a) a chimeric polypeptide having a length of about 480-515 amino acid residues, and comprising an amino-terminal domain comprising about 180 or more contiguous amino acid residues of an N-terminal portion of an AmyL amylase, and a carboxy-terminal domain comprises a carboxy-terminal portion of an AmyS amylase; said chimeric polypeptide having enhanced thermostability relative at least to the AmyS control, or (b) a thermostable chimeric α-amylase about 475-520 amino acid residues long, and comprising an N-terminal portion comprising a contiguous amino acid sequence from an N-terminal portion of an AmyL amylase, and a C-terminal portion comprising a contiguous amino acid sequence from a C-terminal portion of an AmyS amylase, said chimeric α-amylase having a specific activity greater than the AmyL amylase and greater thermostability at 95° C. than the AmyS amylase. The kit also comprises instructions for use of the kit in the liquefaction of a starch slurry.

BRIEF DESCRIPTION OF THE DRAWINGS

FIG. 7, panels A-E, shows the amino acid sequences of SEQ IDs 1 to 17. Amino sequence labels: For all hybrid amino acid sequences, Amy L sequence is shown in plain text, Amy S sequence region is shown in bold type, and Salt bridge sequence is shown underlined.

FIG. 8, panels A-I, shows the nucleotide sequences of SEQ IDs 18 to 34. Nucleotide sequence labels: For all hybrid nucleotide sequences, Amy L sequence is shown in plain text, Amy S sequence region is shown in bold type, and Salt bridge sequence is shown underlined.

DETAILED DESCRIPTION

Figure 1:
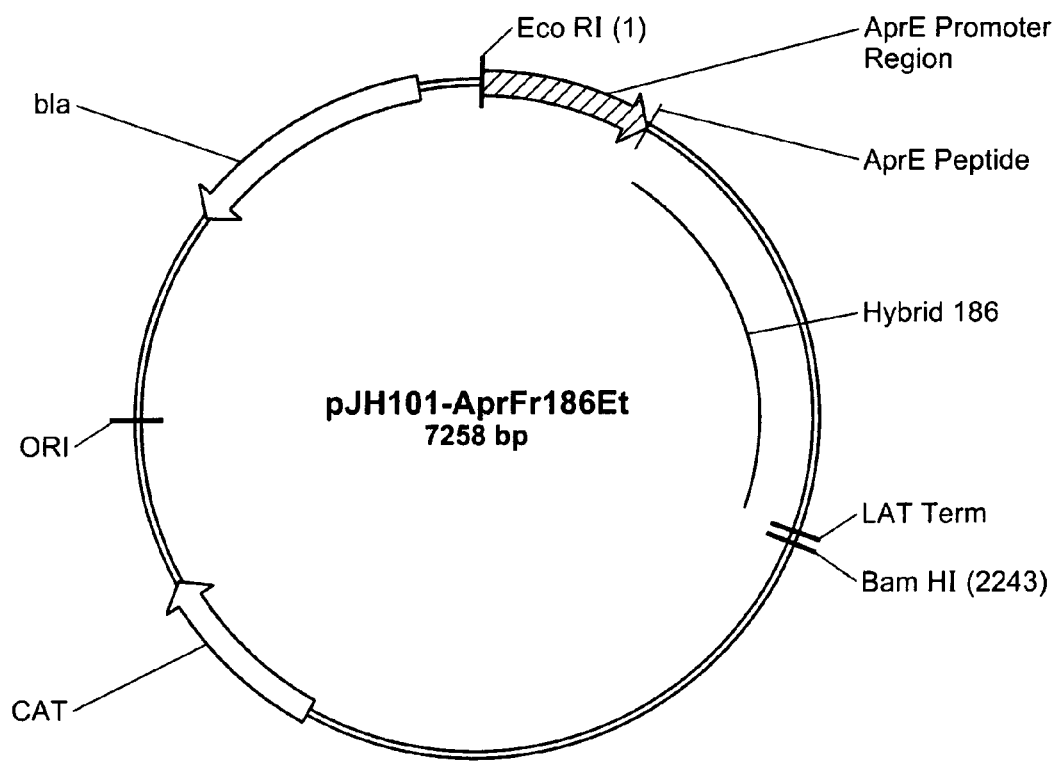
FIG. 1 is a diagram of the plasmid used for the expression of the various hybrids and amylases. The plasmid elements are as follows: Bla, the beta lactamase gene which codes for ampicillin/carbenicillin resistance marker; AprE promoter region, promoter from *B. subtilis* AprE (alkaline protease) having a region of homology to the *Bacillus* hosts' chromosome that allows it to integrate into the host genome; AprE peptide, the *B. subtilis* AprE signal sequence; Hybrid 186, the coding region for the gene of interest, such as hybrid 186; LAT Term, the native amylase LAT (licheniformis amylase thermostable) terminator from *B. licheniformis*; CAT, the chloramphenicol acetyl transferase gene for chloramphenicol antibiotic resistance; ORI, the origin of replication for *E. coli*. Note that this plasmid lacks an origin of replication for *Bacillus*.

Chimeric α-amylases are provided having beneficial advantages over currently available α-amylases. The chimeric α-amylases comprise an N-terminal portion from an AmyL amylase and a C-terminal portion from an AmyS amylase. The chimeric α-amylases exhibit improved thermostability relative to the AmyS enzymes, and improved specific activity or ability to reduce peak viscosity relative to the AmyL enzymes. Thus, these properties allow the chimeric polypeptides and thermostable amylases to be used in high-temperature starch liquefaction, for example for production of fermentation products such as alcohol, and especially ethanol. They result in reduced peak viscosity relative to AmyL amylases used alone, and low final viscosities relative to AmyS amylases used alone. The chimeric enzymes provided herein also useful in the breakdown or removal of starch, amylase, amylopectin, or other substrates of α-amylase in other high-temperature processes such as baking, as well as in the treatment of woven materials to remove starch-based sizing agents, or cleaning/washing processes. The chimeric enzymes provided herein can also be used in conjunction with each and or in conjunction with one or more other enzymes, for example in a blend. Preferably, other enzymes used are active under the same or similar reaction conditions as those used for the chimeric α-amylases. This provides more flexibility to the end user, as well as certain economic and processing advantages. Processing conditions, such as pH, temperature, ionic strength, as well as the presence of required cofactors, can be established to permit activity of the α-amylases and any other enzymes present. Such processing conditions can facilitate the use of continuous or semi-continuous processes, rather than costly and time-consuming batch processes. Other features provided in certain embodiments of the chimeric α-amylases are increased specific activity, and the ability to reduce the peak viscosity or the final viscosity of a starch slurry, as well as or better than either of the AmyL and AmyS enzymes.

A. Definitions & Abbreviations

In accordance with this detailed description, the following abbreviations and definitions apply. It should be noted that as used herein, the singular forms "a," "an," and "the" include plural referents unless the context clearly dictates otherwise. Thus, for example, reference to "an enzyme" includes a plurality of such enzymes, and reference to "the formulation" includes reference to one or more formulations and equivalents thereof known to those skilled in the art, and so forth.

The term "about" with respect to a numerical value or range indicates that the numerical value can be 10% greater or less than the stated value. In other embodiments, "about" indicates that a numerical value can be 5% greater or less than the stated value. The skilled artisan will appreciate that term "about," when used in conjunction with a number or range of amino acid residues or base pairs, or the length of a polypeptide in amino acid residues, or the length of a polynucleotide in base pairs, encompasses only integer values.

Unless defined otherwise, all technical and scientific terms used herein have the same meaning as commonly understood by one of ordinary skill in the art. The following terms are provided below.

1.1. Definitions

"Amylase" means an enzyme that is, among other things, capable of catalyzing the degradation of starch, amylose, amylopectin, and the like. Generally, α-amylases (EC 3.2.1.1; α-D-(1→4)-glucan glucanohydrolase) are defined as endo-acting enzymes cleaving α-D-(1→4) O-glycosidic linkages in a polysaccharide containing three or more α-D-(1→4) linked glucose units. The α-amylases release reducing groups in the α-configuration. They act on starch, glycogen and related poly- and oligosaccharides in a random manner. In contrast, the exo-acting amylolytic enzymes sequentially cleave the substrate molecule from the non-reducing end. The glucan 1,4-α-maltohydrolases (maltogenic α-amylases; EC 3.2.1.133) produce α-maltose as the end product, while β-amylases (EC 3.2.1.2) produce β-maltose. β-Amylases, α-glucosidases (EC 3.2.1.20; α-D-glucoside glucohydrolase), glucoamylase (EC 3.2.1.3; α-D-(1→4)-glucan glucohydrolase), and product-specific amylases can produce malto-oligosaccharides of a specific length from their respective substrates. Glucoamylases release glucosyl residues from the non-reducing ends of amylose and amylopectin molecules. Glucoamylases also catalyze the hydrolysis of α-1,6 and α-1,3 linkages, although at much slower rate than α-1,4 linkages.

A "chimeric polypeptide," or "chimera" means a protein containing sequences from more than one polypeptide. An chimeric polypeptide or α-amylase can be chimeric in the sense that it contains a portion, region, or domain from one molecule fused to one or more portions, regions, or domains from one or more other molecules. By way of example, a chimeric polypeptide or a chimeric α-amylase might comprise a sequence for a mature α-amylase protein linked to the sequence for the signal peptide of another α-amylase. The skilled artisan will appreciate that chimeric polypeptides and α-amylases need not consist of actual fusions of the protein sequences, but rather, polynucleotides with the corresponding encoding sequences can also be used to express chimeric polypeptides or α-amylases that comprise the same amino acid sequence as an actual or hypothetical fusion protein made from or ("derived from") other amylases. Thus, for example, a chimeric α-amylase or a chimeric polypeptide herein can comprise an amino-terminal portion of a first amylase and a carboxy-terminal portion of a second amylase, or the chimeric polypeptide or α-amylase could be expressed from a polynucleotide encoding a protein of the same sequence. In the case of a chimeric α-amylase, the catalytic activity of an α-amylase must be present in the resultant molecule. "Chimeric molecules" as used herein, can be either polynucleotides or polypeptides, and are not naturally occurring. A wild-type α-amylase occurs naturally. Chimeric amylases differ from a wild-type α-amylase in the amino acid residues of the mature protein, i.e., in the primary amino acid sequence of the active molecule without a signal sequence.

"Activity" with respect to enzymes means "catalytic activity" and encompasses any acceptable measure of enzyme activity, such as the rate of activity, the amount of activity, or the specific activity. Catalytic activity refers to the ability to catalyze a specific chemical reaction, such as the hydrolysis of a specific chemical bond. As the skilled artisan will appreciate, the catalytic activity of an enzyme only accelerates the rate of an otherwise slow chemical reaction. Because the enzyme only acts as a catalyst, it is neither produced nor consumed by the reaction itself. The skilled artisan will also appreciate that not all polypeptides have a catalytic activity. "Specific activity" is a measure of activity of an enzyme per unit of total protein or enzyme. Thus, specific activity may be expressed by unit weight (e.g. per gram, or per milligram) or unit volume (e.g. per ml) of enzyme. Further, specific activity may include a measure of purity of the enzyme, or can provide an indication of purity, for example, where a standard of activity is known, or available for comparison.

"Variants" refer to polypeptides and nucleic acids. The term "variant" may sometimes be used synonymously with the term "mutant." Variants include insertions, substitutions, deletions, transversions, truncations, and/or inversions at one or more locations in an amino acid or nucleotide sequence. Variant nucleic acids can include sequences that are complementary to sequences that are capable of hybridizing to the nucleotide sequences presented herein. For example, a variant sequence is complementary to sequences capable of hybridizing under stringent conditions, e.g., 50° C. and 0.2× SSC (1×SSC=0.15 M NaCl, 0.015 M sodium citrate, pH 7.0), to the nucleotide sequences presented herein. More particularly, the term variant encompasses sequences that are complementary to sequences that are capable of hybridizing under highly stringent conditions, e.g., 65° C. and 0.1×SSC, to the nucleotide sequences presented herein. In various embodiments, a variant is at least 60, 65, 70, 75, 80, 85, 90, 91, 92, 93, 94, 95, 96, 97, 98, or even 99% identical to a sequence expressly provided herein.

As used herein, the term "expression" refers to the process by which a polypeptide is produced based on the nucleic acid sequence of a gene or artificial sequence. The process includes both transcription and translation. "Expression product" refers generally to a protein made by translation, whether in vivo or in vitro. Similarly, if a gene is expressed, the gene product (usually protein, but sometimes RNA) is produced in a cell, such as a host cell comprising the gene.

"Microorganism" as used herein includes any bacterium, yeast, or fungus species.

"Isolated" with respect to protein, or nucleic acid sequences means that the sequence is at least substantially free from at least one other component that the sequence is naturally associated and found in nature. In the example of nucleic acid sequence, by isolated is meant isolated from genomic sequences.

"Purified" means that the material is in a relatively pure state, e.g., at least about 90% pure, at least about 95% pure, or at least about 98% pure. "Partially purified" encompasses lesser degrees of purity, provided that the protein or nucleic acid is "isolated" as used herein.

"Thermostable" means the enzyme retains measurable activity after exposure to elevated temperatures. One measure of the thermostability of an enzyme, such as an α-amylase, is its half-life ($t_{1/2}$), where half of the enzyme activity is lost by the half-life. The half-life value is calculated under defined conditions by measuring the residual amylase activity. In some embodiments, other measures of thermostability may be more useful or more practical, and may be measured and expressed, for example, as percent activity remaining after a specified exposure time at a temperature of interest. In another definition, thermostability is expressed as the melting temperature, or Tm, i.e. the midpoint of the transition from F<=>U in which F is folded protein and U is unfolded. Any mutation that causes an increase in Tm is said to be a stabilizing mutation. "Greater thermostability" or "enhanced thermostability" are used interchangeably herein. Any mutation that increases Tm or $t_{1/2}$ enhances thermostability of the associated polypeptide or enzyme. In some cases, rather than determine a Tm or $t_{1/2}$, other measures of stability are used. Tm cannot always be correctly determined because the transition from folded to unfolded may be irreversible. In such cases, stability can be defined as Tx, the temperature at which x percent protein remains functional after a specified time. If in a particular application it is known that an enzyme must remain active for about an hour, a useful comparison between enzymes may be a Tx for 60 minutes to ensure that an acceptable amount of activity remains after 60 minutes at a temperature at least that required in practice. Where irreversible denaturation is an issue, it is useful to assay under conditions similar to those in which the enzyme will be applied later, e.g. conditions of temperature, pH, or the presence of oxidants, detergents, or chelators must be considered.

Generally, after exposure of an enzyme to a temperature of interest for a desired time, the enzyme will be assayed under standard assay conditions, including temperature. Thermostable enzymes may also be thermoactive enzymes, i.e. they can exhibit activity when assayed at high temperatures. As used herein, thermostable enzymes can be both resistant to heat denaturation and active at high temperatures.

"Thermostable chimeric α-amylases" are chimeric α-amylases as defined herein with enhanced thermostability relative to at least one amylase from which the chimera is derived. The thermostable chimeric amylases preferably have a thermostability that is greater than that of the less thermostable amylase from which the chimera is derived, and about that of the more thermostable amylase from which the chimera is derived.

"pH range" means the ability of the enzyme to exhibit catalytic activity from acidic to basic conditions. Common processes in which α-amylases are used may include pH conditions spanning 5 or more pH units. As used herein, "pH stable" relates to the ability of the enzyme to retain measurable activity over a wide range of pHs, for example, 1, 2, 3, 4, 5, or even more pH units. In addition to pH stability, the chimeric α-amylases described herein may also provide a pH optimum, wherein activity is maximal at a certain pH or pH range, under conditions of temperature, time, substrate concentration, and calcium ion concentration that are otherwise held constant.

As used herein, "amino acid sequence" is sometimes used synonymously with the term "polypeptide" and/or the term "protein." In some instances, the term "amino acid sequence" is synonymous with the term "peptide"; in some instances, the term "amino acid sequence" is synonymous with the term "enzyme." In other cases, which will be clear from the context, the "amino acid sequence" will refer to the actual sequence ("primary sequence") of amino acid side chains or "residues" in the backbone of a polypeptide. For example, the Sequence Listing provided herewith provides the amino acid sequences for several polypeptides or domains of polypeptides.

As used herein, "nucleotide sequence" or "nucleic acid sequence" refers to an oligonucleotide sequence or polynucleotide sequence ("polynucleotide") and variants, homologues, fragments and derivatives thereof. The nucleotide sequence may be of genomic, synthetic or recombinant origin and may be double-stranded or single-stranded, whether representing the sense or anti-sense strand. As used herein, the term "nucleotide sequence" includes genomic DNA, cDNA, synthetic DNA, and RNA. As with polypeptides, the term "nucleotide sequence" is also used at times in discussion of the actual sequence of nucleotides or bases along a polynucleotide backbone, i.e. the primary sequence.

"Homologue" means an entity having a certain degree of identity or "homology" with the subject amino acid sequences and the subject nucleotide sequences. Typically, homologues will comprise the same active site residues as the subject amino acid sequence. Homologues also retain α-amylase activity, although the homologue may have different enzymatic properties than the subject protein. A "homologous sequence" includes a polynucleotide or a polypeptide having a certain percent identity, e.g., at least about 80%, 85%, 90%, 95%, or 99%, with another sequence.

"Percent identity" or "percent sequence identity" means that a given percentage of bases or amino acid residues in a subject sequence or protein are exactly the same base or residue as present in a reference sequence or protein, for example when comparing the two polypeptide sequences in an alignment. Amino acid sequences may be similar, but are not "identical" where an amino acid is substituted, deleted, or inserted in the subject sequence relative to the reference sequence. For proteins, the percent sequence identity is preferably measured between sequences that are in a similar state with respect to posttranslational modification. Typically, the "mature sequence" of the subject protein, i.e., that sequence which remains after processing to remove a signal sequence, is compared to a mature sequence of the reference protein. In other instances, a precursor sequence of a subject polypeptide sequence may be compared to the precursor of the reference sequence.

As used herein, "hybridization" includes the process by which a strand of nucleic acid joins with a complementary strand through base pairing, as well as the process of amplification as carried out in polymerase chain reaction (PCR) technologies. A nucleic acid encoding a chimeric α-amylase may exist as single- or double-stranded DNA or RNA, an RNA/DNA heteroduplex, or an RNA/DNA copolymer. As used herein, "copolymer" refers to a single nucleic acid strand that comprises both ribonucleotides and deoxyribonucleotides. The α-amylase encoding nucleic acid may be "optimized" to increase expression a specific organism by tailoring the nucleic acid to contain those codons which are preferentially utilized in translating native proteins in that organism.

As used herein, a "synthetic" compound is produced by chemical or enzymatic synthesis. Synthetic compounds include, but are not limited to, nucleic acids encoding chimeric α-amylases, preferably made with optimal codon usage for host organisms of choice for expression. A synthetic polypeptide or nucleic acid can also be prepared using in vitro techniques, such as in vitro transcription or translation, or PCR and the like.

As used herein, "transformed cell" includes cells, including both bacterial and fungal cells, that have been transformed by use of recombinant DNA techniques. Transformation typically occurs by insertion of one or more nucleotide sequences into a cell. The inserted nucleotide sequence may be a heterologous nucleotide sequence, i.e., is a sequence that is not naturally present in the cell that is to be transformed, such as a nucleic acid encoding a fusion protein or a chimeric polypeptide.

As used herein, "operably-linked" means that the described components are in a relationship permitting them to function in their intended manner. For example, a regulatory sequence can be "operably-linked" to a coding sequence in such a way that expression of the coding sequence is achieved under conditions compatible with the regulatory sequence.

As used herein, "biologically active" refers to a sequence having a similar structural, regulatory or biochemical function as the naturally occurring sequence, although not necessarily to the same degree. For example, a biologically active α-amylase is a polypeptide with measurable α-amylase activity.

"Genotoxic potential" as used herein refers to the potential for compounds, e.g. polypeptides, amylases or compositions comprising them, to be "genotoxic" in in vitro or in vivo studies. "Genotoxic" is a broad term that refers to any deleterious change in the genetic material regardless of the mechanism by which the change is induced. Genotoxic compounds, in the absence of other data, are generally presumed by regulatory bodies and researchers to be trans-species carcinogens, implying a hazard to humans. Accordingly, such compounds need not be subjected to long-term carcinogenicity studies. However, if such a compound is intended to be administered chronically to humans, a chronic toxicity study (up to 1 year) may be necessary to detect early tumorigenic effects. A test battery approach of in vitro and in vivo tests can be used to test for genotoxicity. The battery is preferably designed to reduce the risk of false negative results for compounds with genotoxic potential. Assessment of the genotoxic potential of a compound is preferably conducted as an independent, objective inquiry. Such an assessment preferably takes into account the totality of the findings and the intrinsic value and limitations of both the in vitro and in vivo tests. A single positive result in any assay for genotoxicity does not necessarily mean that the test compound poses a genotoxic hazard to humans. Genotoxic potential is preferably assessed in accordance with official guidelines, such as the "ICH Guideline on Specific Aspects of Regulatory Genotoxicity Tests". The guidance on genetic toxicity testing provided by FDA's Center for Food Safety and Applied Nutrition (58 FR 16536, Mar. 29, 1993) is also considered to be applicable for determination of genotoxic potential herein.

As used herein the term "starch" refers to any material comprised of the complex polysaccharide carbohydrates of plants. Starches generally comprise amylose and amylopectin with the formula $(C_6H_{10}O_5)_x$, wherein X can be any integer. The term "granular starch" refers to raw, i.e., uncooked starch, e.g., starch that has not been gelatinized. "Starch derivative" as used herein refers to any modified or derivatized starch, e.g. any starch altered by physical or chemical treatment to give altered properties for food processing or other use. Such changes can include altered gelling properties, flow properties of the dry starch or a slurry prepared therefrom, color, clarity, stability of a slurry or paste, and the like. For example, as used in confectionery products, acid-modified starch results from acid treatment that reduces the viscosity of a slurry or paste made therefrom. Chemical derivatives of starch, such as ethers and esters, show properties such as reduced gelatinization in hot water and greater stability to acids and alkalis ('inhibited' starch). Examples of starch derivatives include dextrin roasted starches, acid-treated starches, alkaline treated starches, bleached starch, oxidized starch, enzyme-treated starch, monostarch phosphate, distarch phosphate, phosphated distarch phosphate, acetylated distarch phosphate, starch acetate, acetylated distarch adipate, hydroxypropyl starch, hydroxypropyl distarch phosphate, and starch sodium octenylsuccinate, as well as various salts or esters, particularly fatty acid esters of the foregoing.

As used herein the term "saccharification" refers to enzymatic conversion of starch to glucose.

The term "liquefaction" refers to the stage in starch conversion in which gelatinized starch is hydrolyzed to give low molecular weight soluble dextrins. The term "degree of polymerization" (DP) refers to the number (n) of anhydroglucopyranose units in a given saccharide. Examples of DP1 are the monosaccharides glucose and fructose. Examples of DP2 are the disaccharides maltose and sucrose. A "comparable liquefaction process" as used herein refers to a control processed for liquefaction. The liquefaction processes are conducted under controlled conditions, e.g. the liquefaction process comprises specified conditions of temperature, pH, calcium ion concentration, and substrate concentration. Comparable liquefaction processes provide a means to compare different enzymes or enzyme blends in their ability to liquefy a starch by controlling for as much as possible except the differences in enzymes. As used herein "facilitating liquefaction" or "facilitating a liquefaction process" encompasses any degree of improvement in liquefaction of a starch slurry, such as making a liquefaction process more efficient, more effective, more economical, or easier (facile). The term includes reducing the number or amount of enzymes required, reducing the peak or final viscosity of the starch slurry, increasing the rate or extent of starch degradation, or the production of fragments of any particular DP, or of limit dextrins. Facilitating liquefaction also includes reducing the net energy requirements, improving the utilization of substrate, or improving other conditions such as the calcium ion concentration or tolerance of changes in calcium ion, ability to use different starch (i.e., substrate) sources, types, or concentrations, ability to operate at preferred pH levels or ranges, quantity and quality of the resultant product, and the like.

As used herein the term "dry solids content" (ds) refers to the total amount of solids in a slurry, on a dry weight basis. Dry solids content and dry weight basis are usually expressed as the weight of the subject material as a percentage of the weight of the total dry material. The term "slurry" refers to a mixture containing insoluble solids in a liquid, typically water or a similar solvent. Starch or flour is frequently suspended in a water-based solution to form a slurry for testing amylases, or for liquefaction processes.

The term "DE," or "dextrose equivalent," is defined as the percentage of reducing sugar as a fraction of total carbohydrate.

As used herein, the terms "fermentation" or "fermentation process" refer to the breakdown of organic substances and re-assembly into other substances, and as used here can encompass any process of "industrial fermentation," "biochemical fermentation," or "food fermentation." "Industrial fermentation" generally refers to highly oxygenated and aerobic growth conditions, whereas "biochemical fermentation" generally refers to a strictly anaerobic process. Carbohydrate substrates are required as a source of energy for the vast majority of industrial fermentation process to produce a variety of pharmaceuticals and precursors, as well as food ingredients. Where a fermentation is specified herein for use in the production of alcohol, e.g. ethanol, such as for fuel production, it is generally an oxygen-limited, oxygen-deprived, or even completely anaerobic process. Bio-fuels are fuels from renewable resources, for example ethanol derived from fermentation of a carbohydrate substrate. "Food fermentations" include fermentation processes to make alcoholic beverages (e.g. beer, wine), bread, and other fermented food products. Preferred food fermentations are those that result in the production of alcohol or food acids from carbohydrate substrates.

"Food processing aids" as used herein refers to substances used as manufacturing aids to enhance the appeal or utility of a food or food component, including clarifying agents, clouding agents, catalysts, flocculents, filter aids, and crystallization inhibitors, etc. Food processing aids are generally defined by regulatory bodies such as the Food and Drug Administration in the United States, Food Standards Australia New Zealand, or the Commission Regulation of the European Economic Community (EEC). See for example 21 C.F.R. §§170.3(o) "Definitions" describing the physical or technical functional effects for which direct human food ingredients may be added to foods in the United States. The definition provided therein, including those for "processing aids" are adopted from the National Academy of Sciences/National Research Council National Survey of Food Industries, reported to the Food and Drug Administration under the contract entitled "A Comprehensive Survey of Industry on the Use of Food Chemicals Generally Recognized as Safe" (September 1972), which is incorporated by reference in its entirety. Copies of that report are available from the National Technical Information Service (NTIS), 5285 Port Royal Rd., Springfield, Va. 22161, or at the National Archives and Records Administration (NARA).

As used herein, "stabilizing structures" refer to primary, secondary, tertiary, or quaternary structures that make a protein more stable, particularly more thermostable as defined hereinabove. Proteins are "stable" if under a given set of conditions they remain properly or adequately folded. Stabilizing structures in accordance herewith are formed by one or more stabilizing mutations. Some means of stabilizing proteins are not deemed "stabilizing structures" for purposes herein. Thus, basic ways of achieving improved stability are as diverse as using increased or decreased ion concentrations, inorganic solvents, using higher or lower protein concentrations, adding helper proteins, optimizing storage temperatures, or removing proteases from the medium. For example, calcium binding proteins and many enzymes that use calcium as a co-factor are normally more stable at higher calcium concentrations. For purposes herein, however, "stabilizing structures" do not encompass environmental factors and the like, but rather are chemical structures that lie within or result from the primary or higher order sequence, and alter the stability of the protein.

"Helix capping" is a stabilizing strategy that is known in the art and useful herein. "Helix-capping motifs" are stabilizing structures that comprise specific patterns of hydrogen bonding and hydrophobic interactions found at, or near, the ends of helices in proteins and peptides. The consensus sequence patterns of such motifs, together with results from simple molecular modeling, have been used to formulate useful rules of thumb for helix termination. See, e.g., Aurora and Rose, "Helix capping" *Protein Science,* 7(1):21-38 (1998, Cold Spring Harbor Laboratory Press). See also Presta and Rose, "Helix signals in proteins." *Science,* 240:1632-1641 (1988).

"Salt bridge," as used herein, refers to hydrogen bonds between oppositely-charged amino acid residues (e.g. Asp-Arg) in the primary sequence of a polypeptide. Salt bridges contribute to the stability of a protein when the charges are 6-8 Angstroms or less away from each other. Thus, the charged residues may be widely separated in the primary amino acid sequence provided that, when folded, the charged residues come within the required proximity for interaction of the charges. Salt bridges typically work better when combined with other salt bridges. Thus, an array of charge residues, e.g. +, −, +, −, works better than one or two pairs of charged residues that are remote from each other in the structure. For example, extremophilic proteins, i.e. proteins from extremophiles, such as thermostable proteins, often have many salt bridges. An introduced salt bridge works better if the residues involved have only limited freedom in the folded protein.

B. Abbreviations

The following abbreviations apply unless indicated otherwise:

AmyL *Bacillus licheniformis* α-amylase
Amy Q *Bacillus amyloliquefaciens* α-amylase
AmyS *Bacillus stearothermophilus* α-amylase
AAU alpha amylase units
ATCC American Type Culture Collection
cDNA complementary DNA
C.F.R. Code of Federal Regulations
CFU colony forming units
DE Dextrose Equivalent
DEAE diethylaminoethanol
DNA deoxyribonucleic acid
DNS 3,5-dinitrosalicylic acid
DPn degree of polymerization with n subunits
ds dry solids
EC Enzyme Commission for Enzyme Classification
EEC European Economic Community
EDTA ethylenediaminetetraacetic acid
EGTA ethyleneglycoltetraacetic acid
FDA Food & Drug Administration
FAO Food and Agriculture Organization of the United Nations
GLP Good Laboratory Practices
GMP Good Manufacturing Practices
GRAS Generally Recognized As Safe
HFCS high fructose corn syrup
HPLC High Performance Liquid Chromatography
HS higher sugars (DPn, where n>3)
JECFA Joint FAO/WHO Expert Committee on Food Additives
kb kilobase
kJ kiloJoule
LAT *B. licheniformis* α-amylase
LU liquefaction units
mRNA messenger ribonucleic acid
mg milligram
mL milliliter
mt metric ton (1000 kg)
N Normal
NTIS National Technical Information Service
PCR polymerase chain reaction
PEG polyethyleneglycol
ppm parts per million
RO Reverse osmosis
RT-PCR reverse transcriptase polymerase chain reaction
SB salt bridge
SDS-PAGE sodium dodecyl sulfate-polyacrylamide gel electrophoresis
SGA Superior Grain Amylase
SKBU/g ds α-Amylase Unit per gram of dry solids. One α-Amylase Unit dextrinizes 1.0 g of limit dextrin substrate per hour under the conditions of the assay.
1×SSC 0.15 M NaCl, 0.015 M sodium citrate, pH 7.0
WHO World Health Organization
w/v weight/volume
w/w weight/weight
μg microgram
μL microliter C. Chimeric α-amylases In a first of several aspects, chimeric polypeptides having a length of about 480-515 amino acid residues are provided. The chimeric polypeptides have an amino-terminal domain that comprises about 180 or more contiguous amino acid residues of an N-terminal portion of an AmyL amylase, and a carboxy-terminal domain comprises a carboxy-terminal portion of an AmyS amylase. The chimeric polypeptides do not have the primary amino acid sequence of either the AmyL amylase or the AmyS amylase, however, the chimeric polypeptides have enhanced thermostability relative at least to the AmyS amylase.

Known amylase sequences are not encompassed by the chimeric polypeptides or thermostable chimeric amylases described herein. For example the sequences disclosed in *J. Biochem. Mol. Biol.* 40: 315-324 (2006) by Sajedi et al. are specifically excluded. The α-amylase sequences provided in the public databases of the European Molecular Biology Laboratories (EMBL) or the National Center for Biotechnology Information (NCBI) more than one year prior to the filing date of this disclosure are also expressly excluded as sequences for the chimeric polypeptides and thermostable amylases provided herein. In one embodiment, the chimeric polypeptide or thermostable amylase does not have the sequence of any other known α-amylase, such as those disclosed in U.S. Pat. No. 6,939,703 by Van Der Laan and Aehle, U.S. Pat. No. 6,143,708 by Svendsen et al., or U.S. Pat. No. 5,830,837 by Bisgård-Frantzen et al. The chimeric polypeptides generally comprise the catalytic activity of an α-amylase. In common usage, alpha-amylase attacks the random alpha-1,4 linkages of a substrate such as amylose and/or amylopectin of starch, converting them to dextrins. In the process of doing so, the α-amylase reduces the viscosity and increases the dextrose equivalence (DE). The alpha-amylase enzyme is thus frequently used to liquefy and dextrinize starch, typically in slurries for the production of syrups or prior to fermentation of complex carbohydrates. They are also used for starch removal, e.g. cleaning processes, as well as in baking and other applications.

The chimeric polypeptides demonstrate altered performance characteristics relative to other α-amylases such as AmyL or AmyS. Such characteristics may include altered stability, pH range, oxidation stability, and thermostability. In particular, in various embodiments, the chimeric polypeptides provide better stability at high temperatures (i.e., 70-120° C.). They may also have advantageous properties in their requirement for calcium, resistance to changes in calcium ion concentration, and/or increased tolerance to pH extremes (i.e., pH 4.0 to 6.0, or pH 8.0 to 11.0) for activity.

Many known thermostable amylases can degrade starch at temperatures of about 55° C. to about 80° C. or more. A chimeric polypeptide as provided herein may retain α-amylase activity after exposure to temperatures of up to about 95° C. or more. Thus, the chimeric polypeptides and thermostable chimeric amylases as provided herein are advantageous for use high temperature liquefaction, as well as in other processes that employ or require elevated temperatures, such as cooking, baking or the like.

In one embodiment, the chimeric polypeptides comprise at least one substituted amino acid residue in the N-terminal domain, relative to the AmyL amylase, i.e. the portion of the chimera that corresponds to the contiguous amino acids of the chimera's N-terminal portion has a substitution relative to the sequence found in the AmyL amylase's N-terminal portion. Such a substitution preferably serves to provide a stabilizing structure, or at least a part of a stabilizing structure that enhances thermostability of the polypeptide. Various stabilizing structures may be known to those of skill in the art generally with respect to thermostability of proteins. Any such structures will suffice in various embodiments of the chimeric polypeptide. As defined above, "stabilizing structures" are primary, secondary, tertiary, or quaternary structures that make a protein more stable, particularly more thermostable as defined hereinabove.

Stabilizing structures in accordance herewith are formed by one or more stabilizing mutations that form chemical structures that lie within, or result from, the primary or higher order sequence, and alter the stability of the protein.

Proteins transition between folded and unfolded states. Stabilizing structures shift the equilibrium between folded and unfolded proteins towards the folded state (i.e., towards the left in the equilibrium: folded protein< - - - >unfolded protein). It is known in the art how to shift this equilibrium further to the left, i.e. to make a protein more stable. Modifications that destabilize the unfolded form and/or stabilize the folded form are equally desirable as stabilizing structures. Methods for determining what structures will be stabilizing in a particular protein are known in the art. One approach to adding stabilizing structure include the use of amino acid residues that more stable members of the same protein family already use at that position. Thus, study of multiple sequence alignments of proteins from different origins is useful.

Helix capping, as defined above is one strategy for generating stabilizing structures that is known in the art and useful herein. Helix-capping motifs are stabilizing structures that comprise specific patterns of hydrogen bonding and hydrophobic interactions found at, or near, the ends of helices in proteins and peptides. Helix capping has been considered a bridge linking the conformation of secondary structure to super-secondary structure. In an α-helix, the first four >N—H groups and last four >C═O groups necessarily lack intrahelical hydrogen bonds. Instead, such groups are often capped by alternative hydrogen bond partners. Distinct capping motifs have been identified, some at the helix N-terminus and others at the C-terminus. The consensus sequence patterns of such motifs, together with results from simple molecular modeling, have been used to formulate useful rules of thumb for helix termination. See, e.g., Aurora and Rose, "Helix capping" *Protein Science,* 7(1):21-38 (1998, Cold Spring Harbor Laboratory Press). See also Presta and Rose, "Helix signals in proteins." *Science,* 240:1632-1641 (1988).

Increasing entropic stabilization (e.g. by substituting Gly->X, or X->Pro, where X is any amino acid residue) is another strategy for generating stabilizing structures. Other strategies include adding one or more disulphide bridges, filling cavities within the three-dimensional structure, especially when combined with entropic stabilization, e.g. Gly->Ala, adding one or more salt bridges, particularly surface salt bridges, eliminating buried water molecules (e.g. substituting Ala->Ser), improving hydrogen bonding, improving helix structure (e.g. "helix propensity") in helical portions or domains, improving strand structure (e.g. "strand propensity") in domains that form strands. Preferably, stabilizing structures are introduced through substitution or mutation of one or more surface amino acid residues, however, substitution or mutation of amino acid residues buried within a higher level protein structure, or in the interior of a folded protein can also be useful for stabilizing. Stabilizing structures such as those described above and others known in the art can be incorporated rationally into known protein sequences using one or more stabilizing point mutations ("stabilizing mutations").

Stabilizing structures in general provide a decrease in the Gibbs free energy (ΔG) of the folded protein relative to the unfolded protein (thereby shifting the thermodynamic equilibrium between folded and unfolded protein towards the folded form). Stabilizing structures herein also provide energy to the structure, or require a certain amount of energy to break. For example, entropic stabilization requires about 2-5 kJ/M to disrupt, while helix capping requires a range of about 1-8 kJ/M (average of about 4 kJ/M). Hydrogen bonds provide 1-6 kJ/M, hydrophobic interaction provide a gain of about 100 J/M for each square Angstrom of such interaction. A salt bridge can provide up to 5 kJ/M, and a cysteine bridge (i.e. disulfide bridge) provides −10 to 10 kJ/M.

In one embodiment, the stabilizing structure is a salt bridge formed, at least in part, by the substituted amino acid residue. As defined herein, salt bridges comprise hydrogen bonds between oppositely-charged amino acid residues in the primary sequence of a polypeptide. Salt bridges with residue charges that are 6-8 Angstroms, or less, away from each other in a folded polypeptide, are preferred herein. Thus, the charged residues may be widely separated in the primary amino acid sequence provided that, when folded, the charged residues come within the required proximity for interaction of the charges. Salt bridges work better in combination with other salt bridges. Arrays of charged residue, e.g. +, −, +, −, work better than only one or two pairs of charged that are remote from each other in the structure. Preferably therefore, more than one salt bridge is introduced. Some polypeptides and amylases provided in accordance herewith have many salt bridges. In one embodiment the amino acid residues involved introduced salt bridge have only limited freedom in the folded protein.

The substituted amino acid residue corresponds to position 187 in the AmyL amylase, in one embodiment. In certain embodiments, an Asp and a Thr residue are substituted in the chimeric polypeptide for consecutive Ser residues (i.e., Ser Ser) in the AmyL amylase (Asp 190 and Thr 191 are the cognate positions in AmyS). Surprisingly, it was found that such substitutions, e.g. S 187D-S 188T, substantially increase the thermostability of the chimeric polypeptides in the context of the AmyL-AmyS hybrids or chimeras as provided herein. As discussed more fully in the working examples provided herewith, other researchers have previously reported that any S 187D substitution in other contexts (e.g. in an AmyL-type sequence) results in a loss of, or decrease in, thermostability. Other substitutions, such as other acidic residues may be substituted in the chimera for other residues naturally present in a particular AmyL amylase. In one embodiment, the AmyL amylase on which the N-terminal contiguous amino acids are based has the amino acid sequence of SEQ ID NO: 1. The AmyS amylase has the amino acid sequence of SEQ ID NO: 2 in other embodiments. In presently preferred embodiments, the AmyL and AmyS have the sequences provided as SEQ ID NOs: 1 and 2, respectively.

The chimeric polypeptides provided herein have, in various embodiments, at least about 95% sequence identity to any of SEQ ID NOS: 1-17. Notwithstanding the sequence identity, the skilled artisan will appreciate that the chimeric polypeptides provided in accordance herewith may not have the precise or exact amino acid sequence of SEQ ID NO: 1 or 2. In one embodiment, the chimeric polypeptide has at least about 95% sequence identity to one of SEQ ID NOs: 1-17, and specifically has an Asp residue substituted in the chimeric polypeptide for a Ser reside at position 187 in the AmyL amylase (numbering corresponding to amino acid sequence in AmyL).

As discussed above, the chimeric polypeptides provided herein preferably comprise the catalytic activity of an α-amylase. The amylase preferably retains at least about 50% of its activity after incubation at 95° C. for about 20, 30, 40, 50, or 60 or more minutes. In one embodiment, the chimeric polypeptide has an amylase activity that retains at least about 50%, 60%, 65%, 70%, 75%, 80%, 85% or more of its activity after incubation at 95° C. for about 60 minutes, or even at least about 80% of its activity after incubation at 95° C. for about 60, 65, or 70 minutes, or even about 75, 80, 85 or more minutes. In one embodiment, a decrease in activity, if any, is not greater than the corresponding decrease in an AmyL amylase from which the chimeric sequence was obtained in part, even after incubation for 90 or more minutes at 95° C. Thus, in some embodiments, there is no significant or measurable loss in activity for that time period.

In one embodiment, the chimeric polypeptides provided comprises a catalytic activity of an α-amylase that has greater specific activity than the AmyL amylase from which the amino-terminal portion was derived, at least in part.

In another aspect, provided herein are thermostable chimeric α-amylases. The chimeric amylases have many properties in common with the chimeric polypeptides provided above. The thermostable chimeric amylases have an N-terminal portion comprising a contiguous amino acid sequence from an N-terminal portion of an AmyL amylase, and a C-terminal portion comprising a contiguous amino acid sequence from a C-terminal portion of an AmyS amylase. The thermostable chimeric amylases have a specific activity greater than the AmyL amylase and greater thermostability at 95° C. than the AmyS amylase. The thermostable amylases have a primary amino acid sequence that is about 475-520 residues long.

The thermostable chimeric amylases provide a number of applied benefits, or performance benefits. For example, in one embodiment, the thermostable amylases are characterized in that when used in a liquefaction process for a starch slurry, the chimeric amylases reduce peak viscosity of the starch slurry as well as the AmyS amylase does in a comparable liquefaction process. The thermostable chimeric amylases also reduce final viscosity of the starch slurry as well as the AmyL amylase does in a comparable liquefaction process. For purposes herein, a "comparable liquefaction process" means that the processes are conducted under controlled conditions, e.g., the liquefaction process comprises specified conditions of temperature, pH, calcium ion concentration, and substrate concentration.

The thermostability is frequently expressed herein as the amount time that the amylase retains activity after incubation at 95° C. In one embodiment, the chimeric amylase retains at least 50% of its activity after incubation at 95° C. for about 30, 40, 50 or even 60 or more minutes. In another, it retains at least about 60, 70 or even 80% of its activity after incubation at 95° C. for about 60 or more minutes.

In one embodiment, the Amy L amylase has the sequence of SEQ ID NO: 1 and the AmyS amylase has the sequence of SEQ ID NO: 2. The chimeric amylase has at least about 95% sequence identity to any of SEQ ID NOS: 1-17, but is not the amylase of SEQ ID NO: 1 or 2, as described above for the chimeric polypeptides.

The chimeric amylases further comprise at least one substituted amino acid residue in the N-terminal domain, relative to the AmyL amylase, so as to provide at least a part of a stabilizing structure that enhances thermostability of the polypeptide. Stabilizing structures are discussed for chimeric polypeptides and that discussion applies equally to thermostable chimeric amylases. The stabilizing structure is preferably a salt bridge formed, at least in part, by the substituted amino acid residue, also as discussed above. As with the chimeric polypeptides, the substituted amino acid residues correspond to one or both of positions 187 and 188 in the AmyL or AmyS amylase, and more particularly comprise one Asp residue and/or one Thr residue substituted in the chimeric polypeptide for one Ser residue, or if both an Asp and a Thr residue, for two consecutive Ser residues in the AmyL amylase.

D. Compositions Comprising Chimeric α Amylases

Also provided are a variety of compositions comprises one or more chimeric polypeptides having the catalytic activity of an α-amylase, or thermostable chimeric amylases. The compositions include for example, enzyme concentrates, enzyme blends, purified enzymes, partially purified enzyme products, food additives, and cleaning products containing the chimeric α-amylase.

Such compositions have a variety of uses. The compositions can also provide more than one chimeric polypeptide or amylase, or other amylases, or a combination thereof. The compositions can be highly purified or only partially purified. They are standardized in terms of units of activity in certain embodiments. The compositions can be provided in a variety of physical forms including liquids of various concentrations and purity, gels, cakes, semisolids, or solids. The compositions are amenable to any physical form provided that measurable activity remains in the final composition. Thus, the compositions can be conveniently lyophilized, concentrated, frozen, spray-dried, or otherwise processed in a variety of known or useful manners. The compositions can be provided in standard sizes for certain commercial applications, or custom packaged.

In one embodiment, the composition includes a chimeric amylase as described or exemplified herein. Provided are particular compositions comprising one or more of:

(a) a chimeric polypeptide, such as that described above, having a length of about 480-515 amino acid residues, and having an amino-terminal domain comprising about 180 or more contiguous amino acid residues of an N-terminal portion of an AmyL amylase, and a carboxy-terminal domain comprising a carboxy-terminal portion of an AmyS amylase, the chimeric polypeptide having enhanced thermostability relative at least to the AmyS amylase, (b) a thermostable chimeric α-amylase about 475-520 amino acid residues long, having an N-terminal portion comprising a contiguous amino acid sequence from an N-terminal portion of an AmyL amylase, and a C-terminal portion comprising a contiguous amino acid sequence from a C-terminal portion of an AmyS amylase, the chimeric α-amylase having a specific activity greater than the AmyL amylase and also having greater thermostability at 95° C. than the AmyS amylase; and (c) any combination of (a) a chimeric polypeptide and (b) a thermostable chimeric amylase.

The compositions may further comprise one or more additional polypeptides. The skilled artisan will appreciate the one or more additional polypeptides can comprise any known enzyme activity. Thus, any of a variety of additional enzymes can be added to provide further utility or convenience to the compositions. In various embodiments, the additional enzyme can comprise one or more of bacterial (β-amylases, e.g., BBA, fungal α-amylases, e.g., Clarase® L, or glucoamylase, isoamylases, isomerases, proteases, such as fungal and bacterial proteases, cellulases, lignases, hemicellulases, lipases, phospholipases, and cutinases. Compositions comprising one or more chimeric α-amylases as disclosed herein, together with a combination of any one or more of the foregoing, are contemplated for use herein. As disclosed above, fungal proteases include, for example, any protein-degrading enzyme activities obtained from *Aspergillus* spp., such as *A. niger, A. awamori, A. oryzae; Mucor* spp., e.g., M miehei; *Rhizopus* spp., and the like. β-amylases (EC 3.2.1.2) are exo-acting maltogenic amylases, which catalyze the hydrolysis of 1,4-α-glucosidic linkages into amylopectin and related glucose polymers, thereby releasing maltose. β-amylases have been isolated from various plants and microorganisms. See Fogarty et al., in PROGRESS IN INDUSTRIAL MICROBIOLOGY, Vol. 15, pp. 112-115 (1979). These β-amylases have optimum temperatures in the range from 40° C. to 65° C. and optimum pH in the range from about 4.5 to about 7.0. Contemplated β-amylases include, but are not limited to, β-amylases from barley Spezyme® BBA 1500, Spezyme® DBA, Optimalt™ ME, Optimalt™ BBA (Genencor International, Inc.); and Novozym™ WBA (Novozymes A/S).

The compositions in one embodiment are prepared or formulated for use as a food additive or as a processing aid suitable for use in food processes. A food-grade lyophilized composition comprising a chimeric polypeptide or thermostable chimeric amylase as disclosed herein is also provided. Such compositions are useful for cooking and baking applications, as well as any high-temperature applications where starch properties need to be altered, in terms of DP.

When prepared or formulated for use as a food additive or for use in food processes, the compositions must meet or exceed certain regulatory requirements. These requirements serve as a guide to the skilled artisan in preparing the compositions. Accordingly, the skilled artisan will appreciate that although the regulatory requirements may differ in various countries, generally the composition will be very low in heavy metal content, as well as low in lead and arsenic. Specifically, the total heavy metal content is preferably does not exceed about 40 ppm, and more preferably is less than about 30 ppm. The lead content of the compositions does not exceed about 10 ppm, and more preferably is less than about 5 or 3 ppm. The arsenic content of the composition is less than about 3 ppm. The compositions are also negative for mycotoxin and antibacterial content, when tested be standard methods.

The compositions are also clean with respect to their microbiological content, preferably being produced under GMP or GLP standards at a minimum when intended for food additive use or as food processing aids. In particular, the total viable count will not exceed about $5 \times 10^4$ CFU per gram of composition. The compositions will preferably have a coliform count that does not exceed about 40 CFU per gram of composition. More preferably the count of coliforms will not exceed about 30 CFU per gram. Further, the compositions have no detectable *Salmonella* or *Shigella*, as measured by standard microbiological methods. Where the chimeric amylases are produced in host cell, the compositions will have less than 1 CFU of the organism per gram.

Further, the compositions possess a satisfactory standard of safety in terms of toxicity and the like. In one embodiment, the compositions show no genotoxic potential in suitable in vitro assays. The compositions also show no toxic effects in acute and/or sub-chronic dosing studies in animals.

For purposes of food additive or food processing aids, the production is preferably standard, as for many commercially used food enzymes. Thus, GMPs are used throughout the production process, meeting the requirements and specifications for food enzymes established for example, by the FDA, or international authorities, e.g., Food Chemicals Codex ($4^{th}$ Edition, 1996), the Joint FAO/WHO Expert Committee on Food Additives (JECFA) in the Compendium of Food Additives Specifications, Vol. 1, Annex 1 Addendum 9 (2001) (and earlier relevant Addenda). For example, the compositions comprising the chimeric α-amylase are produced using a process such as a fed-batch fermentation, e.g. a submerged fed-batch fermentation in an organism that is generally recognized as safe, or which has a long history of use for such purposes, for example for the production of food-grade enzyme preparations.

For some purposes herein, suitable organisms include Gram-positive bacteria from the genus *Bacillus* including, for example, *B. stearothermophilus, B. subtilis, B. licheniformis, B. brevis,* and *B. amyloliquefaciens.* Others including *B. coagulans, B. circulans, B. lautus, B. lentus, B. thuringiensis,* and *B. alkalophilus* may also be useful. Other Gram-positive bacteria that may be useful for production of some of the compositions described herein include *Streptomyces lividans,* and *S. murinus.* Gram-negative bacteria, including *Escherichia coli* or a *Pseudomonas* species, may also be used to produce certain of the compositions provided herein.

Also provided herein are compositions comprising chimeric polypeptides and thermostable chimeric α-amylases that are useful to facilitate removal of a substrate for the enzyme (e.g. starch) from a variety of nonstarch (thus, non-substrate) materials, such as textiles, paper, glass, plastic, metal, canvas, porcelain, and the like. Because such materials are frequently removed during washing or cleaning processes, the compositions in one embodiment includes one or more soaps, detergents, cleaning agents, oxidants, or chelators. In one embodiment, the composition is a used a laundry detergent, in another it is a dishwashing detergent. The compositions, for these and other purposes described herein, may be formulated as gels. A variety of such gels are known in the art and provide certain advantages, for example, with respect to contact time and conditions for the enzyme to work on the substrate to be removed, in addition to an appealing and convenient usage form for consumers or users. The inclusion of standard cleaning agents, as well as detergents, soaps, oxidants, and/or chelators requires that the α-amylase activity be somewhat tolerant of the conditions found not only in the end-use, and preferably in the more concentrated or extreme conditions found in the product itself.

E. Characterization of the Chimeric Amylases

Proteins and enzymes such as the chimeric polypeptides and thermostable α-amylases provided herein can be characterized by a variety of methods and techniques known in the art. The nucleic acid and primary polypeptide sequences are useful means of comparing and analyzing the amylases provided herein. Three dimensional structural modeling, and/or physical crystallization are also useful. Determination of specific activity is frequently used characterize enzymes.

Enzyme activity under a variety of conditions of substrate, temperature, pH, calcium concentration, and other factors can be assessed using standard assays known to the artisan skilled in this field, or by designing new assays based on known techniques of assaying amylases. Determining kinetic properties of the enzyme, including kinetic constants, such as $V_{max}$ or $K_m$ under specified conditions, is also useful for characterizing the chimeric amylases provided herein. Methods for determining the optimal pH for stability or for assay are known in the art, as are methods for determining the optimal calcium ion concentration for maximum activity and conditions for maximal stability during storage of the chimeric polypeptides and thermostable amylases.

Characterizing expression of the chimeric polypeptides and thermostable α-amylases in a host cell can be a useful characteristic, for example in determining the commercial potential of a process of making the chimeric proteins and enzymes. To evaluate the expression of the chimeric polypeptides and thermostable chimeric α-amylases in a host cell, one can measure the amount of expressed protein, the presence or amount of corresponding mRNA, or the enzyme activity (e.g., by monitoring conversion of a substrate to a product). Suitable assays include Northern and Southern blotting, RT-PCR (reverse transcriptase polymerase chain reaction), and in situ hybridization, using an appropriately labeled hybridizing probe. Measurements of the amount of expression of the chimeric polypeptides and thermostable chimeric α-amylases produced in a particular host cell, the rate of expression, or the maximal recovery are all examples of useful characteristics related to expression of the chimeric polypeptides and thermostable chimeric α-amylases provided herein.

Because the chimeric polypeptides and thermostable chimeric α-amylases have altered properties with respect to thermostability and specific activity, in certain embodiments they also have altered stability to oxidants, detergents, or chelators, in comparison to an α-amylase, such as an AmyL or AmyS enzyme. Thus, it may be useful to test the chimeric polypeptides and thermostable chimeric α-amylases that also provide such properties to find more useful α-amylases. For example, increased stability to oxidants, detergents, chelating agents, or even soaps, may be advantageous in compositions for cleaning processes, such as washing, dishwashing, textile desizing, or stain removal. The skilled artisan will appreciate that characterization of enzymes with respect to their stability or tolerance of cleaning agent, e.g. detergents, oxidants, chelators, or soaps, can be done by either exposing the polypeptide to the desired condition, including the cleaning agent, then assaying the activity under standard conditions, or by assaying the activity under the desired condition, including the cleaning agent. The former provides information about the stability of the polypeptide to the harsh conditions. The latter provides information about the ability of the enzyme to have catalytic activity under the harsh conditions.

The chimeric polypeptides and thermostable chimeric α-amylases described herein can also exhibit extended half-life at a given temperature, relative to the AmyS or AmyL enzymes. In various embodiments, half-life can be increased by about 10%, 20%, 30%, 40%, 50%, 60%, 70%, 80%, 90%, 100%, 200%, or more, particularly at elevated temperatures of about 55° C. to about 95° C. or more, particularly at about 80° C. or above. As described hereinabove, chimeric polypeptides and thermostable amylases with enhanced stability at 95° C. or above, relative to the α-amylases from which the chimera is derived, particularly the AmyS, are particularly useful.

In one embodiment, the chimeric polypeptides and thermostable chimeric α-amylases provided herein have the same pH stability as an amylase from which the chimera is derived, such as an AmyL-type or AmyS-type amylase. In another aspect, the chimeric polypeptides and thermostable amylases exhibit a greater range of stability to pH changes, or pH optimum or stable ranges are shifted to a desired area for the end commercial purpose of the enzyme. For example, in one embodiment, the chimeric polypeptides and thermostable amylases can degrade starch at about pH 4.5 to about pH 10.5. The chimeric polypeptides and thermostable amylases may have a longer half-life or higher activity (depending on the assay) relative to AmyL or AmyS under identical conditions. The chimeric α-amylase polypeptide also may have about 10%, 20%, 30%, 40%, 50%, 60%, 70%, 80%, 90%, 100%, 200% or longer half-life under identical pH conditions. In another embodiment, the chimeric α-amylase may have higher specific activity, as compared to an AmyL or AmyS, under identical pH conditions. The chimeric polypeptides and α-amylases provided may have any combination of desirable characteristics listed herein.

F. Polynucleotides Encoding the Chimeric α-amylases

In another of it several aspects, provided are polynucleotides that encode a chimeric polypeptide as described herein. Because the encoded polypeptides are not found in nature, the polypeptides must be made by the hand of man, e.g. synthesized or perhaps created through a directed mutagenesis and screening program. Specifically, the polynucleotides encode either of:

(a) a chimeric polypeptide having a length of about 480-515 amino acid residues, and having an amino-terminal domain comprising about 180 or more contiguous amino acid residues of an N-terminal portion of an AmyL amylase, and a carboxy-terminal domain comprising a carboxy-terminal portion of an AmyS amylase; the chimeric polypeptide having enhanced thermostability relative at least to the AmyS amylase, or (b) a thermostable chimeric α-amylase about 475-520 amino acid residues long, and having an N-terminal portion comprising a contiguous amino acid sequence from an N-terminal portion of an AmyL amylase, and a C-terminal portion comprising a contiguous amino acid sequence from a C-terminal portion of an AmyS amylase, said chimeric α-amylase having a specific activity greater than the AmyL amylase, and greater thermostability at 95° C. than the AmyS amylase.

In one embodiment, the polynucleotide encodes a polypeptide having at least about 95% sequence identity to any of SEQ ID NOS: 1-17. In various embodiments, the encoded polypeptide has at least about 90, 91, 92, 93, 94, 95, 96, 97, 98, or 99% sequence identity to any of SEQ ID NOS: 1-17; however, the polypeptide does not have the exact sequence of SEQ ID NOS: 1 or 2.

Presently preferred polynucleotides are exemplified in the sequence listing as SEQ ID NOS: 18-34, encoding, respectively, the polypeptides having amino acid sequences of SEQ ID NOS: 1-17. As the skilled artisan will appreciate, considerable variation among polynucleotides is possible without significant changes to an encoded amino acid sequence. In particular, substantial codon variation is possible because of redundancy in the genetic code (e.g. "wobble"), and because of codon usage preferences among different organisms. Accordingly, in various embodiments, the polynucleotides useful herein have sequences that are 60% or more identical to the polynucleotides of SEQ ID NOS: 18-34. More preferred are polynucleotides having sequences with 65, 70, 75, or 80% sequence identity to SEQ ID NOS: 18-34. Polynucleotides with greater than 80% identity, for example, 85, or 90% identity are also preferred for use herein. Similarly, polynucleotides with at least about 90, 91, 92, 93, 94, 95, 96, 97, 98, or 99% sequence identity to any of SEQ ID NOS: 18-34 are also useful herein. The foregoing discussion for all of the polynucleotides is subject to the proviso that in no case should an encoded polypeptide have the exact sequence of SEQ ID NOS: 1 or 2, nor should the polynucleotide have 100% sequence identity with either of SEQ ID NO: 18 or 19. The skilled artisan will appreciate that for use in the construction or making of the novel chimeric amylases, polynucleotides having sequences 100% identical to SEQ ID NO: 18 and 19 may be useful, as may polynucleotides encoding an amino acid sequence that is SEQ ID NO: 1 or 2, however, these polynucleotides do not encoded a novel chimeric amylase for purposes herein.

In one embodiment, the polynucleotide is a genomic DNA, while in another embodiment, the polynucleotide is a cDNA. Due to the degeneracy of the genetic code, there are multiple polynucleotides provided in accordance with this disclosure that can encode the same polypeptide. Polynucleotides also include mRNAs that encode a chimeric polypeptide or thermostable α-amylase as provided herein.

In one presently preferred embodiment, the polynucleotide encoding the chimeric polypeptide or α-amylase is optimized for expression of the chimeric polypeptide in a host cell from a microorganism or a plant by adapting the polynucleotide compositions to favor the those codons used preferentially in the host cell. Techniques for optimizing codon usage are known in the art. Codon usage tables for various organisms are available in standard resources such as texts or practice manuals for biotechnology.

Also provided are vectors comprising the polynucleotides encoding the chimeric polypeptides and α-amylases. Any vector for maintaining a polynucleotide, producing quantities of a polynucleotide, manipulating a polynucleotide sequence, or for expressing a polynucleotide in vitro or in a host cell is contemplated for use herein. Examples of suitable vectors are provided in standard biotechnology manuals and texts, e.g., Sambrook et al., MOLECULAR CLONING: A LABORATORY MANUAL, $3^{rd}$ ed., Cold Spring Harbor Laboratory Press, Cold Spring Harbor, N.Y. (2001).

In one embodiment, preferred vectors are useful for expression of the encoded polypeptide in a host cell, especially in a microbial cell, such as a bacterial cell, or in a plant cell. Expression vectors may be adapted for transient expression of the chimeric α-amylases, for example, to confirm catalytic and other properties prior to scaling up. Expression vectors for long-term use, and large-scale production are preferably adapted for stable expression, for example by integration into the host cell chromosome, or by stable incorporation of a self-replicating polynucleotide sequence. In one embodiment, the vector, a DNA construct is transferred to a host cell by an expression vector that comprises regulatory sequences operably-linked to a coding sequence for the chimeric polypeptide or chimeric α amylase.

Presently preferred vectors include pBR322, and pUC vectors, such as pUC 18, and particularly modifications and derivatives thereof. Such vectors are generally well-known vectors adapted for use in microbial systems. In one embodiment, the vector is a pJH101t, a pBR322 derivative that is adapted for integrating into B. subtilis, and which contains the multicloning site from pUC18, and several useful Bacillus sequences. See e.g. Ferrari et al., J. Bacteriology, 154:1513-1515, incorporated herein by reference for all purposes. Use of the pJH101t vector in construction of hybrids expressing the chimeric amylases is exemplified herein (see Methods, under Examples, below). Modification of the vector backbone can be used to facilitate site-directed mutagenesis, for example to produce chimeras featuring salt bridges or the like.

Provided also are microbial cells, including yeast, fungi, or bacterial cells, comprising the vector comprising the polynucleotide that encodes the chimeric polypeptides or α-amylases. In one embodiment, the vector is an expression vector suitable for expression of the encoded polypeptide in the host cell. In another embodiment, a plant cell is provided, said cell comprising a plant expression vector. Vectors for expression in various host cells are known in the art and such vectors, it will be appreciated contain required regulatory sequences, such as promoters and the like, to facilitate expression of the encoded polynucleotide. Exemplary promoters for use in Bacillus include the promoters from the amylase genes in AmyL, AmyQ, AmyM, or AmyS, as well as the promoters from xylA and xylB genes in B. subtilis. In one embodiment, the expression vector contains one or more strong promoters, either constitutive or inducible for expressing or over-expressing the encoded polypeptide. In another embodiment, the polynucleotide includes sequences for post-translational modification of the peptide, such as transporting the expressed polypeptide out of the cell, or to a specific compartment within the host cell, to facilitate production, isolation, or purification of the polypeptide from the host cell. For example, the polynucleotides can include one or more sequences such that the chimeric polypeptide or α-amylase is initially produced with a heterologous polypeptide attached to one end, such as a signal peptide from B. licheniformis to promote secretion of the expressed protein from a bacterial host cell. The polynucleotide may also include sequences such that the chimeric amylase is initially produced with a "purification sequence," i.e., a sequence to facilitate purification of the expressed protein, wherein the "purification sequence" is cleaved or removed during purification.

Where the host cell is a plant, it is contemplated that in one embodiment the plant is a crop plant that is used for starch production. The chimeric polypeptides or α-amylases can be overproduced in the plant. The chimeric polypeptide or amylase can be overproduced and compartmentalized with that part of the plant used for starch storage, e.g., the seed. Thus, the plant can be harvested, the starch can be isolated and the chimeric α-amylase activity will be co-purified with the starch. This embodiment is particularly useful where the plant is used for alcohol fermentation, especially for fuel ethanol.

In one embodiment, the host cell is from an organism acceptable for the production of food processing aids or food additives. Presently, host cells that are from Bacillus licheniformis, Bacillus subtilis, or Bacillus stearothermophilus are preferred. Suitable plasmids for use in bacterial cells including vectors for self-replication in Bacillus are known in the art. In one embodiment exemplified herein, the host cell is a B. subtilis SC6.1 comprising a xylose-inducible promoter controlling a competency gene. Accordingly, the cells, in the presence of xylose, are competent to bind or take up DNA, such as the polynucleotides, vectors, and other constructs provided herein.

Methods of making and using the chimeric polypeptides and α-amylases

All methods of making and/or using the chimeric polypeptides and thermostable chimeric α-amylases may be in conjunction with one or more other enzymes of any classification, or type, or activity, as described above in the context of chimeric polypeptides, thermostable amylases, and the compositions provided herein. Provided in accordance with another aspect of the disclosure herein are methods of producing the chimeric amylase polypeptides. In one embodiment, the method provided produces at least one chimeric polypeptide or a thermostable α-amylase as described hereinabove. The method utilizes a host cell selected from the group consisting of *Bacillus licheniformis, B. subtilis*, and *B. stearothermophilus*, for a fermentation process wherein a protein is expressed. The protein comprises:

a chimeric polypeptide having a length of about 480-515 amino acid residues, and having an amino-terminal domain comprising about 180 or more contiguous amino acid residues of an N-terminal portion of an AmyL amylase, and a carboxy-terminal domain comprising a carboxy-terminal portion of an AmyS amylase; said chimeric polypeptide having enhanced thermostability relative at least to the AmyS amylase, or a thermostable chimeric α-amylase about 475-520 amino acid residues long, having an N-terminal portion comprising a contiguous amino acid sequence from an N-terminal portion of an AmyL amylase, and a C-terminal portion comprising a contiguous amino acid sequence from a C-terminal portion of an AmyS amylase, said chimeric α-amylase having a specific activity greater than the AmyL amylase, and greater thermostability at 95° C. than the AmyS amylase. After the protein is expressed, the method provides a step of at least partially purifying the expressed polypeptide, thereby producing the composition.

The fermentation process can be of any type, although fed-batch fermentation processes, such as submerged fed-batch fermentation, are useful herein. The methods provided further comprise the step of further purifying the chimeric polypeptide in certain embodiments, to make a purified composition showing no evidence of genotoxic potential in in vitro assays; and no evidence of toxic effects in acute and sub-chronic dosing studies in animals. Such compositions are useful as food processing aids, or in some cases, as direct food additives.

The method produces a purified or partially purified composition that comprises not more than 40 ppm total heavy metals, not more than 5 ppm arsenic, not more than 10 ppm lead, not more than 5×10⁴ total viable organisms (CFU/g), not more than 30 coliforms (CFU/g), and no detectable *Salmonella*, mycotoxins or antibacterial activity by standard tests.

In various embodiments, the methods are also useful for making partially purified or purified compositions that comprise more than one α-amylase activity, and in some embodiments further comprise at least one other enzyme activity.

Also provided are methods using the compositions comprising the chimeric α-amylases. Methods of liquefying a complex carbohydrate are specifically provided. A method of liquefying a starch slurry comprising: making a slurry comprising a starch, heating the slurry to an acceptable temperature for liquefaction, adding to the slurry a composition comprising one or more of: (a) a chimeric polypeptide having a length of about 480-515 amino acid residues, having an amino-terminal domain comprising about 180 or more contiguous amino acid residues of an N-terminal portion of an AmyL amylase, and a carboxy-terminal domain comprising a carboxy-terminal portion of an AmyS amylase; said chimeric polypeptide having enhanced thermostability relative at least to the AmyS amylase, (b) a thermostable chimeric α-amylase about 475-520 amino acid residues long, having an N-terminal portion comprising a contiguous amino acid sequence from an N-terminal portion of an AmyL amylase, and a C-terminal portion comprising a contiguous amino acid sequence from a C-terminal portion of an AmyS amylase, said chimeric α-amylase having a specific activity greater than the AmyL amylase, and greater thermostability at 95° C. than the AmyS amylase, or (c) a combination thereof, and incubating the slurry with the composition for a time and at a temperature sufficient to liquefy the starch slurry.

As used herein "liquefy" does not mean that every available substrate linkage is cleaved, rather it means that the complex carbohydrate is at least partially hydrolyzed, as evidenced by a measurable reduction in final viscosity, an increase in the DE of the slurry, or another measure of an increase in reducing groups, dextrins, or α-maltose units.

In one embodiment of the method of claim, the substrate is a starch, or a carbohydrate comprising amylose, or amylopectin. The method preferably utilizes a slurry that comprises about 15-40% starch on a dry-weight basis. The slurry comprises about 20-40% starch on a dry-weight basis in one embodiment, in another, the slurry comprises between about 30 to about 36 or 37.5% starch. Lower amounts of starch can be used, but may limiting in terms of economic considerations. Maximum viscosity and related factors, such as required power inputs for mixing may limit the maximum amount of starch to be used in the slurry. The skilled artisan will appreciate the practical considerations in making the starch slurry.

In one embodiment, the addition of the composition reduces the peak viscosity of the slurry as much as the addition of an AmyS amylase used in a comparable liquefaction, and reduces the final viscosity of the slurry as much as the addition of a AmyL amylase used in a comparable liquefaction.

The temperature of the liquefaction method can range from room temperature to over 100° C., but more preferably is about 50° C. to about 95° C. In one embodiment, the temperature is at least about 80° C. to about 100° C. The liquefaction can entail a complex temperature curve over time, for example, the reaction may start at a low temperature and be increased by methods known in the art to the desired end temperature. The temperature may also be reduced after a specific amount of time, or after a desired end-point in reached in terms of viscosity, DE value, or another measure of liquefaction. The skilled artisan will thus appreciate that the method need not entail a specific temperature for a particular duration, provided that the amylase activity can function at the temperature and under the conditions provided. Other conditions that can impact the activity include the pH and the calcium ion concentration, in addition to the presence or absence of one or more of detergents, oxidants, or chelators.

In one embodiment, the liquefaction is part of fermentation. Fermentation is used to produce a food product, a food additive, a fuel, or a fuel additive in some embodiments. In preferred embodiments, fermentation is for a fuel or fuel additive that is an alcohol, preferably ethanol or another lower alcohol (e.g. less than about C6-C8).

In another embodiment, the maximal (or peak) viscosity of the slurry is reduced to at least that produced by the AmyS used alone. In various embodiments, the final viscosity is at least that achieved by the AmyL used alone, and is 2-, 3-, 5-, 10-, 15-, 18-, 20-, 21-, 22-, 24-, 25-, 26-, 27-, 28-, 29-, or even 30-fold lower than the maximum viscosity during the process. The skilled artisan will appreciate the more the viscosity is reduced, the further the starch is liquefied, the greater the production of dextrins (or the higher the DE of the resultant liquefied starch).

Another aspect contemplates the use of additional enzymes with the chimeric polypeptides, amylases and compositions provided herein for liquefaction and subsequent processing of the slurry. Thus, two or more α-amylases can be used alone or in combination with other enzymes discussed herein. For example, a third enzyme may be another α-amylase, e.g., a yeast α-amylase, or another α-amylase, either *Bacillus*

α-amylases or non-*Bacillus* α-amylases. Improved liquefaction via enhanced hydrolysis activity during the liquefaction process increases the efficiency subsequent processing steps (see e.g. WO 98/22613). For example, a result may be decreased requirement for glucoamylase during the saccharification step.

Additional enzymes, such as β-amylases, can be used with or in the polypeptides, amylases or compositions. β-amylases suitable for use herein include, but are not limited to, β-amylases from barley Spezyme® BBA 1500, Spezyme® DBA, Optimalt™ ME, Optimalt™ BBA (Genencor International, Inc.), and Novozym™ WBA (Novozymes A/S).

Another enzyme contemplated for use in the composition is a glucoamylase (EC 3.2.1.3). Glucoamylases are derived from a microorganism or a plant. For example, glucoamylases can be of fungal or bacterial origin. Exemplary bacterial glucoamylases are *Aspergillus* glucoamylases, in particular *A. niger* G1 or G2 glucoamylase (Boel et al. (1984), *EMBO J.* 3(5): 1097-1102), or variants thereof, such as disclosed in WO 92/00381 and WO 00/04136; *A. awamori* glucoamylase (WO 84/02921); *A. oryzae* glucoamylase (*Agric. Biol. Chem.* (1991), 55(4): 941-949), or variants or fragments thereof. The glucoamylase advantageously is present in an amount of no more than, or even less than, 0.5 glucoamylase activity unit (AGU)/g DS (i.e., glucoamylase activity units per gram of dry solids). The glucoamylase is derived from an *Aspergillus* sp., *Talaromyces* sp., *Pachykytospora* sp., or *Trametes* sp., with exemplary examples being *Aspergillus niger, Talaromyces emersonii, Trametes cingulata*, or *Pachykytospora papyracea*. In one embodiment, the process also comprises the use of a carbohydrate-binding domain of the type disclosed in, for example, WO 98/22613.

Other contemplated *Aspergillus* glucoamylase variants include variants to enhance the thermal stability: G137A and G139A (Chen et al. (1996), *Prot. Eng.* 9: 499-505); D257E and D293E/Q (Chen et al. (1995), *Prot. Eng.* 8: 575-582); N182 (Chen et al. (1994), *Biochem. J.* 301: 275-281); disulphide bonds, A246C (Fierobe et al. (1996), *Biochemistry*, 35: 8698-8704); and introduction of Pro residues in positions A435 and S436 (Li et al. (1997) *Protein Eng.* 10: 1199-1204). Other contemplated glucoamylases include *Talaromyces* glucoamylases, in particular derived from T. emersonii (WO 99/28448), *T. leycettanus* (U.S. Pat. No. RE 32,153), *T. duponti*, or *T. thermophilus* (U.S. Pat. No. 4,587,215). Contemplated bacterial glucoamylases include glucoamylases from the genus *Clostridium*, in particular *C. thermoamylolyticum* (EP 135138) and *C. thermohydrosulfuricum* (WO 86/01831). Suitable glucoamylases include the glucoamylases derived from *Aspergillus oryzae*, such as a glucoamylase having 50%, 55%, 60%, 65%, 70%, 75%, 80%, 85%, or even 90% homology to the amino acid sequence shown in SEQ ID NO: 2 in WO 00/04136. Also suitable are commercial glucoamylases, such as AMG 200L; AMG 300 L; SAN™ SUPER and AMG™ E (Novozymes); OPTIDEXA® 300 (Genencor International, Inc.); AMIGASE™ and AMIGASE™ PLUS (from DSM); G-ZYME® G900 (Enzyme Bio-Systems); and G-ZYME® G990 ZR (*A. niger* glucoamylase and low protease content). Glucoamylases may be added in an amount of 0.02-2.0 AGU/g DS or 0.1-1.0 AGU/g DS, e.g., 0.2 AGU/g DS.

Another enzyme that can optionally be added is a debranching enzyme, such as an isoamylase (EC 3.2.1.68) or a pullulanases (EC 3.2.1.41). Isoamylase hydrolyses α-1,6-D-glucosidic branch linkages in amylopectin and β-limit dextrins and can be distinguished from pullulanases by the inability of isoamylase to attack pullulan and by the limited action of isoamylase on α-limit dextrins. Debranching enzymes may be added in effective amounts well known to the person skilled in the art.

The polypeptides, amylases, and compositions provided herein can be used in baking processes, They can be added alone or in a combination with other enzymes for any of a variety of purposes. They can be added with other amylases, e.g. an anti-staling amylase to prevent or retard staling, i.e., crumb firming of baked products. The amount of anti-staling amylase will typically be in the range of 0.01-10 mg of enzyme protein per kg of flour, e.g., 0.5 mg/kg ds. Additional anti-staling amylases that can be used in combination with the chimeric polypeptides, amylases, and compositions provided herein include an endo-amylase, e.g., a bacterial endo-amylase from *Bacillus*. The additional amylase is a maltogenic α-amylase (EC 3.2.1.133), e.g., from *Bacillus* in one embodiment. Novamyl® is an exemplary maltogenic α-amylase from *B. stearothermophilus* strain NCIB 11837 and is described in Christophersen et al., Starch 50: 39-45 (1997). Other examples of anti-staling endo-amylases include bacterial α-amylases derived from *Bacillus*, such as *B. licheniformis* or *B. amyloliquefaciens*. The anti-staling amylase may be an exo-amylase, such as β-amylase, e.g., from plant sources, such as soybean, or from microbial sources, such as *Bacillus*.

Phospholipases are also be used together with the chimeric polypeptides, amylases, and compositions disclosed herein in certain embodiments for baking applications. The phospholipase may have $A_1$ or $A_2$ activity to remove fatty acid from the phospholipids, forming a lysophospholipid. It may or may not have lipase activity, i.e., activity on triglyceride substrates. The phospholipase typically has a temperature optimum in the range of 30-90° C., e.g., 30-70° C. The added phospholipases can be of animal origin, for example, from pancreas, e.g., bovine or porcine pancreas, snake venom or bee venom. Alternatively, the phospholipase may be of microbial origin, e.g., from filamentous fungi, yeast or bacteria, such as the genus or species. Exemplary sources of phospholipases include *Aspergillus, A. niger; Dictyostelium, D. discoideum; Mucor, M. javanicus, M. mucedo, M. subtilissimus; Neurospora, N. crassa; Rhizomucor, R. pusillus; Rhizopus, R. arrhizus, R. japonicus, R. stolonifer; Sclerotinia, S. libertiana; Trichophyton, T. rubrum; Whetzelinia, W. sclerotiorum; Bacillus, B. megaterium, B. subtilis; Citrobacter, C. freundii; Enterobacter, E. aerogenes, E. cloacae; Edwardsiella, E. tarda; Etwinia, E. herbicola; Escherichia, E. coli; Klebsiella, K. pneumoniae; Proteus, P. vulgaris; Providencia, P. stuartii; Salmonella, S. typhimurium; Serratia, S. liquefasciens, S. marcescens; Shigella, S. flexneri; Streptomyces, S. violeceoruber; Yersinia, Y. enterocolitica; Fusarium, F. oxysporum*, (strain DSM 2672 for example).

The phospholipase is added in an amount that improves the softness of the bread during the initial period after baking, particularly the first 24 hours. The amount of phospholipase will typically be in the range of about 0.01-10 mg of enzyme protein per kg of flour, e.g., 0.1-5 mg/kg. Phospholipase activity generally will be in the range of about 20-1000 Lipase Unit (LU)/kg of flour, where a Lipase Unit is defined as the amount of enzyme required to release 1 μmol butyric acid per minute at 30° C., pH 7.0, with gum arabic as emulsifier and tributyrin as substrate.

Optionally, an additional enzyme may be used together with the anti-staling amylase and the phospholipase. The additional enzyme may be a second amylase, such as an amyloglucosidase, a β-amylase, a cyclodextrin glucanotransferase, or the additional enzyme may be a peptidase, in particular an exopeptidase, a transglutaminase, a lipase, a cellulase, a hemicellulase, in particular a pentosanase, such as xylanase, a protease, a protein disulfide isomerase, e.g., a protein disulfide isomerase as disclosed in WO 95/00636, for example, a glycosyltransferase, a branching enzyme (1,4-α-glucan branching enzyme), a 4-α-glucanotransferase (dextrin glycosyltransferase) or an oxidoreductase, e.g., a peroxidase, a laccase, a glucose oxidase, a pyranose oxidase, a lipooxygenase, an L-amino acid oxidase, or a carbohydrate oxidase. The additional enzyme(s) may be of any origin, including mammalian and plant, and particularly of microbial (bacterial, yeast or fungal) origin and may be obtained by techniques conventionally used in the art.

The xylanase is typically of microbial origin, e.g., derived from a bacterium or fungus, such as a strain of *Aspergillus*, in particular of *A. aculeatus, A. niger* (cf. WO 91/19782), *A. awamori* (e.g., WO 91/18977), or *A. tubigensis* (e.g., WO 92/01793); from a strain of *Trichoderma*, e.g., *T. reesei*, or from a strain of *Humicola*, e.g., *H. insolens* (e.g., WO 92/17573). Pentopan® and Novozym 384® are commercially available xylanase preparations produced from *Trichoderma reesei*. The amyloglucosidase may be an *A. niger* amyloglucosidase (such as AMG®). Other useful amylase products include Grindamyl® A 1000 or A 5000 (available from Grindsted Products, Denmark) and Amylase® H or Amylase® P (available from Gist-Brocades, The Netherlands). The glucose oxidase may be a fungal glucose oxidase, in particular an *Aspergillus niger* glucose oxidase (such as Gluzyme®). An exemplary protease is Neutrase®. An exemplary lipase can be derived from strains of *Thermomyces* (Humicola), *Rhizomucor, Candida, Aspergillus, Rhizopus*, or *Pseudomonas*, in particular from *Thermomyces lanuginosus* (*Humicola lanuginosa*), *Rhizomucor miehei, Candida antarctica, Aspergillus niger, Rhizopus delemar* or *Rhizopus arrhizus*, or *Pseudomonas cepacia*. In specific embodiments, the lipase may be Lipase A or Lipase B derived from *Candida antarctica* as described in WO 88/02775, for example, or the lipase may be derived from *Rhizomucor miehei* as described in EP 238,023, for example, or *Humicola lanuginosa*, described in EP 305,216, for example, or *Pseudomonas cepacia* as described in EP 214,761 and WO 89/01032, for example.

Provided herein are methods of cleaning a surface to remove an unwanted or undesired starch residue. The methods comprise the steps of providing a surface that has a starch residue to be removed, contacting the surface with a composition that comprises one or more chimeric polypeptides or α-amylases, for a time and at a temperature sufficient, and under conditions permissive to result in removal of the starch residue. The surface can be on any material; for example, it can be on a dish, plate, glass, etc, or it can be on clothing or fabric. It can also be for example a counter-top or work surface, or a commercial vessel of any type that must be periodically or regularly cleaned.

In one embodiment, the composition comprises at least one other enzyme, for example one or more of a protease, a lipase, an additional amylase, or a combination thereof. In another embodiment, a step of rinsing or bulk removal of residue is implemented prior to the contacting step. Such a step removes bulk starch from the cleaning process to enable the enzyme to work on the remaining, and more difficult to remove, substrate. The method of cleaning can be conducted at any temperature, but preferably the temperature during the contacting step reaches at least 50-100° C. In one embodiment, the method comprises a step of sterilizing the surface, or steam treating the surface after the residue is removed. The composition further comprises at least one detergent, oxidant, chelator, or a combination thereof in several embodiments.

In embodiments wherein the composition comprises one or more additional enzymes, while the composition can comprise any useful enzyme activity, the following embodiments may offer particular advantages.

The composition can comprise 2,6-β-D-fructan hydrolase, one or more α-amylases, and one or more other cleaning enzymes, such as a protease, a lipase, a cutinase, a carbohydrase, a cellulase, a pectinase, a mannanase, an arabinase, a galactanase, a xylanase, an oxidase, a laccase, and/or a peroxidase, and/or combinations thereof. In general the properties of the chosen enzyme(s) preferably are compatible with the selected detergent, (e.g., pH-optimum, compatibility with other enzymatic and non-enzymatic ingredients, etc.), and the enzyme(s) are preferably provided in effective amounts.

Proteases from any source are suited for use herein including those of animal, vegetable or microbial origin. Chemically-modified or engineered enzymes are also suitable. The protease can have any type of activity or active site known, e.g. exo- or endo-proteolytic activities of the serine, metallo- or alkaline- or acid-type protease, depending on the conditions of use. Alkaline proteases are preferred in certain embodiments, as are trypsin-like proteases. Examples of alkaline proteases are subtilisins, especially those derived from *Bacillus* spp., e.g., subtilisin Novo, subtilisin Carlsberg, subtilisin 309 (see, e.g., U.S. Pat. No. 6,287,841), subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include, but are not limited to, the variants described in WO 92/19729 and WO 98/20115. Suitable commercially available protease enzymes include Alcalase®, Savinase®, Primase™, Duralase™, Esperase®, and Kannase™ (Novo Nordisk A/S); Maxatase®, Maxacal™, Maxapem™, Properase™, Purafect®, Purafect OxP™, FN2™, and FN3™ (Genencor International, Inc.).

Lipases of any type may be used in conjunction with the compositions provided herein. Exemplary lipases include those of bacterial or fungal origin. Chemically-modified and engineered enzymes are also useful herein. Examples of useful lipases include, but are not limited to, lipases from *Humicola* (synonym *Thermomyces*), e.g. *H. lanuginosa* (*T. lanuginosus*) (see, e.g., EP 258068 and EP 305216) and *H. insolens* (see, e.g., WO 96/13580); a *Pseudomonas lipase* (e.g., from *P. alcaligenes* or *P. pseudoalcaligenes*; see, e.g., EP 218 272), *P. cepacia* (see, e.g., EP 331 376), *P. stutzeri* (see, e.g., GB 1,372,034), *P. fluorescens, Pseudomonas* sp. strain SD 705 (see, e.g., WO 95/06720 and WO 96/27002), *P. wisconsinensis* (see, e.g., WO 96/12012); a *Bacillus* lipase (e.g., from *B. subtilis*; see, e.g., Dartois et al. *Biochemica Biophysica Acta*, 1131: 253-360 (1993)), *B. stearothermophilus* (see, e.g., JP 64/744992), or *B. pumilus* (see, e.g., WO 91/16422). Additional lipase variants contemplated for use in the formulations include those described, for example, in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105. Some commercially-available lipase enzymes include Lipolase® and Lipolase® Ultra (Novo Nordisk A/S).

Polyesterases useful herein include, but are not limited to, those described in WO 01/34899 (Genencor International, Inc.) and WO 01/14629 (Genencor International, Inc.), and can be included in any combination with other enzymes discussed herein.

The compositions can also be combined with other α-amylases including commercially available amylases, such as, but not limited to Duramyl®, Termamyl™, Fungamyl® and BAN™ (Novo Nordisk A/S), as well as Rapidase®, and Purastar® (Genencor International, Inc.).

Cellulases of any type or origin, such as those of bacterial or fungal origin can be added to, or used with, the compositions, as can chemically-modified or engineered enzymes. Suitable cellulases include cellulases from the genera *Bacillus, Pseudomonas, Humicola, Fusarium, Thielavia,* and *Acremonium.* For example, the fungal cellulases produced from *Humicola insolens, Myceliophthora thermophila* and *Fusarium oxysporum* disclosed in U.S. Pat. Nos. 4,435,307; 5,648,263; 5,691,178; 5,776,757; and WO 89/09259. Exemplary cellulases have benefit for the color care of textiles. Examples of such cellulases are described in EP 0495257; EP 531 372; WO 99/25846 (Genencor International, Inc.), WO 96/34108 (Genencor International, Inc.), WO 96/11262; WO 96/29397; and WO 98/08940, for example. Other examples are cellulase variants, such as those described in WO 94/07998; WO 98/12307; WO 95/24471; PCT/DK98/00299; EP 531 315; U.S. Pat. Nos. 5,457,046; 5,686,593; and 5,763,254. Commercially available cellulases include Celluzyme® and Carezyme® (Novo Nordisk A/S); Clazinase™ and Puradax® HA (Genencor International, Inc.); and KAC-500 (B)™ (Kao Corporation).

Peroxidases and oxidases are also suitable for use in or with the compositions provided herein, include enzymes of plant, bacterial or fungal origin. Chemically-modified and engineered enzymes are also well-suited for use herein. Examples of useful peroxidases include peroxidases from *Coprinus,* e.g., from *C. cinereus,* and variants thereof as those described in WO 93/24618, WO 95/10602, and WO 98/15257. Commercially available peroxidases include Guardzyme™ (Novo Nordisk A/S), for example.

Also provided herein are methods of treating a woven material using the chimeric α-amylases described herein. Methods of treating woven materials, such as fabrics, with amylases are known in the art. The methods provided can improve the feel and/or appearance of a woven material, such as a textile or a fabric. The methods comprise contacting the woven material with a liquid comprising chimeric polypeptides or thermostable α-amylases. In one embodiment, the woven material is a fabric or textile. In another embodiment, the woven material is treated with the liquid under pressure. The liquid is generally an aqueous solution.

The methods are typically applied during or after a weaving process, e.g., the weaving of a fabric or textile. Alternatively, the method can be used during a desizing stage, or during one or more additional steps further processing the woven material. The methods are useful because during the weaving process for many materials, such as fabrics and textiles, the material (e.g. threads to be woven) is exposed to considerable mechanical strain. Prior to the weaving process, particularly on commercial looms, the materials to be woven are often coated with a "sizing" comprising starch or starch derivatives, to increase their tensile strength and to prevent breaking. The chimeric polypeptides and thermostable amylases provided herein can be applied during or after weaving to remove such sizing starch or starch derivatives.

The chimeric polypeptides and chimeric α-amylases provided herein can be used alone or with other desizing chemical reagents, such as detergents and/or desizing enzymes to desize woven materials such as fabrics, including cotton and cotton-containing fabrics.

The chimeric polypeptides and α-amylases provided herein also have application for enzymatic finishing methods have been developed for clothing, for example, in the manufacture of denim jeans. The action of amylolytic enzymes can provide softness to the fabric and make the cotton more accessible to the subsequent enzymatic finishing steps (e.g., to achieve a stone-washed appearance).

Kits for practicing the foregoing methods of liquefying a starch slurry, cleaning a starch residue from a surface, and for treating a woven material to remove a coating comprising starch or a starch derivative are also provided herein. The kits include at least one chimeric polypeptide or chimeric α-amylase as provided herein, or one composition provided herein, along with instructions for practicing the corresponding methods.

All references cited herein are incorporated by reference in their entirety herein for all purposes. The working examples provided below are provided to further describe and illustrate certain aspects of the chimeric α-amylases, and thus should not be construed to be limiting.

EXAMPLES

Methods
Hybrid Strain Construction
All chimeric nucleotide sequences were ordered as full-length synthetic genes from DNA 2.0 (Menlo Park, Calif.). All plasmids were digested with EcoRI and BamHI restriction endonucleases. The gene fragments were gel extracted using the Qiagen Gel Extraction kit, according to the manufacturer's protocol. Similarly, the integrating *B. subtilis* vector, pJH101t, was digested with EcoRI and BamHI restriction endonucleases. Following agarose gel separation, the ~5 kb plasmid backbone band was gel extracted and cleaned up with the Qiagen Gel Extraction kit. The plasmid pJH101t is a derivative of the plasmid pBR322, originally isolated from *E. coli,* with the EcoRI/HindIII fragment replaced by the pUC 18 multicloning site EcoRI/HindIII fragment, and the HindIII/BamHI fragment replaced by the *Bacillus amyloliquefaciens* alkaline protease (apr) gene terminator sequence, and containing also the HpaII/Sau3a fragment of the natural *Bacillus* plasmid pC194 carrying the chloramphenicol acetyl transferase (CAT) gene (blunted) in the PvuII site. (Ferrari, F A, Nguyen A, Lang D, and Hoch J A (1983) Construction and Properties of an Integrable Plasmid for *Bacillus subtilis* J. Bacteriology, 154:1513-1515).

All chimeric genes were ligated into pJH101t at the EcoRI-HindIII sites using DNA Ligation Kit, Mighty Mix from Takara (Madison, Wis.). 5 □L of the ligation mixture were transformed into Invitrogen Oneshot Top10 *E. coli* chemical competent cells according to the manufacturer's protocol. LA+50 ppm carbenicillin plates were used for selection of transformants.

Transformants were screened to determine if the chimeric gene was present by extracting plasmid DNA from the clones using the Qiagen Miniprep kit. The plasmid was then digested with EcoRI-BamHI to see if a ~2.2 kb band is present indicating that the vector contains the hybrid gene. For final verification, the miniprep DNA was extracted and sequenced by Sequetech (Mountain View, Calif.) using the following sequencing primers:

```
Fred550-F
5' aaccgcggttgaagtcgatccc 3'      (SEQ ID NO: 35)

Fred610-R
5' cccggaaaatgaaaatgtgtcc 3'      (SEQ ID NO: 36)

Ethyl 1130-F
5' cgcacgttaatgaccaatactc 3'      (SEQ ID NO: 37)

Ethyl 1190-R
5' gcttggccgggctcggtgtcat 3'      (SEQ ID NO: 38)
```

The constructs were named pJH101-AprFr186Et, pJH101-AprFr187Et, etc (see FIG. 1) to refer to the chimeric amylase encoded therein. Plasmid DNA containing the chimeric construct was transformed into frozen *B. subtilis* SC6.1 competent cells (also called BG3594comK, genotype: DaprE, DnprE, degUHy32, oppA, DspoIIE3501, amyE::xylRPxylAcomK-phleo)) by adding 5-10 μL of plasmid to 200 μL of competent cells followed by 37° C. incubation at 250 rpm for 1 hour. The SC6.1 *B. subtilis* cells have a competency gene (comK) which is placed under a xylose inducible promoter, so xylose was used to induce competency for DNA binding and uptake. The transformation reaction was plated on LA+5 ppm chloramphenicol+1% insoluble starch and incubated at 37° C., overnight.

Transformants showing a clearing (or halo) in the agar around the colony were selected and amplified by streaking on LA+25 ppm chloramphenicol+1% insoluble starch. The formation of a halo in the agar around the colony reflects the ability of the transformed cells to produce an amylase enzyme that degrades the insoluble starch in the agar medium. The plates were incubated at 37° C., overnight. Colonies with a larger halo were selected to grow in shake flasks. For the purpose of protein expression, a fresh single colony was inoculated into 5 mL LB+25 ppm chloramphenicol and incubate at 37° C., 250 rpm, for 6 to 8 hours. 30 μL of this pre-culture was added into a 250 mL flask filled with 30 mL of cultivation media (described below) supplemented with 25 ppm chloramphenicol and 5 mM $CaCl_2$. The shake flasks were incubated for 60-65 hours at 37° C., with mixing at 250 rpm. Cultures were harvested by centrifugation at 5000 rpm for 20 minutes in conical tubes. The culture supernatants, enriched in recombinant amylase, were used for assays.

The cultivation media was an enriched semi-defined media based on MOPs buffer, with urea as major nitrogen source, glucose as the main carbon source, and supplemented with 1% soytone for robust cell growth.

For construction of chimeras with a salt bridge mutation, the original backbone vector, pJH101-AprFr200Et (and 202, 228, 249, 254, 259), was used as a template for a site directed mutagenesis reaction using the Stratagene QuikChange Site-Directed Mutagenesis kit. 50 ng of template DNA was used for PCR along with the following primers:

```
SS187DT-200etc fwd
                                           (SEQ ID NO: 39)
5'-gcttgggattgggaagttgacacagaaaacggcaactatg-3'

SS187DT-200etc rev
                                           (SEQ ID NO: 40)
5'-catagttgccgttttctgtgtcaacttcccaatcccaagc-3'
```

Thermocycler conditions were 1× at 95° C. for 1 min, 18× at 95° C. for 50 sec, 60° C. for 50 sec, 68° C. for 8.5 min, followed by 1× at 68° C. for 7 min and hold at 4° C. Following PCR, all reactions were incubated at 37° C., overnight after addition of 1 μL of DpnI. 1.5 μL of the digested reaction was transformed into Invitrogen Oneshot Top10 *E. coli* chemical competent cells following the manufacturer's protocols. The reactions were plated on LA+50 ppm carbenicillin. To extract plasmid DNA for sequencing, transformants were cultured in 5 mL LA+50 ppm carbenicillin, 37° C., 250 rpm, overnight. Plasmid DNA was extracted using the Qiagen Miniprep Kit following the manufacturer's protocol. Plasmid DNA was sequenced by Sequetech (Mountain View, Calif.) using the sequencing primers listed below:

```
Fred550-F
5' aaccgcggttgaagtcgatccc 3'       (SEQ ID NO: 35)

Fred610-R
5' cccggaaaatgaaaatgtgtcc 3'       (SEQ ID NO: 36)

Ethyl 1130-F
5' cgcacgttaatgaccaatactc 3'       (SEQ ID NO: 37)

Ethyl 1190-R
5' gcttggccgggctcggtgtcat 3'       (SEQ ID NO: 38)
```

After determining which isolates had the correct sequence, 10 μL of plasmid DNA was transformed into 100 μL of frozen *B. subtilis* SC6.1 competent cells. Transformants were grown as described above.

Enzymatic Thermostability Assay

In this assay, the thermostability of the amylases was determined using a PCR thermocycler. Residual activity of the amylases was measured after incubation at a set temperature such as 95° C. following sampling over a standard time interval such as 60 minutes to obtain the inactivation curve at that temperature. For each time point, 110 μl sample were placed in a thin-walled PCR tube and held at 25° C. for 4 minutes in the thermocycler after the tubes were sealed. The temperature was ramped to e.g. 95° C. Timing was initiated when the target temperature was reached. Over appropriate time intervals, tubes were removed and placed on ice. The samples were assayed for residual endo alpha amylase activity using the Megazyme Ceralpha assay as described below.

Megazyme Ceralpha Assay:

This assay is a modification of the published protocols for Megazyme endo alpha-amylase Kit K-CERA 08/05 (AOAC Method 2002.01) (Megazyme International, Ireland). Reagent vials contain the substrate, which is non-reducing end-blocked p-nitrophenyl maltoheptaoside (BPNPG7, 54.5 mg) and thermostable alpha glucosidase (125 U at pH 6.0). For each assay, the entire contents of one vial was dissolved in 10.0 mL of distilled water. 30 mL assay buffer (50 mM Na malate, 2.6 mM $CaCl_2$, 50 mM NaCl, 0.002% Triton X-100, pH 6.7) was added to the vial solution and 10 mL aliquots of this were frozen for further use. 0.79 mL substrate solution in buffer was added to a (preferably masked) cuvette. The cuvette was placed in the holder and a blank reading was obtained. Ten μL enzyme samples were then added to the cuvette to start the assay. Absorbance per minute was measured at 400 nm or 410 nm and the values corrected for dilution and protein concentration. The % activity remaining is reported for each chimeric enzyme after normalizing to 100% for the AmyS control.

Specific activity determination by DNS reducing sugar assay

In this assay, the relative specific activity of the chimeric enzymes with respect to non-chimeric enzymes was determined by measuring the release of glucose from potato starch substrate using the DNS reducing sugar detection method described below.

Reagents Used:

Buffer:

200 mM sodium acetate+2.5 mM $CaCl_2$ and 0.002% Tween 20

DNS Solution:

8 g NaOH were dissolved in 300 mL water and 5 g 3-5 Dinitro Salicylic acid was added to this solution and dissolved, with heating if necessary. 150 g sodium potassium tartarate was then added to this solution and the total volume made up to 500 mL.

Substrate:

4% potato starch solution (5.33 g potato starch dissolved to 100 mL of water). For a working substrate solution, 1 part buffer was added to 3 parts starch solution. Substrate solution was made fresh each day.

Procedure: An aliquot of 110 µL of substrate was added to 2004 PCR tubes. The tubes were placed in the PCR thermocycler. The program was started by first keeping the tubes at 4° C. for a few minutes. During this time, 10 µL of enzyme, appropriately diluted with buffer containing 0.002% Tween 20, was added to the tubes. The tubes were quickly mixed and as soon as the thermocycler reached the desired reaction temperature of 95° C., the 0 timepoint reaction was stopped by the addition of 10 µL 1% NaOH. At each time point, one reaction tube was removed and quenched with 10 µL 1% NaOH. When all reactions were completed, 32.5 µL of each reaction mixture was placed in another 200 µL PCR tube containing 75 µL of water. 100 µL DNS solution was added to each tube and the contents mixed thoroughly. The tubes were incubated at 99° C. for 5 minutes in the PCR thermocycler. Following incubation, the tubes were cooled, 150 µL of each reaction mixture was placed in a microtiter plate well, and the absorbance measured at 543 nm. Glucose was used as a standard. The specific activity values are expressed as mg glucose/sec per mg enzyme.

4) Viscosity Measurement Assay (Glass Cooker/Viscometer Procedure)

In this assay, viscosity reduction of corn starch substrate solution at pH 5.8. by amylases was measured in a glass cooker/viscometer. The corn starch substrate slurry was made up fresh in batch mode with 36% corn flour dry solids in distilled water and adjusted to pH 5.8 using sulfuric acid. The slurry was pre-incubated for 1 hour at 60° C. in a large plastic beaker. For viscosity measuring, the reaction vessel was heated to 110° C. with an oil bath with a thermal coat around reaction vessel while it was heating to temperature. The slurry was poured into the reaction vessel with stirring at a rotation speed of 100 rpm. Diluted alpha amylase enzyme samples were added directly into the reaction vessel to dose the slurry with 1.33 U/g DS. The thermal coat was removed from the reaction vessel and the vessel maintained at 85° C. for the duration of the experiment. The internal temperature and viscosity was measured using a EUROSTAR/IKA Labortechnik control-visc P7 electronic overhead stirrer with torque read output every 30 seconds for the first 10 minutes, then every 4 minutes for a total of 62 minutes.

Example 1

Creation of Novel Chimeric Amylases from AmyL and AmyS Sequences

An effort was undertaken to make chimeras of AmyL and AmyS to combine the preferred attributes of AmyL-type enzymes (AmyL and variants thereof) with those of AmyS-type enzymes (AmyS and variants thereof) into individual enzymes. Ideally, resultant chimeric enzymes would have the best properties of each enzyme—e.g., thermostability similar to that of AmyL-type enzymes, combined with the high specific activity of AmyS-type enzymes for starch substrates at high temperature. Such enzymes would be useful in starch liquefaction, such as for ethanol production, as the catalytic activity obtained from them would ideally lead to a fast initial rate of viscosity reduction and low final viscosity.

A series of chimeric molecules were constructed from AmyL and AmyS (SEQ ID NOs: 4-17). The chimeras comprised an N-terminal portion derived from AmyL (SEQ ID NO: 1), and a C-terminal portion derived from AmyS (SEQ ID NO: 2). The N-terminal portion of the chimeras comprised a minimum of 186 amino acid residues from the N-terminal end of the mature polypeptide sequence of AmyL (SEQ ID NO: 1) and a maximum of about 260 such amino acid residues. The remainder of the chimera (i.e. the C-terminal portion) comprised amino acid residues from the C-terminal portion of the mature polypeptide sequence of AmyS (SEQ ID NO: 2). A maximum of 297-326 amino acid residues from the C-terminal region of AmyS (SEQ ID NO: 2), and a minimum of 224-253 such amino acid residues. The C-terminal portion of the chimeras all included the amino acid residues K-T-T corresponding to positions 484-486 of the mature AmyS sequence (SEQ ID NO: 2). The chimeras are generally named for the last residue of the AmyL-derived sequence. See Hybrid Strain Construction, under "Methods", above, and FIG. 1, for description of cloning process.

The following chimeric α-amylases were constructed for use herein in the working examples:

First Generation Chimeras included: 186, 187, 200, 202, 228, 249, 254, and 259.

Second Generation Chimeras included: 200SB, 202SB, and 228SB.

Third Generation Chimeras included: 249SB, 254SB, and 259SB.

Example 2

Thermostability Screening of First Generation Chimeric α-Amylases Derived from AmyL and AmyS Enzymes The first generation chimeras consisted of single cross-over mutants wherein the N-terminal portion of the chimeric amylase derived from AmyL and the C-terminal portion derived from AmyS as described above. The chimeric amylases screened for thermostability were 186, 187, 200, 202, 228, 249, 254, and 259. The chimeric amylases were assayed at 95° C. throughout the time course. Samples were removed at the indicated time points and activity was measured. For each chimera, the percent activity is plotted versus the number of minutes the enzyme was held at 95° C., in 50 mM malate buffer, pH 5.6 with 2.6 mM $CaCl_2$ and 50 mM NaCl. Assay conditions were as described in the Methods section above. For each enzyme, the remaining activity was calculated as a percentage of the activity of for the enzyme that had not been incubated at 95° C. The control enzyme was AmyS control (SEQ ID NO: 3).

Figure 2:
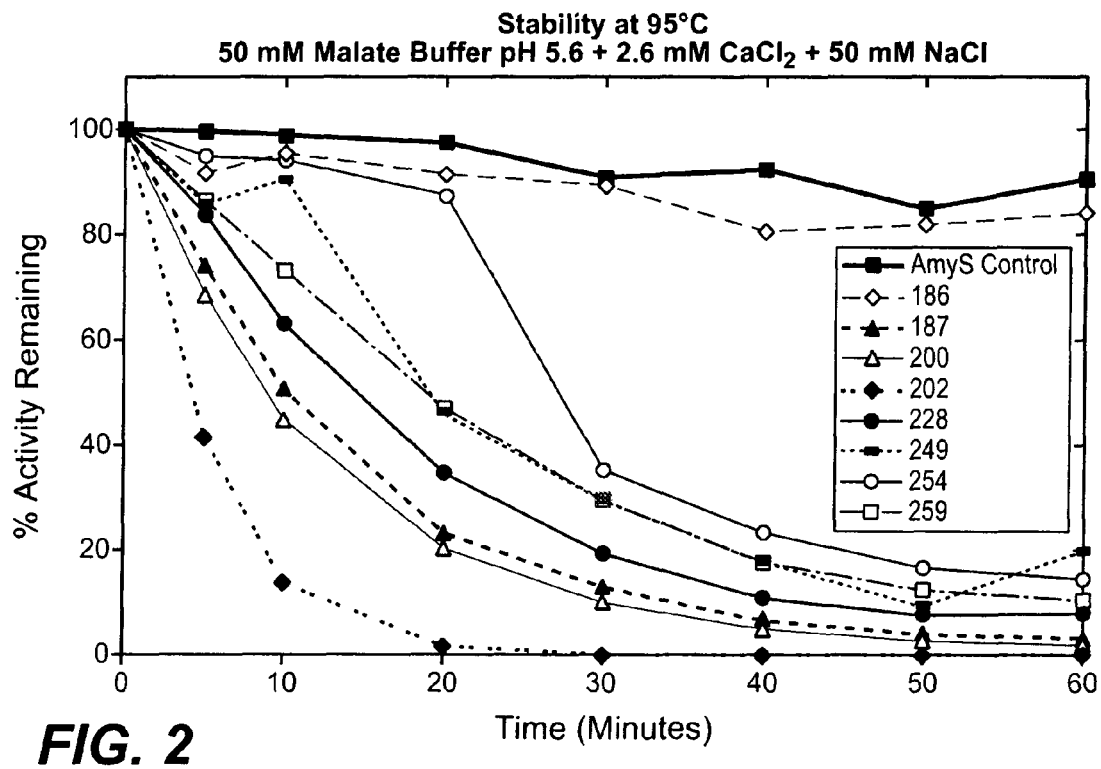
FIG. 2 shows the results of the performance of chimeric α-amylases in a thermostability screen at 95° C. in comparison to a control, AmyS control. The chimeric α-amylases comprised an amino terminal portion from AmyL and a carboxy-terminal portion from AmyS. The chimeras tested included 186, 187, 200, 202, 228, 249, 254, and 259. The three-digit number, where used in the name of a chimeric α-amylase herein, indicates the position of the last amino acid residue of the AmyL sequence, with the remainder of the chimera derived from the AmyS sequence. The control enzyme ("AmyS control") (SEQ ID NO: 3) used is a variant AmyS with a deletion of R179-G180 [described in WO2005/111203]. The enzymes were held at desired temperature (95° C.) and samples were removed at the time points indicated for assay. The assay conditions included pH 5.6 50 mM malate buffer, 2.6 mM $CaCl_2$, and 50 mM NaCl. The graph shows the relative catalytic activity remaining (as a percentage) on the y-axis, over time (min) on the x-axis, using the MEGAZYME CERALPHA synthetic oligosaccharide substrate, as described herein. Detailed description of the incubation conditions and assays are provided in the methods section.

Results and Discussion. Results are shown in FIG. 2. Based on what was previously known or believed about the thermostability of AmyL and AmyS, in the single cross-over chimeras expectations were that the greater the number of amino acid residues from AmyL, the greater the thermostability of the chimera. However, as can be seen from FIG. 2, it was unexpectedly discovered that the chimeric α-amylase with the fewest number of AmyL-derived amino acid residues was the most thermostable. Interestingly, the chimeric amylase containing the first 187 residues derived from AmyL was not highly thermostable, despite the difference of only a single amino acid residue—that at position 187.

Example 3

Thermostability Screening of Second Generation Chimeric α-Amylases Derived from AmyL and AmyS Enzymes: Incorporation of Stabilizing Structures The stability data from Example 2 showed that among the chimeric α-amylases tested, the chimera containing only the first 186 amino acid residues of the AmyL sequence had high thermostability, while the other chimeric α-amylases, containing more of the AmyL sequence, were not thermostable, including the 187 chimera, which differed from the 186 chimera at only position 187. The data suggested that the replacement of the Asp residue with a Ser residue at position 187 was directly related to the lack of thermostability of the 187 chimera, and possibly related to the lack of thermostability of each of the chimeric amylases containing more than 186 amino acid residues from AmyL.

This is highly surprising given that other work has reported that the mutation S187D in AmyL-derived amylases reduces thermostability of the amylase. For example, U.S. Pat. No. 6,939,703 to Van Der Laan and Aehle discloses that, although S187D mutants had a higher specific activity under certain assay conditions, the S187D amylase had a substantially shorter half-life at 93° C. than the *B. licheniformis* wild-type amylase at all calcium ion concentrations tested. U.S. Pat. No. 6,143,708 to Svendson et al. also discloses that S187D mutants of *B. licheniformis* amylase had increased specific activity, however they also report substantially reduced thermostability at 70° C. at either pH 4.5 or 6.2 across a range of calcium ion concentrations.

In the context of the chimeric amylases that are the subject of this disclosure it was thus completely unexpected that the alteration of Ser to Asp at position 187 would increase thermostability. To test this hypothesis, the mutations S187D and S188T were introduced into a number of the chimeric α-amylases that were not highly thermostable in the screen of the first generation chimeras. The chimeric α-amylases tested included 200SB, 202SB, and 228SB. As in Example 2, the thermostability of each chimeric enzyme at 95° C. was compared to that of the AmyS control. The assays and calculation of activity remaining were as in Example 2.

Figure 3:
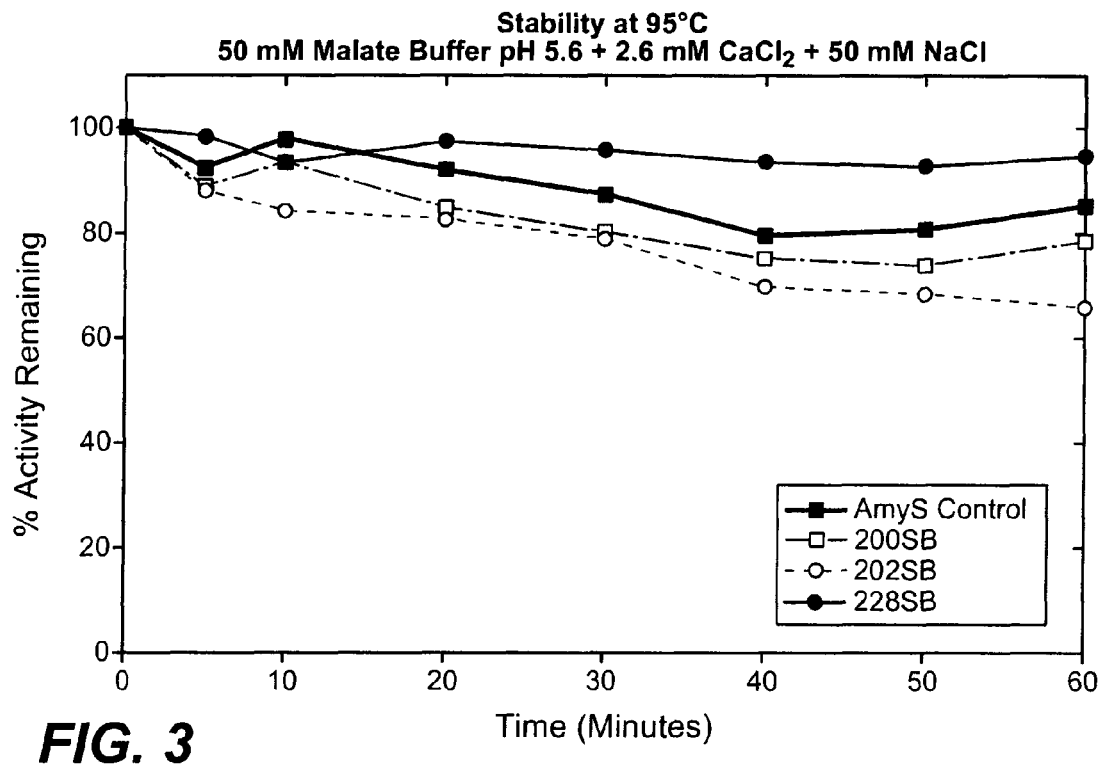
FIG. 3 shows the thermostability of additional chimeric α-amylases at 95° C. The graph, as in FIG. 2, shows the amylase activity remaining (as a percentage) on the y-axis, over time (min) on the x-axis. The reaction conditions were the same as in FIG. 1. The chimeras tested include 200SB, 202SB, and 228SB. "SB" as used herein, indicates that a stabilizing salt-bridge was created by introduction of S187D and S188T mutations. The control was the AmyS control (SEQ ID NO: 3).

Results and Discussion. The results of the thermostability screen are shown in FIG. 3 for the first set of chimeric molecules. Surprisingly, the alteration of two amino acid residues was indeed found to improve the stability of the chimeras. Without being limited a particular theory of operation, it was considered that the S187D and S188T mutations may help form a salt bridge that stabilizes the active site, or the overall tertiary structure of the enzyme, thereby enhancing thermostability. While the S187D mutation in the context of an otherwise AmyL amino acid sequence is destabilizing with respect to thermal challenges, in the context of the chimeric amylases here, it is evident that the Asp residue present in the S187D mutants interacts with one or more amino acid residues from the AmyS portion of the molecule to result in enhanced stability. Thus, e.g. the chimeric amylases with 200, 202, and even 228 residues from the AmyL sequence had good thermostability provided that a salt-bridge or other stabilizing structure was included.

Example 4

Thermostability Screening of Third Generation Chimeric α-Amylases Derived from AmyL and AmyS Enzymes. Incorporation of Salt Bridges Stabilizing Chimeras with Longer AmyL Sequences Based on the observations from Examples 2 and 3 on the first and second generation chimeras, it was believed that chimeras with longer portions of AmyL, and concomitantly less AmyS sequence could be produced. Chimeras were produced with up to 259 amino acid residues at the N-terminal portion derived from an AmyL, to determine whether chimeric amylases could be produced with both enhanced thermostability and high specific activity.

The chimeric α-amylases tested included 249SB, 254SB, and 259SB. The thermostability of each chimeric enzyme was tested at 95° C., and compared to that of the AmyS control, as in the preceding Examples. The assays and calculation of activity remaining were also performed as in the preceding Examples.

Figure 4:
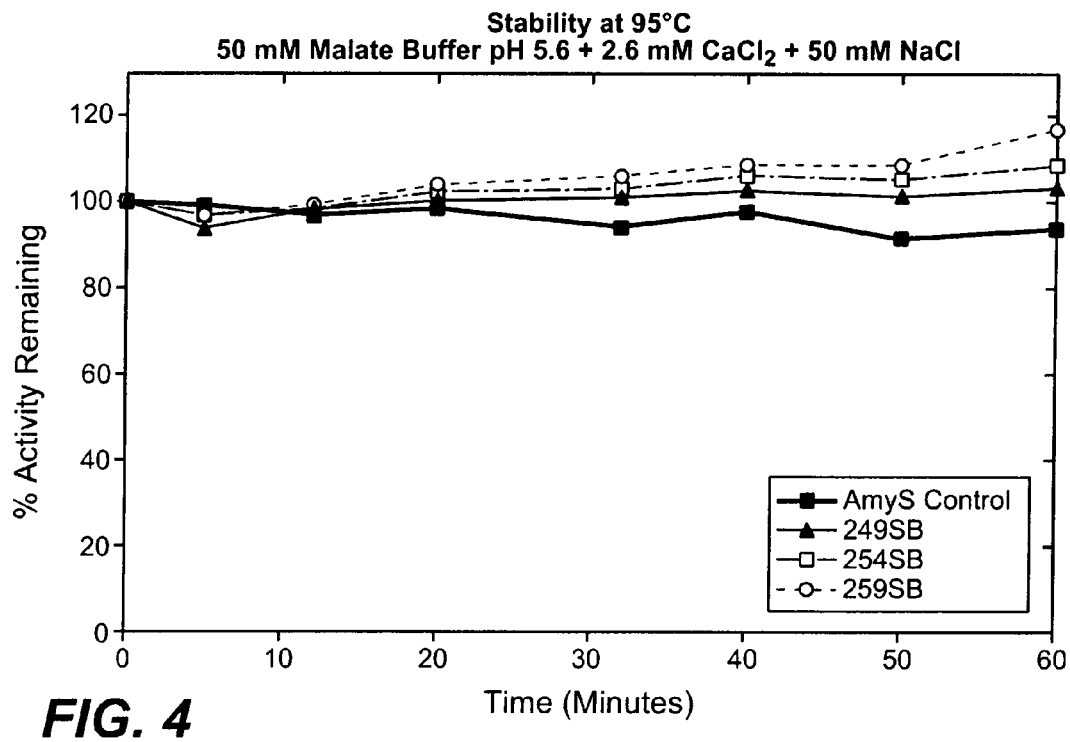
FIG. 4 shows the thermostability of additional chimeric α-amylases at 95° C. The graph is as in FIGS. 2 and 3. The reaction conditions were the same as in FIGS. 2 and 3. The samples tested include the AmyS control, and chimeras 249SB, 254SB, and 259SB.

Results and Discussion. The results of the thermostability screen for the second set of chimeric amylases are shown in FIG. 4. As can be seen, each of the chimeric amylases show excellent thermostability under the conditions tested. These third-generation chimeric enzymes had 30-40% more AmyL sequence than the first-generation enzymes, which did not demonstrate good thermostability, showing that the rational incorporation of strategically-placed stabilizing structures, particularly salt bridges enabled chimeric α-amylases with the beneficial properties of both AmyL and AmyS to be made. These enzymes will thus be useful for all applications where thermostable amylases are currently used, such as starch degradation, HFCS production, desizing, and cleaning. Due to their increased specific activity and high thermostability, they will be particularly useful in starch liquefaction processes as they provide reduced peak viscosity, as well as low final viscosity of the starch slurry.

Example 5

Specific Activity of Chimeric α-Amylases Derived from AmyL and AmyS Enzymes.

The chimeric α-amylases tested for specific activity were 186, 228 and 228SB. The evaluation included the AmyL protein (SEQ ID NO: 1) as well as the AmyS control (SEQ ID NO: 3). The specific activity of the five enzymes was determined at 75° C. using potato starch as the substrate and DNS reducing sugar assay to measure the relative reaction rates.

Figure 5:
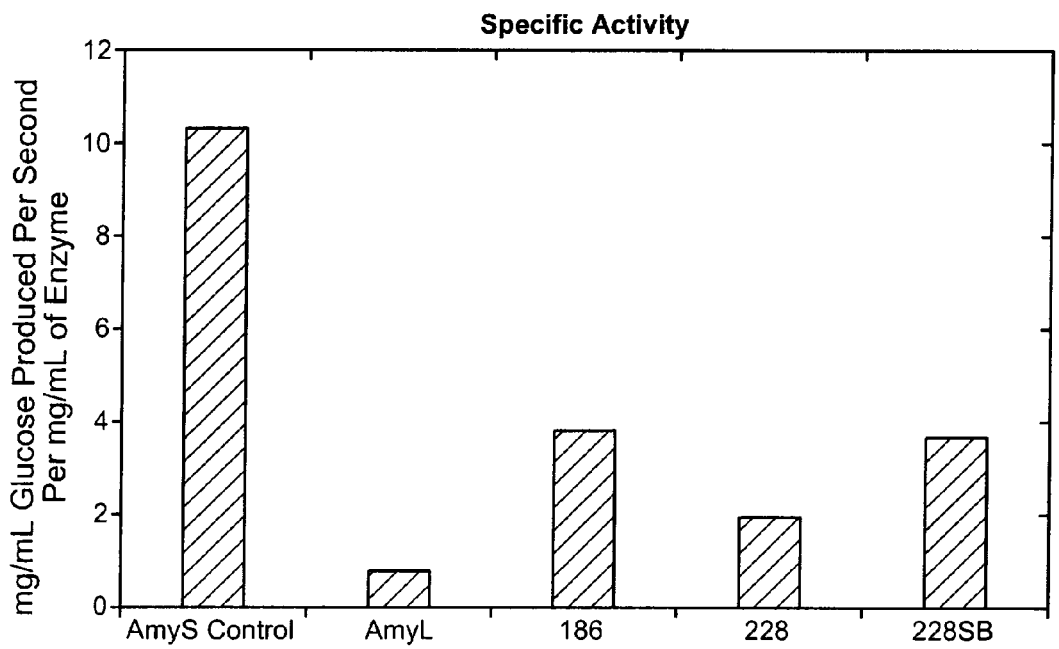
FIG. 5 shows the specific activity of several chimeric α-amylases at 75° C. The DNS reducing sugar detection assay, described below (see methods section for details), was used to determine the rate of reactions for chimeras 186, 228 and 228SB in comparison to the AmyL and the AmyS control enzyme. The specific activity is reported as mg glucose produced per second per mg enzyme in the reaction. All three chimeric enzymes tested showed greater specific activity than the AmyL enzyme at the elevated temperature, 75° C., tested.

Results and Discussion. The specific activity comparison results are shown in FIG. 5 as mg/mL glucose produced per second per mg/mL of enzyme. All three chimeric amylases showed significantly higher specific activity towards the substrate as compared to the AmyL amylase at this elevated temperature.

Example 6

Viscosity Changes with Hybrid Amylases

In this example, experiments were conducted to measure viscosity reduction in a viscometer for several chimeric amylases: 186, 228, 202SB and 228 SB, and for the AmyS control (SEQ ID NO: 3), at pH 5.8 using viscosity measurement assay as described, using a EUROSTAR/IKA Labortechnik Control-Visc P7 electronic overhead stirrer with torque read output.

Figure 6:
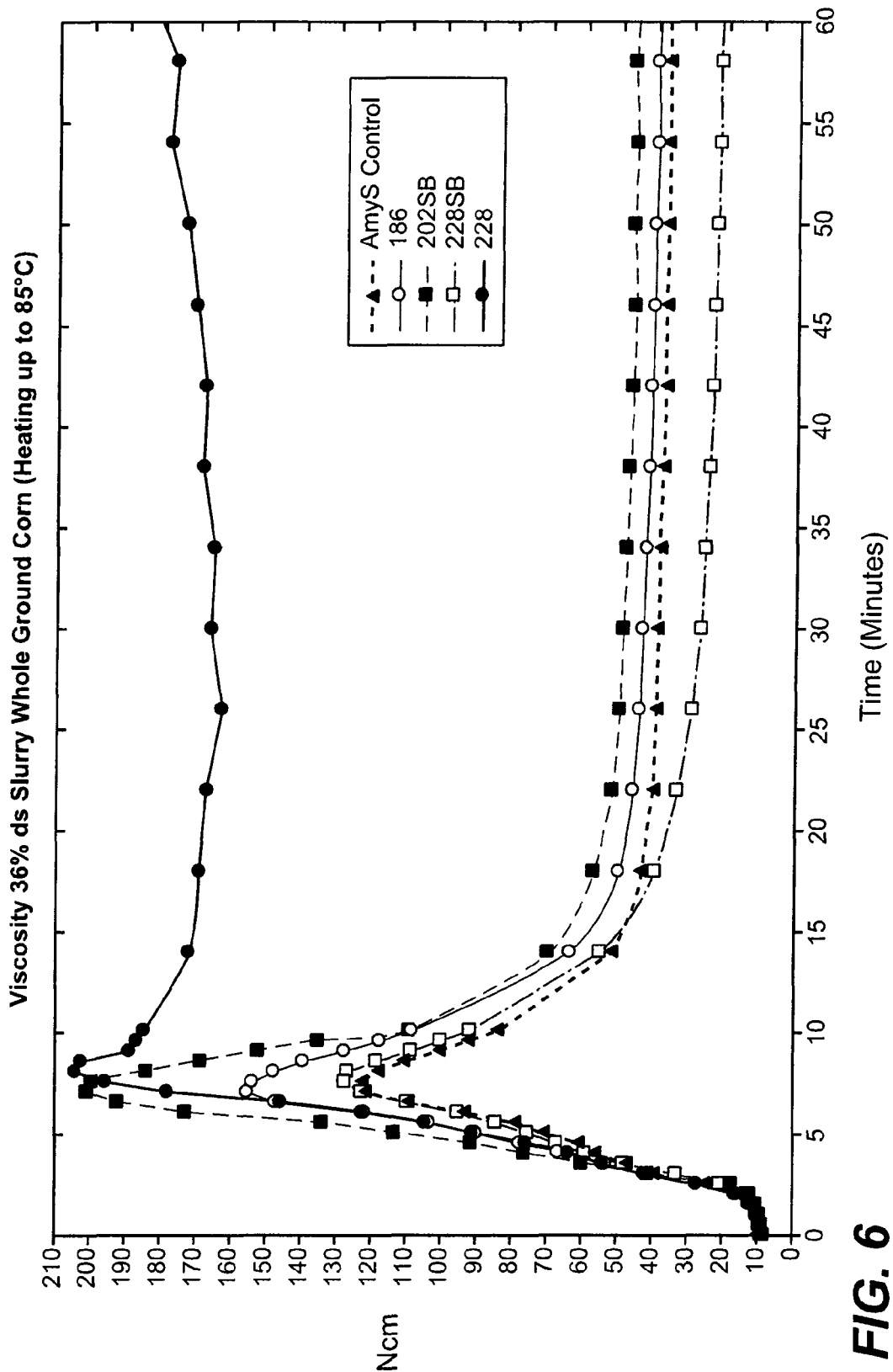
FIG. 6 shows the changes in viscosity of corn flour substrate upon incubation with various hybrid amylases. Hybrids 186, 202SB, 228SB, and 228 were compared to the AmyS control for their ability to reduce viscosity as measured by EUROSTAR/IKA Labortechnik control-visc P7 electronic overhead stirrer with torque read output.

Results and Discussion. FIG. 6 shows that viscosity reduction for whole corn substrate is observed for several of the amylase chimeras tested. Consistent with results observed for protein stability (FIG. 2), hybrid 186 performed comparably to the AmyS control in final viscosity. Chimera 228 had no effect on viscosity reduction under these conditions, consistent with its poor stability at high temperature (FIG. 2). Salt-bridged chimeras 202SB and 228 SB both showed reduction of viscosity in this assay. In the case of salt-bridged chimera 228SB, peak viscosity was the same as for the AmyS control, and final viscosity was lower than that observed for the AmyS control (FIG. 6), clearly showing a benefit in performance.

It will be apparent to those skilled in the art that the chimeric α-amylases and the methods of making and using those chimeric amylases can be varied or modified without departing from the scope or spirit or of this disclosure. Thus, such variations and modifications are included within the scope of the appended claims.

What is claimed is:

1. A chimeric polypeptide having at least about 95% sequence identity to SEQ ID NO:11, wherein said chimeric polypeptide has amylase catalytic activity and enhanced thermostability relative to a wild type AmyS amylase.

2. The chimeric polypeptide of claim 1 wherein the amylase catalytic activity is a retained amylase catalytic activity of at least 50% after incubation at 95° C. for 30 minutes.

3. The chimeric polypeptide of claim 2 that retains at least about 60% of its catalytic activity after incubation at 95° C. for 60 minutes.

4. The chimeric polypeptide of claim 3 which retains at least about 80% of its catalytic activity after incubation at 95° C. for 60 minutes.

5. A composition comprising the chimeric polypeptide of claim 1.

6. The composition of claim 5 further comprising one or more additional polypeptides.

7. The composition of claim 6, wherein the one or more additional polypeptides is an enzyme.

8. The composition of claim 5 that includes one or more detergents or cleaning agents.

9. The composition of claim 5 that is formulated for use in food or food processes.

10. A food-grade lyophilized composition comprising the composition of claim 5.

11. A method of liquefying a starch slurry comprising:
making a slurry comprising a starch,
heating the slurry to an acceptable temperature for liquefaction,
adding to the slurry, a composition comprising the composition of claim 5, and
incubating the slurry with the composition for a time and at a temperature sufficient to liquefy the starch slurry.

12. The method of claim 11, wherein the addition of the composition
reduces the peak viscosity of the slurry as well as the addition of an AmyS amylase used in a comparable liquefaction, and
reduces the final viscosity of the slurry as well as the addition of an AmyL amylase used in a comparable liquefaction.

13. The method of claim 12, wherein the temperature is at least about 80° C. to about 100° C.

14. The method of claim 11, wherein the slurry comprises about 15-40% starch on a dry-weight basis.

15. The method of claim 14, wherein the liquefaction is part of a fermentation.

16. The method of claim 15, wherein the fermentation is used to produce a food product, a food additive, a fuel, or a fuel additive.

17. The method of claim 16, wherein the fuel or fuel additive is an alcohol.

18. The method of claim 17, wherein the alcohol is ethanol.

19. A method of cleaning a surface to remove starch residue comprising the steps of providing a surface that has starch residue to be removed, contacting the surface with a composition of claim 5, for a time and at a temperature sufficient to result in removal of the starch residue.

20. The method of claim 19, wherein the composition comprises one or more of a protease, a lipase, an additional amylase, or a combination thereof.

21. The method of claim 20 further comprising a step of rinsing or bulk removal of residue prior to the contacting step.

22. The method of claim 19, wherein the temperature during the contacting step reaches at least 50-100° C.

23. A method of treating a woven material that has been previously subjected to contact with a coating comprising starch or a starch-derivative, the method comprising contacting the woven material with a solution comprising a composition according to claim 5 for a time and under conditions sufficient to substantially remove the coating from the woven material.

24. The method of claim 23, wherein the woven material is a fabric.

25. The method of claim 23, wherein the contacting step is performed at a pressure that is greater than ambient atmospheric pressure.

26. A kit for facilitating liquefaction of starch slurry, said kit comprising the chimeric polypeptide of claim 1, and
instructions for use of the kit in the liquefaction of a starch slurry.

* * * * *

SEQUENCE LISTING

<160> NUMBER OF SEQ ID NOS: 40

<210> SEQ ID NO 1
<211> LENGTH: 483
<212> TYPE: PRT
<213> ORGANISM: Bacillus licheniformis

<400> SEQUENCE: 1

```
Thr Asn Leu Asn Gly Thr Leu Met Gln Tyr Phe Glu Trp Tyr Thr Pro
  1               5                  10                  15

Asn Asp Gly Gln His Trp Lys Arg Leu Gln Asn Asp Ser Ala Tyr Leu
             20                  25                  30

Ala Glu His Gly Ile Thr Ala Val Trp Ile Pro Pro Ala Tyr Lys Gly
         35                  40                  45

Thr Ser Gln Ala Asp Val Gly Tyr Gly Ala Tyr Asp Leu Tyr Asp Leu
     50                  55                  60

Gly Glu Phe His Gln Lys Gly Thr Val Arg Thr Lys Tyr Gly Thr Lys
 65                  70                  75                  80

Gly Glu Leu Gln Ser Ala Ile Lys Ser Leu His Ser Arg Asp Ile Asn
                 85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu Tyr Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Ser Glu Asn Gly Asn
            180                 185                 190

Tyr Asp Tyr Leu Met Tyr Ala Asp Ile Asp Tyr Asp His Pro Asp Val
        195                 200                 205

Val Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365
```

```
Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
    450                 455                 460

Glu Gly Trp Gly Glu Phe His Val Asn Gly Gly Ser Val Ser Ile Tyr
465                 470                 475                 480

Val Gln Arg

<210> SEQ ID NO 2
<211> LENGTH: 486
<212> TYPE: PRT
<213> ORGANISM: Bacillus stearothermophilus

<400> SEQUENCE: 2

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255
```

Lys Pro Leu Phe Thr Val Gly Glu Tyr Trp Ser Tyr Asp Ile Asn Lys
                260                 265                 270

Leu His Asn Tyr Ile Thr Lys Thr Asn Gly Thr Met Ser Leu Phe Asp
            275                 280                 285

Ala Pro Leu His Asn Lys Phe Tyr Thr Ala Ser Lys Ser Gly Gly Ala
        290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
        370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
        450                 455                 460

Asp Gly Trp Gly Glu Phe Lys Val Asn Gly Gly Ser Val Ser Val Trp
465                 470                 475                 480

Val Pro Arg Lys Thr Thr
                485

<210> SEQ ID NO 3
<211> LENGTH: 484
<212> TYPE: PRT
<213> ORGANISM: Bacillus stearothermophilus

<400> SEQUENCE: 3

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Ile Gly Lys Ala Trp Asp Trp Glu Val Asp Thr Glu Asn Gly
            180                 185                 190

Asn Tyr Asp Tyr Leu Met Tyr Ala Asp Leu Asp Met Asp His Pro Glu
        195                 200                 205

Val Val Thr Glu Leu Lys Asn Trp Gly Lys Trp Tyr Val Asn Thr Thr
    210                 215                 220

Asn Ile Asp Gly Phe Arg Leu Asp Ala Val Lys His Ile Lys Phe Ser
225                 230                 235                 240

Phe Phe Pro Asp Trp Leu Ser Tyr Val Arg Ser Gln Thr Gly Lys Pro
                245                 250                 255

Leu Phe Thr Val Gly Glu Tyr Trp Ser Tyr Asp Ile Asn Lys Leu His
            260                 265                 270

Asn Tyr Ile Thr Lys Thr Asn Gly Thr Met Ser Leu Phe Asp Ala Pro
        275                 280                 285

Leu His Asn Lys Phe Tyr Thr Ala Ser Lys Ser Gly Gly Ala Phe Asp
    290                 295                 300

Met Arg Thr Leu Met Thr Asn Thr Leu Met Lys Asp Gln Pro Thr Leu
305                 310                 315                 320

Ala Val Thr Phe Val Asp Asn His Asp Thr Glu Pro Gly Gln Ala Leu
                325                 330                 335

Gln Ser Trp Val Asp Pro Trp Phe Lys Pro Leu Ala Tyr Ala Phe Ile
            340                 345                 350

Leu Thr Arg Gln Glu Gly Tyr Pro Cys Val Phe Tyr Gly Asp Tyr Tyr
        355                 360                 365

Gly Ile Pro Gln Tyr Asn Ile Pro Ser Leu Lys Ser Lys Ile Asp Pro
    370                 375                 380

Leu Leu Ile Ala Arg Arg Asp Tyr Ala Tyr Gly Thr Gln His Asp Tyr
385                 390                 395                 400

Leu Asp His Ser Asp Ile Ile Gly Trp Thr Arg Glu Gly Val Thr Glu
                405                 410                 415

Lys Pro Gly Ser Gly Leu Ala Ala Leu Ile Thr Asp Gly Pro Gly Gly
            420                 425                 430

Ser Lys Trp Met Tyr Val Gly Lys Gln His Ala Gly Lys Val Phe Tyr
        435                 440                 445

Asp Leu Thr Gly Asn Arg Ser Asp Thr Val Thr Ile Asn Ser Asp Gly
    450                 455                 460

Trp Gly Glu Phe Lys Val Asn Gly Gly Ser Val Ser Val Trp Val Pro
465                 470                 475                 480

Arg Lys Thr Thr

<210> SEQ ID NO 4
<211> LENGTH: 483
<212> TYPE: PRT
<213> ORGANISM: Artificial
<220> FEATURE:
<223> OTHER INFORMATION: Hybrid comprising N-terminal portion of AmyL
      through position 186, and C-terminal portion from AmyS

<400> SEQUENCE: 4

Thr Asn Leu Asn Gly Thr Leu Met Gln Tyr Phe Glu Trp Tyr Thr Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu Tyr Leu Ile Lys Ala Trp Thr His Phe His Phe Pro
130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
            165                 170                 175

Phe Gln Gly Lys Ala Trp Asp Trp Glu Val Asp Thr Glu Asn Gly Asn
        180                 185                 190

Tyr Asp Tyr Leu Met Tyr Ala Asp Leu Asp Met Asp His Pro Glu Val
        195                 200                 205

Val Thr Glu Leu Lys Asn Trp Gly Lys Trp Tyr Val Asn Thr Thr Asn
210                 215                 220

Ile Asp Gly Phe Arg Leu Asp Ala Val Lys His Ile Lys Phe Ser Phe
225                 230                 235                 240

Phe Pro Asp Trp Leu Ser Tyr Val Arg Ser Gln Thr Gly Lys Pro Leu
            245                 250                 255

Phe Thr Val Gly Glu Tyr Trp Ser Tyr Asp Ile Asn Lys Leu His Asn
        260                 265                 270

Tyr Ile Thr Lys Thr Asn Gly Thr Met Ser Leu Phe Asp Ala Pro Leu
        275                 280                 285

His Asn Lys Phe Tyr Thr Ala Ser Lys Ser Gly Gly Ala Phe Asp Met
290                 295                 300

Arg Thr Leu Met Thr Asn Thr Leu Met Lys Asp Gln Pro Thr Leu Ala
305                 310                 315                 320

Val Thr Phe Val Asp Asn His Asp Thr Glu Pro Gly Gln Ala Leu Gln
            325                 330                 335

Ser Trp Val Asp Pro Trp Phe Lys Pro Leu Ala Tyr Ala Phe Ile Leu
        340                 345                 350

Thr Arg Gln Glu Gly Tyr Pro Cys Val Phe Tyr Gly Asp Tyr Tyr Gly
        355                 360                 365

Ile Pro Gln Tyr Asn Ile Pro Ser Leu Lys Ser Lys Ile Asp Pro Leu
370                 375                 380

Leu Ile Ala Arg Arg Asp Tyr Ala Tyr Gly Thr Gln His Asp Tyr Leu
385                 390                 395                 400

Asp His Ser Asp Ile Ile Gly Trp Thr Arg Glu Gly Val Thr Glu Lys
            405                 410                 415

Pro Gly Ser Gly Leu Ala Ala Leu Ile Thr Asp Gly Pro Gly Gly Ser
        420                 425                 430

```
Lys Trp Met Tyr Val Gly Lys Gln His Ala Gly Lys Val Phe Tyr Asp
            435                 440                 445

Leu Thr Gly Asn Arg Ser Asp Thr Val Thr Ile Asn Ser Asp Gly Trp
    450                 455                 460

Gly Glu Phe Lys Val Asn Gly Gly Ser Val Ser Val Trp Val Pro Arg
465                 470                 475                 480

Lys Thr Thr

<210> SEQ ID NO 5
<211> LENGTH: 483
<212> TYPE: PRT
<213> ORGANISM: Artificial
<220> FEATURE:
<223> OTHER INFORMATION: Hybrid comprising N-terminal portion of AmyL
      through position 187, and C-terminal portion from AmyS

<400> SEQUENCE: 5

Thr Asn Leu Asn Gly Thr Leu Met Gln Tyr Phe Glu Trp Tyr Thr Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
            85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu Tyr Leu Ile Lys Ala Trp Thr His Phe His Phe Pro
130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
            165                 170                 175

Phe Gln Gly Lys Ala Trp Asp Trp Glu Val Ser Thr Glu Asn Gly Asn
        180                 185                 190

Tyr Asp Tyr Leu Met Tyr Ala Asp Leu Asp Met Asp His Pro Glu Val
    195                 200                 205

Val Thr Glu Leu Lys Asn Trp Gly Lys Trp Tyr Val Asn Thr Thr Asn
210                 215                 220

Ile Asp Gly Phe Arg Leu Asp Ala Val Lys His Ile Lys Phe Ser Phe
225                 230                 235                 240

Phe Pro Asp Trp Leu Ser Tyr Val Arg Ser Gln Thr Gly Lys Pro Leu
            245                 250                 255

Phe Thr Val Gly Glu Tyr Trp Ser Tyr Asp Ile Asn Lys Leu His Asn
        260                 265                 270

Tyr Ile Thr Lys Thr Asn Gly Thr Met Ser Leu Phe Asp Ala Pro Leu
    275                 280                 285

His Asn Lys Phe Tyr Thr Ala Ser Lys Ser Gly Gly Ala Phe Asp Met
290                 295                 300
```

```
Arg Thr Leu Met Thr Asn Thr Leu Met Lys Asp Gln Pro Thr Leu Ala
305                 310                 315                 320

Val Thr Phe Val Asp Asn His Asp Thr Glu Pro Gly Gln Ala Leu Gln
            325                 330                 335

Ser Trp Val Asp Pro Trp Phe Lys Pro Leu Ala Tyr Ala Phe Ile Leu
            340                 345                 350

Thr Arg Gln Glu Gly Tyr Pro Cys Val Phe Tyr Gly Asp Tyr Tyr Gly
        355                 360                 365

Ile Pro Gln Tyr Asn Ile Pro Ser Leu Lys Ser Lys Ile Asp Pro Leu
    370                 375                 380

Leu Ile Ala Arg Arg Asp Tyr Ala Tyr Gly Thr Gln His Asp Tyr Leu
385                 390                 395                 400

Asp His Ser Asp Ile Ile Gly Trp Thr Arg Glu Gly Val Thr Glu Lys
                405                 410                 415

Pro Gly Ser Gly Leu Ala Ala Leu Ile Thr Asp Gly Pro Gly Gly Ser
                420                 425                 430

Lys Trp Met Tyr Val Gly Lys Gln His Ala Gly Lys Val Phe Tyr Asp
            435                 440                 445

Leu Thr Gly Asn Arg Ser Asp Thr Val Thr Ile Asn Ser Asp Gly Trp
450                 455                 460

Gly Glu Phe Lys Val Asn Gly Gly Ser Val Ser Val Trp Val Pro Arg
465                 470                 475                 480

Lys Thr Thr

<210> SEQ ID NO 6
<211> LENGTH: 483
<212> TYPE: PRT
<213> ORGANISM: Artificial
<220> FEATURE:
<223> OTHER INFORMATION: Hybrid comprising N-terminal portion of AmyL
      through position 200, and C-terminal portion from AmyS

<400> SEQUENCE: 6

Thr Asn Leu Asn Gly Thr Leu Met Gln Tyr Phe Glu Trp Tyr Thr Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu Tyr Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175
```

```
Phe Gln Gly Lys Ala Trp Asp Trp Glu Val Ser Ser Glu Asn Gly Asn
                180                 185                 190

Tyr Asp Tyr Leu Met Tyr Ala Asp Leu Asp Met Asp His Pro Glu Val
            195                 200                 205

Val Thr Glu Leu Lys Asn Trp Gly Lys Trp Tyr Val Asn Thr Thr Asn
210                 215                 220

Ile Asp Gly Phe Arg Leu Asp Ala Val Lys His Ile Lys Phe Ser Phe
225                 230                 235                 240

Phe Pro Asp Trp Leu Ser Tyr Val Arg Ser Gln Thr Gly Lys Pro Leu
                245                 250                 255

Phe Thr Val Gly Glu Tyr Trp Ser Tyr Asp Ile Asn Lys Leu His Asn
                260                 265                 270

Tyr Ile Thr Lys Thr Asn Gly Thr Met Ser Leu Phe Asp Ala Pro Leu
            275                 280                 285

His Asn Lys Phe Tyr Thr Ala Ser Lys Ser Gly Gly Ala Phe Asp Met
        290                 295                 300

Arg Thr Leu Met Thr Asn Thr Leu Met Lys Asp Gln Pro Thr Leu Ala
305                 310                 315                 320

Val Thr Phe Val Asp Asn His Asp Thr Glu Pro Gly Gln Ala Leu Gln
                325                 330                 335

Ser Trp Val Asp Pro Trp Phe Lys Pro Leu Ala Tyr Ala Phe Ile Leu
                340                 345                 350

Thr Arg Gln Glu Gly Tyr Pro Cys Val Phe Tyr Gly Asp Tyr Tyr Gly
            355                 360                 365

Ile Pro Gln Tyr Asn Ile Pro Ser Leu Lys Ser Lys Ile Asp Pro Leu
370                 375                 380

Leu Ile Ala Arg Arg Asp Tyr Ala Tyr Gly Thr Gln His Asp Tyr Leu
385                 390                 395                 400

Asp His Ser Asp Ile Ile Gly Trp Thr Arg Glu Gly Val Thr Glu Lys
                405                 410                 415

Pro Gly Ser Gly Leu Ala Ala Leu Ile Thr Asp Gly Pro Gly Gly Ser
                420                 425                 430

Lys Trp Met Tyr Val Gly Lys Gln His Ala Gly Lys Val Phe Tyr Asp
            435                 440                 445

Leu Thr Gly Asn Arg Ser Asp Thr Val Thr Ile Asn Ser Asp Gly Trp
450                 455                 460

Gly Glu Phe Lys Val Asn Gly Gly Ser Val Ser Val Trp Val Pro Arg
465                 470                 475                 480

Lys Thr Thr

<210> SEQ ID NO 7
<211> LENGTH: 483
<212> TYPE: PRT
<213> ORGANISM: Artificial
<220> FEATURE:
<223> OTHER INFORMATION: Hybrid comprising N-terminal portion of AmyL
      through position 200, and C-terminal portion from AmyS

<400> SEQUENCE: 7

Thr Asn Leu Asn Gly Thr Leu Met Gln Tyr Phe Glu Trp Tyr Thr Pro
1               5                   10                  15

Asn Asp Gly Gln His Trp Lys Arg Leu Gln Asn Asp Ser Ala Tyr Leu
                20                  25                  30

Ala Glu His Gly Ile Thr Ala Val Trp Ile Pro Pro Ala Tyr Lys Gly
            35                  40                  45
```

```
Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Ala Asp Ala Thr
                100                 105                 110

Glu Asp Val Thr Ala Val Glu Val Asp Pro Ala Asp Arg Asn Arg Val
                115                 120                 125

Ile Ser Gly Glu Tyr Leu Ile Lys Ala Trp Thr His Phe His Phe Pro
130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Asp Thr Glu Asn Gly Asn
                180                 185                 190

Tyr Asp Tyr Leu Met Tyr Ala Asp Leu Asp Met Asp His Pro Glu Val
                195                 200                 205

Val Thr Glu Leu Lys Asn Trp Gly Lys Trp Tyr Val Asn Thr Thr Asn
210                 215                 220

Ile Asp Gly Phe Arg Leu Asp Ala Val Lys His Ile Lys Phe Ser Phe
225                 230                 235                 240

Phe Pro Asp Trp Leu Ser Tyr Val Arg Ser Gln Thr Gly Lys Pro Leu
                245                 250                 255

Phe Thr Val Gly Glu Tyr Trp Ser Tyr Asp Ile Asn Lys Leu His Asn
                260                 265                 270

Tyr Ile Thr Lys Thr Asn Gly Thr Met Ser Leu Phe Asp Ala Pro Leu
                275                 280                 285

His Asn Lys Phe Tyr Thr Ala Ser Lys Ser Gly Gly Ala Phe Asp Met
                290                 295                 300

Arg Thr Leu Met Thr Asn Thr Leu Met Lys Asp Gln Pro Thr Leu Ala
305                 310                 315                 320

Val Thr Phe Val Asp Asn His Asp Thr Glu Pro Gly Gln Ala Leu Gln
                325                 330                 335

Ser Trp Val Asp Pro Trp Phe Lys Pro Leu Ala Tyr Ala Phe Ile Leu
                340                 345                 350

Thr Arg Gln Glu Gly Tyr Pro Cys Val Phe Tyr Gly Asp Tyr Tyr Gly
                355                 360                 365

Ile Pro Gln Tyr Asn Ile Pro Ser Leu Lys Ser Lys Ile Asp Pro Leu
                370                 375                 380

Leu Ile Ala Arg Arg Asp Tyr Ala Tyr Gly Thr Gln His Asp Tyr Leu
385                 390                 395                 400

Asp His Ser Asp Ile Ile Gly Trp Thr Arg Glu Gly Val Thr Glu Lys
                405                 410                 415

Pro Gly Ser Gly Leu Ala Ala Leu Ile Thr Asp Gly Pro Gly Gly Ser
                420                 425                 430

Lys Trp Met Tyr Val Gly Lys Gln His Ala Gly Lys Val Phe Tyr Asp
                435                 440                 445

Leu Thr Gly Asn Arg Ser Asp Thr Val Thr Ile Asn Ser Asp Gly Trp
450                 455                 460

Gly Glu Phe Lys Val Asn Gly Gly Ser Val Ser Val Trp Val Pro Arg
```

```
                465                 470                 475                 480
Lys Thr Thr

<210> SEQ ID NO 8
<211> LENGTH: 483
<212> TYPE: PRT
<213> ORGANISM: Artificial
<220> FEATURE:
<223> OTHER INFORMATION: Hybrid comprising N-terminal portion of AmyL
      through position 202, and C-terminal portion from AmyS

<400> SEQUENCE: 8

Thr Asn Leu Asn Gly Thr Leu Met Gln Tyr Phe Glu Trp Tyr Thr Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu Tyr Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Ser Glu Asn Gly Asn
            180                 185                 190

Tyr Asp Tyr Leu Met Tyr Ala Asp Ile Asp Met Asp His Pro Glu Val
        195                 200                 205

Val Thr Glu Leu Lys Asn Trp Gly Lys Trp Tyr Val Asn Thr Thr Asn
    210                 215                 220

Ile Asp Gly Phe Arg Leu Asp Ala Val Lys His Ile Lys Phe Ser Phe
225                 230                 235                 240

Phe Pro Asp Trp Leu Ser Tyr Val Arg Ser Gln Thr Gly Lys Pro Leu
                245                 250                 255

Phe Thr Val Gly Glu Tyr Trp Ser Tyr Asp Ile Asn Lys Leu His Asn
            260                 265                 270

Tyr Ile Thr Lys Thr Asn Gly Thr Met Ser Leu Phe Asp Ala Pro Leu
        275                 280                 285

His Asn Lys Phe Tyr Thr Ala Ser Lys Ser Gly Gly Ala Phe Asp Met
    290                 295                 300

Arg Thr Leu Met Thr Asn Thr Leu Met Lys Asp Gln Pro Thr Leu Ala
305                 310                 315                 320

Val Thr Phe Val Asp Asn His Asp Thr Glu Pro Gly Gln Ala Leu Gln
                325                 330                 335

Ser Trp Val Asp Pro Trp Phe Lys Pro Leu Ala Tyr Ala Phe Ile Leu
```

```
                    340                 345                 350
Thr Arg Gln Glu Gly Tyr Pro Cys Val Phe Tyr Gly Asp Tyr Tyr Gly
            355                 360                 365

Ile Pro Gln Tyr Asn Ile Pro Ser Leu Lys Ser Lys Ile Asp Pro Leu
        370                 375                 380

Leu Ile Ala Arg Arg Asp Tyr Ala Tyr Gly Thr Gln His Asp Tyr Leu
385                 390                 395                 400

Asp His Ser Asp Ile Ile Gly Trp Thr Arg Glu Gly Val Thr Glu Lys
                405                 410                 415

Pro Gly Ser Gly Leu Ala Ala Leu Ile Thr Asp Gly Pro Gly Gly Ser
            420                 425                 430

Lys Trp Met Tyr Val Gly Lys Gln His Ala Gly Lys Val Phe Tyr Asp
        435                 440                 445

Leu Thr Gly Asn Arg Ser Asp Thr Val Thr Ile Asn Ser Asp Gly Trp
    450                 455                 460

Gly Glu Phe Lys Val Asn Gly Gly Ser Val Ser Val Trp Val Pro Arg
465                 470                 475                 480

Lys Thr Thr

<210> SEQ ID NO 9
<211> LENGTH: 483
<212> TYPE: PRT
<213> ORGANISM: Artificial
<220> FEATURE:
<223> OTHER INFORMATION: Hybrid comprising N-terminal portion of AmyL
      through position 202, and C-terminal portion from AmyS

<400> SEQUENCE: 9

Thr Asn Leu Asn Gly Thr Leu Met Gln Tyr Phe Glu Trp Tyr Thr Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu Tyr Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Asp Thr Glu Asn Gly Asn
            180                 185                 190

Tyr Asp Tyr Leu Met Tyr Ala Asp Ile Asp Met Asp His Pro Glu Val
        195                 200                 205

Val Thr Glu Leu Lys Asn Trp Gly Lys Trp Tyr Val Asn Thr Thr Asn
```

```
                    210                 215                 220
Ile Asp Gly Phe Arg Leu Asp Ala Val Lys His Ile Lys Phe Ser Phe
225                 230                 235                 240

Phe Pro Asp Trp Leu Ser Tyr Val Arg Ser Gln Thr Gly Lys Pro Leu
                245                 250                 255

Phe Thr Val Gly Glu Tyr Trp Ser Tyr Asp Ile Asn Lys Leu His Asn
                260                 265                 270

Tyr Ile Thr Lys Thr Asn Gly Thr Met Ser Leu Phe Asp Ala Pro Leu
                275                 280                 285

His Asn Lys Phe Tyr Thr Ala Ser Lys Ser Gly Gly Ala Phe Asp Met
            290                 295                 300

Arg Thr Leu Met Thr Asn Thr Leu Met Lys Asp Gln Pro Thr Leu Ala
305                 310                 315                 320

Val Thr Phe Val Asp Asn His Asp Thr Glu Pro Gly Gln Ala Leu Gln
                325                 330                 335

Ser Trp Val Asp Pro Trp Phe Lys Pro Leu Ala Tyr Ala Phe Ile Leu
                340                 345                 350

Thr Arg Gln Glu Gly Tyr Pro Cys Val Phe Tyr Gly Asp Tyr Tyr Gly
            355                 360                 365

Ile Pro Gln Tyr Asn Ile Pro Ser Leu Lys Ser Lys Ile Asp Pro Leu
                370                 375                 380

Leu Ile Ala Arg Arg Asp Tyr Ala Tyr Gly Thr Gln His Asp Tyr Leu
385                 390                 395                 400

Asp His Ser Asp Ile Ile Gly Trp Thr Arg Glu Gly Val Thr Glu Lys
                405                 410                 415

Pro Gly Ser Gly Leu Ala Ala Leu Ile Thr Asp Gly Pro Gly Gly Ser
                420                 425                 430

Lys Trp Met Tyr Val Gly Lys Gln His Ala Gly Lys Val Phe Tyr Asp
            435                 440                 445

Leu Thr Gly Asn Arg Ser Asp Thr Val Thr Ile Asn Ser Asp Gly Trp
450                 455                 460

Gly Glu Phe Lys Val Asn Gly Gly Ser Val Ser Val Trp Val Pro Arg
465                 470                 475                 480

Lys Thr Thr

<210> SEQ ID NO 10
<211> LENGTH: 483
<212> TYPE: PRT
<213> ORGANISM: Artificial
<220> FEATURE:
<223> OTHER INFORMATION: Hybrid comprising N-terminal portion of AmyL
      through position 228, and C-terminal portion from AmyS

<400> SEQUENCE: 10

Thr Asn Leu Asn Gly Thr Leu Met Gln Tyr Phe Glu Trp Tyr Thr Pro
1               5                   10                  15

Asn Asp Gly Gln His Trp Lys Arg Leu Gln Asn Asp Ser Ala Tyr Leu
                20                  25                  30

Ala Glu His Gly Ile Thr Ala Val Trp Ile Pro Pro Ala Tyr Lys Gly
            35                  40                  45

Thr Ser Gln Ala Asp Val Gly Tyr Gly Ala Tyr Asp Leu Tyr Asp Leu
        50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
```

```
                85                  90                  95
Val Tyr Gly Asp Val Val Ile Asn His Lys Gly Gly Ala Asp Ala Thr
                100                 105                 110

Glu Asp Val Thr Ala Val Glu Val Asp Pro Ala Asp Arg Asn Arg Val
                115                 120                 125

Ile Ser Gly Glu Tyr Leu Ile Lys Ala Trp Thr His Phe His Phe Pro
                130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Ser Glu Asn Gly Asn
                180                 185                 190

Tyr Asp Tyr Leu Met Tyr Ala Asp Ile Asp Tyr Asp His Pro Asp Val
                195                 200                 205

Val Ala Glu Ile Lys Arg Trp Gly Thr Trp Tyr Ala Asn Glu Leu Gln
                210                 215                 220

Leu Asp Gly Phe Arg Leu Asp Ala Val Lys His Ile Lys Phe Ser Phe
225                 230                 235                 240

Phe Pro Asp Trp Leu Ser Tyr Val Arg Ser Gln Thr Gly Lys Pro Leu
                245                 250                 255

Phe Thr Val Gly Glu Tyr Trp Ser Tyr Asp Ile Asn Lys Leu His Asn
                260                 265                 270

Tyr Ile Thr Lys Thr Asn Gly Thr Met Ser Leu Phe Asp Ala Pro Leu
                275                 280                 285

His Asn Lys Phe Tyr Thr Ala Ser Lys Ser Gly Gly Ala Phe Asp Met
                290                 295                 300

Arg Thr Leu Met Thr Asn Thr Leu Met Lys Asp Gln Pro Thr Leu Ala
305                 310                 315                 320

Val Thr Phe Val Asp Asn His Asp Thr Glu Pro Gly Gln Ala Leu Gln
                325                 330                 335

Ser Trp Val Asp Pro Trp Phe Lys Pro Leu Ala Tyr Ala Phe Ile Leu
                340                 345                 350

Thr Arg Gln Glu Gly Tyr Pro Cys Val Phe Tyr Gly Asp Tyr Tyr Gly
                355                 360                 365

Ile Pro Gln Tyr Asn Ile Pro Ser Leu Lys Ser Lys Ile Asp Pro Leu
                370                 375                 380

Leu Ile Ala Arg Arg Asp Tyr Ala Tyr Gly Thr Gln His Asp Tyr Leu
385                 390                 395                 400

Asp His Ser Asp Ile Ile Gly Trp Thr Arg Glu Gly Val Thr Glu Lys
                405                 410                 415

Pro Gly Ser Gly Leu Ala Ala Leu Ile Thr Asp Gly Pro Gly Gly Ser
                420                 425                 430

Lys Trp Met Tyr Val Gly Lys Gln His Ala Gly Lys Val Phe Tyr Asp
                435                 440                 445

Leu Thr Gly Asn Arg Ser Asp Thr Val Thr Ile Asn Ser Asp Gly Trp
                450                 455                 460

Gly Glu Phe Lys Val Asn Gly Gly Ser Val Ser Val Trp Val Pro Arg
465                 470                 475                 480

Lys Thr Thr

<210> SEQ ID NO 11
<211> LENGTH: 483
```

```
<212> TYPE: PRT
<213> ORGANISM: Artificial
<220> FEATURE:
<223> OTHER INFORMATION: Hybrid comprising N-terminal portion of AmyL
      through position 228, and C-terminal portion from AmyS

<400> SEQUENCE: 11
```

Thr Asn Leu Asn Gly Thr Leu Met Gln Tyr Phe Glu Trp Tyr Thr Pro
 1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu Tyr Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Asp Thr Glu Asn Gly Asn
            180                 185                 190

Tyr Asp Tyr Leu Met Tyr Ala Asp Ile Asp Tyr Asp His Pro Asp Val
        195                 200                 205

Val Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Phe Pro Asp Trp Leu Ser Tyr Val Arg Ser Gln Thr Gly Lys Pro Leu
                245                 250                 255

Phe Thr Val Gly Glu Tyr Trp Ser Tyr Asp Ile Asn Lys Leu His Asn
            260                 265                 270

Tyr Ile Thr Lys Thr Asn Gly Thr Met Ser Leu Phe Asp Ala Pro Leu
        275                 280                 285

His Asn Lys Phe Tyr Thr Ala Ser Lys Ser Gly Gly Ala Phe Asp Met
    290                 295                 300

Arg Thr Leu Met Thr Asn Thr Leu Met Lys Asp Gln Pro Thr Leu Ala
305                 310                 315                 320

Val Thr Phe Val Asp Asn His Asp Thr Glu Pro Gly Gln Ala Leu Gln
                325                 330                 335

Ser Trp Val Asp Pro Trp Phe Lys Pro Leu Ala Tyr Ala Phe Ile Leu
            340                 345                 350

Thr Arg Gln Glu Gly Tyr Pro Cys Val Phe Tyr Gly Asp Tyr Tyr Gly
        355                 360                 365

Ile Pro Gln Tyr Asn Ile Pro Ser Leu Lys Ser Lys Ile Asp Pro Leu
    370                 375                 380

```
Leu Ile Ala Arg Arg Asp Tyr Ala Tyr Gly Thr Gln His Asp Tyr Leu
385                 390                 395                 400

Asp His Ser Asp Ile Ile Gly Trp Thr Arg Glu Gly Val Thr Glu Lys
                405                 410                 415

Pro Gly Ser Gly Leu Ala Ala Leu Ile Thr Asp Gly Pro Gly Gly Ser
            420                 425                 430

Lys Trp Met Tyr Val Gly Lys Gln His Ala Gly Lys Val Phe Tyr Asp
        435                 440                 445

Leu Thr Gly Asn Arg Ser Asp Thr Val Thr Ile Asn Ser Asp Gly Trp
    450                 455                 460

Gly Glu Phe Lys Val Asn Gly Ser Val Ser Val Trp Val Pro Arg
465                 470                 475                 480

Lys Thr Thr

<210> SEQ ID NO 12
<211> LENGTH: 483
<212> TYPE: PRT
<213> ORGANISM: Artificial
<220> FEATURE:
<223> OTHER INFORMATION: Hybrid comprising N-terminal portion of AmyL
      through position 249, and C-terminal portion from AmyS

<400> SEQUENCE: 12

Thr Asn Leu Asn Gly Thr Leu Met Gln Tyr Phe Glu Trp Tyr Thr Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
            85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu Tyr Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Ser Glu Asn Gly Asn
            180                 185                 190

Tyr Asp Tyr Leu Met Tyr Ala Asp Ile Asp Tyr Asp His Pro Asp Val
        195                 200                 205

Val Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Ser Gln Thr Gly Lys Pro Leu
                245                 250                 255
```

-continued

```
Phe Thr Val Gly Glu Tyr Trp Ser Tyr Asp Ile Asn Lys Leu His Asn
            260                 265                 270
Tyr Ile Thr Lys Thr Asn Gly Thr Met Ser Leu Phe Asp Ala Pro Leu
            275                 280                 285
His Asn Lys Phe Tyr Thr Ala Ser Lys Ser Gly Gly Ala Phe Asp Met
            290                 295                 300
Arg Thr Leu Met Thr Asn Thr Leu Met Lys Asp Gln Pro Thr Leu Ala
305                 310                 315                 320
Val Thr Phe Val Asp Asn His Asp Thr Glu Pro Gly Gln Ala Leu Gln
                325                 330                 335
Ser Trp Val Asp Pro Trp Phe Lys Pro Leu Ala Tyr Ala Phe Ile Leu
            340                 345                 350
Thr Arg Gln Glu Gly Tyr Pro Cys Val Phe Tyr Gly Asp Tyr Tyr Gly
            355                 360                 365
Ile Pro Gln Tyr Asn Ile Pro Ser Leu Lys Ser Lys Ile Asp Pro Leu
            370                 375                 380
Leu Ile Ala Arg Arg Asp Tyr Ala Tyr Gly Thr Gln His Asp Tyr Leu
385                 390                 395                 400
Asp His Ser Asp Ile Ile Gly Trp Thr Arg Glu Gly Val Thr Glu Lys
                405                 410                 415
Pro Gly Ser Gly Leu Ala Ala Leu Ile Thr Asp Gly Pro Gly Gly Ser
            420                 425                 430
Lys Trp Met Tyr Val Gly Lys Gln His Ala Gly Lys Val Phe Tyr Asp
            435                 440                 445
Leu Thr Gly Asn Arg Ser Asp Thr Val Thr Ile Asn Ser Asp Gly Trp
            450                 455                 460
Gly Glu Phe Lys Val Asn Gly Gly Ser Val Ser Val Trp Val Pro Arg
465                 470                 475                 480
Lys Thr Thr

<210> SEQ ID NO 13
<211> LENGTH: 483
<212> TYPE: PRT
<213> ORGANISM: Artificial
<220> FEATURE:
<223> OTHER INFORMATION: Hybrid comprising N-terminal portion of AmyL
      through position 249, and C-terminal portion from AmyS

<400> SEQUENCE: 13

Thr Asn Leu Asn Gly Thr Leu Met Gln Tyr Phe Glu Trp Tyr Thr Pro
1               5                   10                  15
Asn Asp Gly Gln His Trp Lys Arg Leu Gln Asn Asp Ser Ala Tyr Leu
            20                  25                  30
Ala Glu His Gly Ile Thr Ala Val Trp Ile Pro Pro Ala Tyr Lys Gly
            35                  40                  45
Thr Ser Gln Ala Asp Val Gly Tyr Gly Ala Tyr Asp Leu Tyr Asp Leu
            50                  55                  60
Gly Glu Phe His Gln Lys Gly Thr Val Arg Thr Lys Tyr Gly Thr Lys
65                  70                  75                  80
Gly Glu Leu Gln Ser Ala Ile Lys Ser Leu His Ser Arg Asp Ile Asn
            85                  90                  95
Val Tyr Gly Asp Val Val Ile Asn His Lys Gly Gly Ala Asp Ala Thr
            100                 105                 110
Glu Asp Val Thr Ala Val Glu Val Asp Pro Ala Asp Arg Asn Arg Val
            115                 120                 125
```

Ile Ser Gly Glu Tyr Leu Ile Lys Ala Trp Thr His Phe His Phe Pro
130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Asp Thr Glu Asn Gly Asn
                180                 185                 190

Tyr Asp Tyr Leu Met Tyr Ala Asp Ile Asp Tyr Asp His Pro Asp Val
                195                 200                 205

Val Ala Glu Ile Lys Arg Trp Gly Thr Trp Tyr Ala Asn Glu Leu Gln
210                 215                 220

Leu Asp Gly Phe Arg Leu Asp Ala Val Lys His Ile Lys Phe Ser Phe
225                 230                 235                 240

Leu Arg Asp Trp Val Asn His Val Arg Ser Gln Thr Gly Lys Pro Leu
                245                 250                 255

Phe Thr Val Gly Glu Tyr Trp Ser Tyr Asp Ile Asn Lys Leu His Asn
                260                 265                 270

Tyr Ile Thr Lys Thr Asn Gly Thr Met Ser Leu Phe Asp Ala Pro Leu
                275                 280                 285

His Asn Lys Phe Tyr Thr Ala Ser Lys Ser Gly Gly Ala Phe Asp Met
290                 295                 300

Arg Thr Leu Met Thr Asn Thr Leu Met Lys Asp Gln Pro Thr Leu Ala
305                 310                 315                 320

Val Thr Phe Val Asp Asn His Asp Thr Glu Pro Gly Gln Ala Leu Gln
                325                 330                 335

Ser Trp Val Asp Pro Trp Phe Lys Pro Leu Ala Tyr Ala Phe Ile Leu
                340                 345                 350

Thr Arg Gln Glu Gly Tyr Pro Cys Val Phe Tyr Gly Asp Tyr Tyr Gly
                355                 360                 365

Ile Pro Gln Tyr Asn Ile Pro Ser Leu Lys Ser Lys Ile Asp Pro Leu
                370                 375                 380

Leu Ile Ala Arg Arg Asp Tyr Ala Tyr Gly Thr Gln His Asp Tyr Leu
385                 390                 395                 400

Asp His Ser Asp Ile Ile Gly Trp Thr Arg Glu Gly Val Thr Glu Lys
                405                 410                 415

Pro Gly Ser Gly Leu Ala Ala Leu Ile Thr Asp Gly Pro Gly Gly Ser
                420                 425                 430

Lys Trp Met Tyr Val Gly Lys Gln His Ala Gly Lys Val Phe Tyr Asp
                435                 440                 445

Leu Thr Gly Asn Arg Ser Asp Thr Val Thr Ile Asn Ser Asp Gly Trp
450                 455                 460

Gly Glu Phe Lys Val Asn Gly Gly Ser Val Ser Val Trp Val Pro Arg
465                 470                 475                 480

Lys Thr Thr

<210> SEQ ID NO 14
<211> LENGTH: 483
<212> TYPE: PRT
<213> ORGANISM: Artificial
<220> FEATURE:
<223> OTHER INFORMATION: Hybrid comprising N-terminal portion of AmyL
      through position 254, and C-terminal portion from AmyS

<400> SEQUENCE: 14

-continued

```
Thr Asn Leu Asn Gly Thr Leu Met Gln Tyr Phe Glu Trp Tyr Thr Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
            35                  40                  45

Thr Ser Gln Ala Asp Val Gly Tyr Gly Ala Tyr Asp Leu Tyr Asp Leu
            50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
            115                 120                 125

Ile Ser Gly Glu Tyr Leu Ile Lys Ala Trp Thr His Phe His Phe Pro
            130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Ser Glu Asn Gly Asn
            180                 185                 190

Tyr Asp Tyr Leu Met Tyr Ala Asp Ile Asp Tyr Asp His Pro Asp Val
            195                 200                 205

Val Ala Glu Ile Lys Arg Trp Gly Thr Trp Tyr Ala Asn Glu Leu Gln
            210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Pro Leu
                245                 250                 255

Phe Thr Val Gly Glu Tyr Trp Ser Tyr Asp Ile Asn Lys Leu His Asn
            260                 265                 270

Tyr Ile Thr Lys Thr Asn Gly Thr Met Ser Leu Phe Asp Ala Pro Leu
            275                 280                 285

His Asn Lys Phe Tyr Thr Ala Ser Lys Ser Gly Gly Ala Phe Asp Met
            290                 295                 300

Arg Thr Leu Met Thr Asn Thr Leu Met Lys Asp Gln Pro Thr Leu Ala
305                 310                 315                 320

Val Thr Phe Val Asp Asn His Asp Thr Glu Pro Gly Gln Ala Leu Gln
                325                 330                 335

Ser Trp Val Asp Pro Trp Phe Lys Pro Leu Ala Tyr Ala Phe Ile Leu
            340                 345                 350

Thr Arg Gln Glu Gly Tyr Pro Cys Val Phe Tyr Gly Asp Tyr Tyr Gly
            355                 360                 365

Ile Pro Gln Tyr Asn Ile Pro Ser Leu Lys Ser Lys Ile Asp Pro Leu
            370                 375                 380

Leu Ile Ala Arg Arg Asp Tyr Ala Tyr Gly Thr Gln His Asp Tyr Leu
385                 390                 395                 400

Asp His Ser Asp Ile Ile Gly Trp Thr Arg Glu Gly Val Thr Glu Lys
                405                 410                 415
```

```
Pro Gly Ser Gly Leu Ala Ala Leu Ile Thr Asp Pro Gly Gly Ser
            420                 425                 430

Lys Trp Met Tyr Val Gly Lys Gln His Ala Gly Lys Val Phe Tyr Asp
        435                 440                 445

Leu Thr Gly Asn Arg Ser Asp Thr Val Thr Ile Asn Ser Asp Gly Trp
    450                 455                 460

Gly Glu Phe Lys Val Asn Gly Ser Val Ser Val Trp Val Pro Arg
465                 470                 475                 480

Lys Thr Thr

<210> SEQ ID NO 15
<211> LENGTH: 483
<212> TYPE: PRT
<213> ORGANISM: Artificial
<220> FEATURE:
<223> OTHER INFORMATION: Hybrid comprising N-terminal portion of AmyL
      through position 254, and C-terminal portion from AmyS

<400> SEQUENCE: 15

Thr Asn Leu Asn Gly Thr Leu Met Gln Tyr Phe Glu Trp Tyr Thr Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu Tyr Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Asp Thr Glu Asn Gly Asn
            180                 185                 190

Tyr Asp Tyr Leu Met Tyr Ala Asp Ile Asp Tyr Asp His Pro Asp Val
        195                 200                 205

Val Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Pro Leu
                245                 250                 255

Phe Thr Val Gly Glu Tyr Trp Ser Tyr Asp Ile Asn Lys Leu His Asn
            260                 265                 270

Tyr Ile Thr Lys Thr Asn Gly Thr Met Ser Leu Phe Asp Ala Pro Leu
        275                 280                 285
```

```
His Asn Lys Phe Tyr Thr Ala Ser Lys Ser Gly Gly Ala Phe Asp Met
    290                 295                 300

Arg Thr Leu Met Thr Asn Thr Leu Met Lys Asp Gln Pro Thr Leu Ala
305                 310                 315                 320

Val Thr Phe Val Asp Asn His Asp Thr Glu Pro Gly Gln Ala Leu Gln
                325                 330                 335

Ser Trp Val Asp Pro Trp Phe Lys Pro Leu Ala Tyr Ala Phe Ile Leu
                340                 345                 350

Thr Arg Gln Glu Gly Tyr Pro Cys Val Phe Tyr Gly Asp Tyr Tyr Gly
            355                 360                 365

Ile Pro Gln Tyr Asn Ile Pro Ser Leu Lys Ser Lys Ile Asp Pro Leu
370                 375                 380

Leu Ile Ala Arg Arg Asp Tyr Ala Tyr Gly Thr Gln His Asp Tyr Leu
385                 390                 395                 400

Asp His Ser Asp Ile Ile Gly Trp Thr Arg Glu Gly Val Thr Glu Lys
                405                 410                 415

Pro Gly Ser Gly Leu Ala Ala Leu Ile Thr Asp Gly Pro Gly Gly Ser
                420                 425                 430

Lys Trp Met Tyr Val Gly Lys Gln His Ala Gly Lys Val Phe Tyr Asp
            435                 440                 445

Leu Thr Gly Asn Arg Ser Asp Thr Val Thr Ile Asn Ser Asp Gly Trp
450                 455                 460

Gly Glu Phe Lys Val Asn Gly Gly Ser Val Ser Val Trp Val Pro Arg
465                 470                 475                 480

Lys Thr Thr

<210> SEQ ID NO 16
<211> LENGTH: 483
<212> TYPE: PRT
<213> ORGANISM: Artificial
<220> FEATURE:
<223> OTHER INFORMATION: Hybrid comprising N-terminal portion of AmyL
      through position 259, and C-terminal portion from AmyS

<400> SEQUENCE: 16

Thr Asn Leu Asn Gly Thr Leu Met Gln Tyr Phe Glu Trp Tyr Thr Pro
1               5                   10                  15

Asn Asp Gly Gln His Trp Lys Arg Leu Gln Asn Asp Ser Ala Tyr Leu
                20                  25                  30

Ala Glu His Gly Ile Thr Ala Val Trp Ile Pro Pro Ala Tyr Lys Gly
            35                  40                  45

Thr Ser Gln Ala Asp Val Gly Tyr Gly Ala Tyr Asp Leu Tyr Asp Leu
        50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
                100                 105                 110

Glu Asp Val Thr Ala Val Glu Val Asp Pro Ala Asp Arg Asn Arg Val
            115                 120                 125

Ile Ser Gly Glu Tyr Leu Ile Lys Ala Trp Thr His Phe His Phe Pro
        130                 135                 140

Gly Arg Gly Ser Thr Tyr Ser Asp Phe Lys Trp His Trp Tyr His Phe
145                 150                 155                 160
```

```
Asp Gly Thr Asp Trp Asp Glu Ser Arg Lys Leu Asn Arg Ile Tyr Lys
            165                 170                 175
Phe Gln Gly Lys Ala Trp Asp Trp Glu Val Ser Ser Glu Asn Gly Asn
        180                 185                 190
Tyr Asp Tyr Leu Met Tyr Ala Asp Ile Asp Tyr Asp His Pro Asp Val
    195                 200                 205
Val Ala Glu Ile Lys Arg Trp Gly Thr Trp Tyr Ala Asn Glu Leu Gln
210                 215                 220
Leu Asp Gly Phe Arg Leu Asp Ala Val Lys His Ile Lys Phe Ser Phe
225                 230                 235                 240
Leu Arg Asp Trp Val Asn His Val Arg Glu Lys Thr Gly Lys Glu Met
                245                 250                 255
Phe Thr Val Gly Glu Tyr Trp Ser Tyr Asp Ile Asn Lys Leu His Asn
            260                 265                 270
Tyr Ile Thr Lys Thr Asn Gly Thr Met Ser Leu Phe Asp Ala Pro Leu
        275                 280                 285
His Asn Lys Phe Tyr Thr Ala Ser Lys Ser Gly Gly Ala Phe Asp Met
    290                 295                 300
Arg Thr Leu Met Thr Asn Thr Leu Met Lys Asp Gln Pro Thr Leu Ala
305                 310                 315                 320
Val Thr Phe Val Asp Asn His Asp Thr Glu Pro Gly Gln Ala Leu Gln
                325                 330                 335
Ser Trp Val Asp Pro Trp Phe Lys Pro Leu Ala Tyr Ala Phe Ile Leu
            340                 345                 350
Thr Arg Gln Glu Gly Tyr Pro Cys Val Phe Tyr Gly Asp Tyr Tyr Gly
        355                 360                 365
Ile Pro Gln Tyr Asn Ile Pro Ser Leu Lys Ser Lys Ile Asp Pro Leu
    370                 375                 380
Leu Ile Ala Arg Arg Asp Tyr Ala Tyr Gly Thr Gln His Asp Tyr Leu
385                 390                 395                 400
Asp His Ser Asp Ile Ile Gly Trp Thr Arg Glu Gly Val Thr Glu Lys
                405                 410                 415
Pro Gly Ser Gly Leu Ala Ala Leu Ile Thr Asp Gly Pro Gly Gly Ser
            420                 425                 430
Lys Trp Met Tyr Val Gly Lys Gln His Ala Gly Lys Val Phe Tyr Asp
        435                 440                 445
Leu Thr Gly Asn Arg Ser Asp Thr Val Thr Ile Asn Ser Asp Gly Trp
    450                 455                 460
Gly Glu Phe Lys Val Asn Gly Gly Ser Val Ser Val Trp Val Pro Arg
465                 470                 475                 480
Lys Thr Thr

<210> SEQ ID NO 17
<211> LENGTH: 483
<212> TYPE: PRT
<213> ORGANISM: Artificial
<220> FEATURE:
<223> OTHER INFORMATION: Hybrid comprising N-terminal portion of AmyL
      through position 259, and C-terminal portion from AmyS

<400> SEQUENCE: 17

Thr Asn Leu Asn Gly Thr Leu Met Gln Tyr Phe Glu Trp Tyr Thr Pro
1               5                   10                  15
Asn Asp Gly Gln His Trp Lys Arg Leu Gln Asn Asp Ser Ala Tyr Leu
            20                  25                  30
```

```
Ala Glu His Gly Ile Thr Ala Val Trp Ile Pro Pro Ala Tyr Lys Gly
         35                  40                  45

Thr Ser Gln Ala Asp Val Gly Tyr Gly Ala Tyr Asp Leu Tyr Asp Leu
 50                  55                  60

Gly Glu Phe His Gln Lys Gly Thr Val Arg Thr Lys Tyr Gly Thr Lys
65                   70                  75                  80

Gly Glu Leu Gln Ser Ala Ile Lys Ser Leu His Ser Arg Asp Ile Asn
                 85                  90                  95

Val Tyr Gly Asp Val Val Ile Asn His Lys Gly Ala Asp Ala Thr
                100                 105                 110

Glu Asp Val Thr Ala Val Glu Val Asp Pro Ala Asp Arg Asn Arg Val
             115                 120                 125

Ile Ser Gly Glu Tyr Leu Ile Lys Ala Trp Thr His Phe His Phe Pro
130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Asp Thr Glu Asn Gly Asn
            180                 185                 190

Tyr Asp Tyr Leu Met Tyr Ala Asp Ile Asp Tyr Asp His Pro Asp Val
        195                 200                 205

Val Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Gly Glu Tyr Trp Ser Tyr Asp Ile Asn Lys Leu His Asn
            260                 265                 270

Tyr Ile Thr Lys Thr Asn Gly Thr Met Ser Leu Phe Asp Ala Pro Leu
        275                 280                 285

His Asn Lys Phe Tyr Thr Ala Ser Lys Ser Gly Gly Ala Phe Asp Met
    290                 295                 300

Arg Thr Leu Met Thr Asn Thr Leu Met Lys Asp Gln Pro Thr Leu Ala
305                 310                 315                 320

Val Thr Phe Val Asp Asn His Asp Thr Glu Pro Gly Gln Ala Leu Gln
                325                 330                 335

Ser Trp Val Asp Pro Trp Phe Lys Pro Leu Ala Tyr Ala Phe Ile Leu
            340                 345                 350

Thr Arg Gln Glu Gly Tyr Pro Cys Val Phe Tyr Gly Asp Tyr Tyr Gly
        355                 360                 365

Ile Pro Gln Tyr Asn Ile Pro Ser Leu Lys Ser Lys Ile Asp Pro Leu
    370                 375                 380

Leu Ile Ala Arg Arg Asp Tyr Ala Tyr Gly Thr Gln His Asp Tyr Leu
385                 390                 395                 400

Asp His Ser Asp Ile Ile Gly Trp Thr Arg Glu Gly Val Thr Glu Lys
                405                 410                 415

Pro Gly Ser Gly Leu Ala Ala Leu Ile Thr Asp Gly Pro Gly Gly Ser
            420                 425                 430

Lys Trp Met Tyr Val Gly Lys Gln His Ala Gly Lys Val Phe Tyr Asp
        435                 440                 445

Leu Thr Gly Asn Arg Ser Asp Thr Val Thr Ile Asn Ser Asp Gly Trp
```

```
              450                 455                 460
Gly Glu Phe Lys Val Asn Gly Gly Ser Val Ser Val Trp Val Pro Arg
465                 470                 475                 480

Lys Thr Thr

<210> SEQ ID NO 18
<211> LENGTH: 1449
<212> TYPE: DNA
<213> ORGANISM: Bacillus licheniformis

<400> SEQUENCE: 18
acaaatctta atgggacgct gatgcagtat tttgaatggt acacgcccaa tgacggccaa      60
cattggaagc gtctgcaaaa cgactcggca tatttggctg aacacggtat tactgccgtc     120
tggattcccc cggcatataa gggaacgagc caagcggatg tgggctacgg tgcttacgac     180
ctttatgatt taggggagtt tcatcaaaaa gggacggttc ggacaaagta cggcacaaaa     240
ggagagctgc aatctgcgat caaaagtctt cattcccgcg acattaacgt ttacggggat     300
gtggtcatca accacaaagg cggcgctgat gcgaccgaag atgtaaccgc ggttgaagtc     360
gatcccgctg accgcaaccg cgtaatttcc ggagaatacc taattaaagc ctggacacat     420
tttcattttc cggggcgcgg cagcacatac agcgatttta aatggcattg gtaccatttt     480 gacgaaccg attgggacga gtcccgaaag ctgaaccgca tctataagtt tcaaggaaag     540
gcttgggatt gggaagtttc cagtgaaaac ggcaactatg attatttgat gtatgccgac     600
atcgattatg accatcctga tgtcgtagca gaaattaaga gatggggcac ttggtatgcc     660
aatgagctcc aattggacgg tttccgtctt gatgctgtca acacattaa attttctttt     720 ttgcgggatt gggttaatca tgtcagggaa aaaacgggga aggaaatgtt tacggtagct     780
gaatattggc agaatgactt gggcgcgctg aaaaactatt tgaacaaaac aaattttaat     840
cattcagtgt ttgacgtgcc gcttcattat cagttccatg ctgcatcgac acagggaggc     900
ggctatgata tgaggaaatt gctgaacggt acggtcgttt ccaagcatcc gttgaaatcg     960
gttacatttg tcgataacca tgatacacag ccgggggcagt cgcttgagtc gactgtccaa    1020
acatggttta agccgcttgc ttacgctttt attctcacaa gggaatctgg ataccctcag    1080
gttttctacg gggatatgta cgggacgaaa ggagactccc agcgcgaaat tcctgccttg    1140
aaacacaaaa ttgaaccgat cttaaaagcg agaaaacagt atgcgtacgg agcacagcat    1200
gattatttcg accaccatga cattgtcggc tggacaaggg aaggcgacag ctcggttgca    1260
aattcaggtt tggcggcatt aataacagac ggacccggtg gggcaaagcg aatgtatgtc    1320
ggccggcaaa acgccggtga gacatggcat gacattaccg gaaaccgttc ggagccggtt    1380
gtcatcaatt cggaaggctg gggagagttt cacgtaaacg gcgggtcggt ttcaatttat    1440
gttcaaaga                                                            1449

<210> SEQ ID NO 19
<211> LENGTH: 1458
<212> TYPE: DNA
<213> ORGANISM: Bacillus stearothermophilus

<400> SEQUENCE: 19
gccgcaccgt ttaacggtac catgatgcag tattttgaat ggtacttgcc ggatgatggc      60
acgttatgga ccaaagtggc caatgaagcc aacaacttat ccagccttgg catcaccgct     120
ctttggctgc cgcccgctta caaggaaca agccgcagcg acgtagggta cggagtatac     180
```

```
gacttgtatg acctcggcga attcaatcaa aaagggaccg tccgcacaaa atatggaaca    240
aaagctcaat atcttcaagc cattcaagcc gcccacgccg ctggaatgca agtgtacgcc    300
gatgtcgtgt tcgaccataa aggcggcgct gacggcacgg aatgggtgga cgccgtcgaa    360
gtcaatccgt ccgaccgcaa ccaagaaatc tcgggcacct atcaaatcca agcatggacg    420
aaatttgatt ttcccgggcg gggcaacacc tactccagct ttaagtggcg ctggtaccat    480
tttgacggcg ttgattggga cgaaagccga aaattaagcc gcatttacaa attcaggggc    540
atcggcaaag cgtgggattg ggaagtagac acagaaaacg gaaactatga ctacttaatg    600
tatgccgacc ttgatatgga tcatcccgaa gtcgtaccg agctgaaaaa ctgggggaaa    660
tggtatgtca acacaacgaa cattgatggg ttccggcttg atgccgtcaa gcatattaag    720
ttcagttttt ttcctgattg gttgtcgtat gtgcgttctc agactggcaa gccgctattt    780
accgtcgggg aatattggag ctatgacatc aacaagttgc acaattacat tacgaaaaca    840
aacggaacga tgtctttgtt tgatgccccg ttacacaaca aattttatac cgcttccaaa    900 tcaggggggcg catttgatat gcgcacgtta atgaccaata ctctcatgaa agatcaaccg    960
acattggccg tcaccttcgt tgataatcat gacaccgaac ccggccaagc gcttcagtca   1020
tgggtcgacc catggttcaa accgttggct tacgcccttta ttctaactcg gcaggaagga   1080
tacccgtgcg tcttttatgg tgactattat ggcattccac aatataacat tccttcgctg   1140
aaaagcaaaa tcgatccgct cctcatcgcg cgcagggatt atgcttacgg aacgcaacat   1200
gattatcttg atcactccga catcatcggg tggacaaggg aagggggtcac tgaaaaacca   1260 ggatccgggc tggccgcact gatcaccgat gggccgggag aagcaaatg gatgtacgtt   1320 ggcaaacaac acgctggaaa agtgttctat gaccttaccg caaccggag tgacaccgtc   1380 accatcaaca gtgatggatg gggggaattc aaagtcaatg gcggttcggt ttcggtttgg   1440
gttcctagaa aaacgacc                                                  1458
```

<210> SEQ ID NO 20
<211> LENGTH: 1539
<212> TYPE: DNA
<213> ORGANISM: Artificial
<220> FEATURE:
<223> OTHER INFORMATION: EBS2 Encoding precursor form of AmyS control

<400> SEQUENCE: 20

```
gccgcaccgt ttaacggtac catgatgcag tattttgaat ggtacttgcc ggatgatggc     60
acgttatgga ccaaagtggc caatgaagcc aacaacttat ccagccttgg catcaccgct    120
ctttggctgc cgcccgctta caaaggaaca agccgcagcg acgtagggta cggagtatac    180
gacttgtatg acctcggcga attcaatcaa aaagggaccg tccgcacaaa atatggaaca    240
aaagctcaat atcttcaagc cattcaagcc gcccacgccg ctggaatgca agtgtacgcc    300
gatgtcgtgt tcgaccataa aggcggcgct gacggcacgg aatgggtgga cgccgtcgaa    360
gtcaatccgt ccgaccgcaa ccaagaaatc tcgggcacct atcaaatcca agcatggacg    420
aaatttgatt ttcccgggcg gggcaacacc tactccagct ttaagtggcg ctggtaccat    480
tttgacggcg ttgactggga cgaaagccga aaattaagcc gcatttacaa attcatcggc    540
aaagcgtggg attgggaagt agacacagaa aacggaaact atgactactt aatgtatgcc    600
gaccttgata tggatcatcc cgaagtcgta accgagctga aaaactgggg gaaatggtat    660
gtcaacacaa cgaacattga tgggttccgg cttgatgccg tcaagcatat taagttcagt    720
ttttttcctg attggttgtc gtatgtgcgt tctcagactg gcaagccgct atttaccgtc    780
```

```
gggaatatt ggagctatga catcaacaag ttgcacaatt acattacgaa acaaacgga      840 acgatgtctt tgtttgatgc cccgttacac aacaaatttt ataccgcttc caaatcaggg    900
ggcgcatttg atatgcgcac gttaatgacc aatactctca tgaaagatca accgacattg    960
gccgtcacct tcgttgataa tcatgacacc gaacccggcc aagcgcttca gtcatgggtc   1020
gacccatggt tcaaaccgtt ggcttacgcc tttattctaa ctcggcagga aggatacccg   1080
tgcgtctttt atggtgacta ttatggcatt ccacaatata acattccttc gctgaaaagc   1140
aaaatcgatc cgctcctcat cgcgcgcagg gattatgctt acggaacgca acatgattat   1200
cttgatcact ccgacatcat cgggtggaca agggaagggg tcactgaaaa accaggatcc   1260
gggctggccg cactgatcac cgatgggccg ggaggaagca aatggatgta cgttggcaaa   1320
caacacgctg aaaagtgtt ctatgacctt accggcaacc ggagtgacac cgtcaccatc   1380
aacagtgatg gatgggggga attcaaagtc aatggcggtt cggtttcggt ttgggttcct   1440
agaaaaacga ccgtttctac catcgctcgg ccgatcacaa cccgaccgtg gactggtgaa   1500
ttcgtccgtt ggaccgaacc acggttggtg gcatggcct                          1539
```

<210> SEQ ID NO 21
<211> LENGTH: 1449
<212> TYPE: DNA
<213> ORGANISM: Artificial
<220> FEATURE:
<223> OTHER INFORMATION: sequence encoding 186 chimera

<400> SEQUENCE: 21

```
acaaatctta atgggacgct gatgcagtat tttgaatggt acacgcccaa tgacggccaa     60
cattggaagc gtctgcaaaa cgactcggca tatttggctg aacacggtat tactgccgtc    120
tggattcccc cggcatataa gggaacgagc caagcggatg tgggctacgg tgcttacgac    180
ctttatgatt taggggagtt tcatcaaaaa gggacggttc ggacaaagta cggcacaaaa    240
ggagagctgc aatctgcgat caaaagtctt cattcccgcg acattaacgt ttacggggat    300
gtggtcatca accacaaagg cggcgctgat gcgaccgaag atgtaaccgc ggttgaagtc    360
gatcccgctg accgcaaccg cgtaatttcc ggagaatacc taattaaagc ctggacacat    420
tttcattttc cggggcgcgg cagcacatac agcgatttta aatggcattg gtaccatttt    480 gacgaaccg attgggacga gtcccgaaag ctgaaccgca tctataagtt tcaaggaaag    540
gcttgggatt gggaagttga cacagaaaaac ggaaactatg actacttaat gtatgccgac    600
cttgatatgg atcatcccga gtcgtgacc gagctgaaaa actgggggaa atggtatgtc    660
aacacaacga acattgatgg gttccggctt gatgccgtca agcatattaa gttcagtttt    720
tttcctgatt ggttgtcgta tgtgcgttct cagactggca agccgctatt taccgtcggg    780
gaatattgga gctatgacat caacaagttg cacaattaca ttacgaaaac aaacggaacg    840
atgtctttgt tgatgcccc gttacacaac aaatttata ccgcttccaa tcaggggc    900 gcatttgata tgcgcacgtt aatgaccaat actctcatga aagatcaacc gacattggcc    960
gtcaccttcg ttgataatca tgacaccgag cccggccaag cgcttcagtc atgggtcgac   1020
ccatggttca aaccgttggc ttacgccttt attctaactc ggcaggaagg atacccgtgc   1080 gtctttatg gtgactatta tggcattcca caatataaca ttccttcgct gaaaagcaaa   1140
atcgatccgc tcctcatcgc gcgcagggat tatgcttacg gaacgcaaca tgattatctt   1200
gatcactccg acatcatcgg gtggacaagg gaagggtca ctgaaaaacc aggatccggg   1260
```

| | |
|---|---|
| ctggccgcac tgatcaccga tgggccggga ggaagcaaat ggatgtacgt tggcaaacaa | 1320 |
| cacgctggaa aagtgttcta tgaccttacc ggcaaccgga gtgacaccgt caccatcaac | 1380 |
| agtgatggat gggggaatt caaagtcaat ggcggttcgg tttcggtttg ggttcctaga | 1440 |
| aaaacgacc | 1449 |

```
<210> SEQ ID NO 22
<211> LENGTH: 1449
<212> TYPE: DNA
<213> ORGANISM: Artificial
<220> FEATURE:
<223> OTHER INFORMATION: sequence encoding 187 chimera

<400> SEQUENCE: 22
```

| | |
|---|---|
| acaaatctta atgggacgct gatgcagtat tttgaatggt acacgcccaa tgacggccaa | 60 |
| cattggaagc gtctgcaaaa cgactcggca tatttggctg aacacggtat tactgccgtc | 120 |
| tggattcccc cggcatataa gggaacgagc caagcggatg tgggctacgg tgcttacgac | 180 |
| ctttatgatt taggggagtt tcatcaaaaa gggacggttc ggacaaagta cggcacaaaa | 240 |
| ggagagctgc aatctgcgat caaaagtctt cattcccgcg acattaacgt ttacggggat | 300 |
| gtggtcatca accacaaagg cggcgctgat gcgaccgaag atgtaaccgc ggttgaagtc | 360 |
| gatcccgctg accgcaaccg cgtaatttcc ggagaatacc taattaaagc ctggacacat | 420 |
| tttcattttc cggggcgcgg cagcacatac agcgatttta aatggcattg gtaccatttt | 480 |
| gacggaaccg attgggacga gtcccgaaag ctgaaccgca tctataagtt tcaaggaaag | 540 |
| gcttgggatt gggaagtttc cacagaaaac ggaaactatg actacttaat gtatgccgac | 600 |
| cttgatatgg atcatcccga agtcgtgacc gagctgaaaa actgggggaa atggtatgtc | 660 |
| aacacaacga acattgatgg gttccggctt gatgccgtca agcatattaa gttcagtttt | 720 |
| tttcctgatt ggttgtcgta tgtgcgttct cagactggca agccgctatt taccgtcggg | 780 |
| gaatattgga gctatgacat caacaagttg cacaattaca ttacgaaaac aaacggaacg | 840 |
| atgtctttgt ttgatgcccc gttacacaac aaattttata ccgcttccaa atcaggggc | 900 |
| gcatttgata tgcgcacgtt aatgaccaat actctcatga agatcaacc gacattggcc | 960 |
| gtcaccttcg ttgataatca tgacaccgag cccggccaag cgcttcagtc atgggtcgac | 1020 |
| ccatggttca aaccgttggc ttacgccttt attctaactc ggcaggaagg ataccgtgc | 1080 |
| gtcttttatg gtgactatta tggcattcca caatataaca ttccttcgct gaaaagcaaa | 1140 |
| atcgatccgc tcctcatcgc gcgcaggat tatgcttacg aacgcaaca tgattatctt | 1200 |
| gatcactccg acatcatcgg gtggacaagg gaaggggtca ctgaaaaacc aggatccggg | 1260 |
| ctggccgcac tgatcaccga tgggccggga ggaagcaaat ggatgtacgt tggcaaacaa | 1320 |
| cacgctggaa aagtgttcta tgaccttacc ggcaaccgga gtgacaccgt caccatcaac | 1380 |
| agtgatggat gggggaatt caaagtcaat ggcggttcgg tttcggtttg ggttcctaga | 1440 |
| aaaacgacc | 1449 |

```
<210> SEQ ID NO 23
<211> LENGTH: 1449
<212> TYPE: DNA
<213> ORGANISM: Artificial
<220> FEATURE:
<223> OTHER INFORMATION: sequence encoding 200 chimera

<400> SEQUENCE: 23
```

| | |
|---|---|
| acaaatctta atgggacgct gatgcagtat tttgaatggt acacgcccaa tgacggccaa | 60 |

```
cattggaagc gtctgcaaaa cgactcggca tatttggctg aacacggtat tactgccgtc     120
tggattcccc cggcatataa gggaacgagc caagcggatg tgggctacgg tgcttacgac     180
ctttatgatt taggggagtt tcatcaaaaa gggacggttc ggacaaagta cggcacaaaa     240
ggagagctgc aatctgcgat caaaagtctt cattcccgcg acattaacgt ttacggggat     300
gtggtcatca accacaaagg cggcgctgat gcgaccgaag atgtaaccgc ggttgaagtc     360
gatcccgctg accgcaaccg cgtaatttcc ggagaatacc taattaaagc ctggacacat     420
tttcattttc cggggcgcgg cagcacatac agcgatttta aatggcattg gtaccatttt     480 gacgaaccg attgggacga gtcccgaaag ctgaaccgca tctataagtt tcaaggaaag     540
gcttgggatt gggaagtttc cagtgaaaac ggcaactatg attatttgat gtatgccgac     600
cttgatatgg atcatcccga agtcgtgacc gagctgaaaa actgggggaa atggtatgtc     660
aacacaacga acattgatgg gttccggctt gatgccgtca agcatattaa gttcagtttt     720
tttcctgatt ggttgtcgta tgtgcgttct cagactggca agccgctatt taccgtcggg     780
gaatattgga gctatgacat caacaagttg cacaattaca ttacgaaaac aaacggaacg     840
atgtctttgt ttgatgcccc gttacacaac aaatttttata ccgcttccaa atcaggggc     900 gcatttgata tgcgcacgtt aatgaccaat actctcatga agatcaacc gacattggcc     960 gtcaccttcg ttgataatca tgacaccgag cccggccaag cgcttcagtc atgggtcgac    1020
ccatggttca aaccgttggc ttacgccttt attctaactc ggcaggaagg ataccgtgc    1080 gtctttatg gtgactatta tggcattcca caatataaca ttccttcgct gaaaagcaaa    1140
atcgatccgc tcctcatcgc gcgcagggat tatgcttacg gaacgcaaca tgattatctt    1200
gatcactccg acatcatcgg gtggacaagg gaagggtca ctgaaaaacc aggatccggg    1260
ctggccgcac tgatcaccga tgggccggga ggaagcaaat ggatgtacgt tggcaaacaa    1320
cacgctggaa aagtgttcta tgaccttacc ggcaaccgga gtgacaccgt caccatcaac    1380
agtgatggat gggggaatt caaagtcaat ggcggttcgg tttcggtttg ggttcctaga    1440
aaaacgacc                                                            1449
```

<210> SEQ ID NO 24
<211> LENGTH: 1449
<212> TYPE: DNA
<213> ORGANISM: Artificial
<220> FEATURE:
<223> OTHER INFORMATION: sequence encoding 200SB chimera
<400> SEQUENCE: 24

```
acaaatctta atgggacgct gatgcagtat tttgaatggt acacgcccaa tgacggccaa      60
cattggaagc gtctgcaaaa cgactcggca tatttggctg aacacggtat tactgccgtc     120
tggattcccc cggcatataa gggaacgagc caagcggatg tgggctacgg tgcttacgac     180
ctttatgatt taggggagtt tcatcaaaaa gggacggttc ggacaaagta cggcacaaaa     240
ggagagctgc aatctgcgat caaaagtctt cattcccgcg acattaacgt ttacggggat     300
gtggtcatca accacaaagg cggcgctgat gcgaccgaag atgtaaccgc ggttgaagtc     360
gatcccgctg accgcaaccg cgtaatttcc ggagaatacc taattaaagc ctggacacat     420
tttcattttc cggggcgcgg cagcacatac agcgatttta aatggcattg gtaccatttt     480 gacgaaccg attgggacga gtcccgaaag ctgaaccgca tctataagtt tcaaggaaag     540
gcttgggatt gggaagttga cacagaaaac ggcaactatg attatttgat gtatgccgac     600
```

| | |
|---|---|
| cttgatatgg atcatcccga agtcgtgacc gagctgaaaa actgggggaa atggtatgtc | 660 |
| aacacaacga acattgatgg gttccggctt gatgccgtca agcatattaa gttcagtttt | 720 |
| tttcctgatt ggttgtcgta tgtgcgttct cagactggca agccgctatt taccgtcggg | 780 |
| gaatattgga gctatgacat caacaagttg cacaattaca ttacgaaaac aaacggaacg | 840 |
| atgtctttgt ttgatgcccc gttacacaac aaatttata ccgcttccaa atcaggggc | 900 |
| gcatttgata tgcgcacgtt aatgaccaat actctcatga agatcaacc gacattggcc | 960 |
| gtcaccttcg ttgataatca tgacaccgag cccggccaag cgcttcagtc atgggtcgac | 1020 |
| ccatggttca aaccgttggc ttacgccttt attctaactc ggcaggaagg ataccccgtgc | 1080 |
| gtctttatg gtgactatta tggcattcca caatataaca ttccttcgct gaaaagcaaa | 1140 |
| atcgatccgc tcctcatcgc gcgcagggat tatgcttacg gaacgcaaca tgattatctt | 1200 |
| gatcactccg acatcatcgg gtggacaagg gaagggtca ctgaaaaacc aggatccggg | 1260 |
| ctggccgcac tgatcaccga tgggccggga ggaagcaaat ggatgtacgt tggcaaacaa | 1320 |
| cacgctggaa aagtgttcta tgaccttacc ggcaaccgga gtgacaccgt caccatcaac | 1380 |
| agtgatggat gggggggaatt caaagtcaat ggcggttcgg tttcggtttg ggttcctaga | 1440 |
| aaaacgacc | 1449 |

<210> SEQ ID NO 25
<211> LENGTH: 1449
<212> TYPE: DNA
<213> ORGANISM: Artificial
<220> FEATURE:
<223> OTHER INFORMATION: sequence encoding 202 chimera

<400> SEQUENCE: 25

| | |
|---|---|
| acaaatctta atgggacgct gatgcagtat tttgaatggt acacgcccaa tgacggccaa | 60 |
| cattggaagc gtctgcaaaa cgactcggca tatttggctg aacacggtat tactgccgtc | 120 |
| tggattcccc cggcatataa gggaacgagc caagcggatg tgggctacgg tgcttacgac | 180 |
| ctttatgatt taggggagtt tcatcaaaaa gggacggttc ggacaaagta cggcacaaaa | 240 |
| ggagagctgc aatctgcgat caaaagtctt cattcccgcg acattaacgt ttacggggat | 300 |
| gtggtcatca accacaaagg cggcgctgat gcgaccgaag atgtaaccgc ggttgaagtc | 360 |
| gatcccgctg accgcaaccg cgtaatttcc ggagaatacc taattaaagc ctggacacat | 420 |
| tttcattttc cggggcgcgg cagcacatac agcgatttta aatggcattg gtaccatttt | 480 |
| gacgaaccg attgggacga gtcccgaaag ctgaaccgca tctataagtt tcaaggaaag | 540 |
| gcttgggatt gggaagtttc cagtgaaaac ggcaactatg attatttgat gtatgccgac | 600 |
| atcgatatgg atcatcccga agtcgtgacc gagctgaaaa actgggggaa atggtatgtc | 660 |
| aacacaacga acattgatgg gttccggctt gatgccgtca agcatattaa gttcagtttt | 720 |
| tttcctgatt ggttgtcgta tgtgcgttct cagactggca agccgctatt taccgtcggg | 780 |
| gaatattgga gctatgacat caacaagttg cacaattaca ttacgaaaac aaacggaacg | 840 |
| atgtctttgt ttgatgcccc gttacacaac aaatttata ccgcttccaa atcaggggc | 900 |
| gcatttgata tgcgcacgtt aatgaccaat actctcatga agatcaacc gacattggcc | 960 |
| gtcaccttcg ttgataatca tgacaccgag cccggccaag cgcttcagtc atgggtcgac | 1020 |
| ccatggttca aaccgttggc ttacgccttt attctaactc ggcaggaagg ataccccgtgc | 1080 |
| gtctttatg gtgactatta tggcattcca caatataaca ttccttcgct gaaaagcaaa | 1140 |
| atcgatccgc tcctcatcgc gcgcagggat tatgcttacg gaacgcaaca tgattatctt | 1200 |

```
gatcactccg acatcatcgg gtggacaagg gaaggggtca ctgaaaaacc aggatccggg    1260
ctggccgcac tgatcaccga tgggccggga ggaagcaaat ggatgtacgt tggcaaacaa    1320
cacgctggaa aagtgttcta tgaccttacc ggcaaccgga gtgacaccgt caccatcaac    1380
agtgatggat gggggaatt caaagtcaat ggcggttcgg tttcggtttg ggttcctaga     1440
aaaacgacc                                                             1449
```

<210> SEQ ID NO 26
<211> LENGTH: 1449
<212> TYPE: DNA
<213> ORGANISM: Artificial
<220> FEATURE:
<223> OTHER INFORMATION: sequence encoding 202SB chimera

<400> SEQUENCE: 26

```
acaaatctta atgggacgct gatgcagtat tttgaatggt acacgcccaa tgacggccaa      60
cattggaagc gtctgcaaaa cgactcggca tatttggctg aacacggtat tactgccgtc    120
tggattcccc cggcatataa gggaacgagc caagcggatg tgggctacgg tgcttacgac    180
ctttatgatt taggggagtt tcatcaaaaa gggacggttc ggacaaagta cggcacaaaa    240
ggagagctgc aatctgcgat caaaagtctt cattcccgcg acattaacgt ttacggggat    300
gtggtcatca accacaaagg cggcgctgat gcgaccgaag atgtaaccgc ggttgaagtc    360
gatcccgctg accgcaaccg cgtaatttcc ggagaatacc taattaaagc ctggacacat    420
tttcattttc cggggcgcgg cagcacatac agcgatttta aatggcattg gtaccatttt    480
gacggaaccg attgggacga gtcccgaaag ctgaaccgca tctataagtt tcaaggaaag    540
gcttgggatt gggaagttga cacagaaaac ggcaactatg attatttgat gtatgccgac    600
atcgatatgg atcatcccga agtcgtgacc gagctgaaaa actggggaa atggtatgtc     660 aacacaacga acattgatgg ttccggctt gatgccgtca agcatattaa gttcagtttt     720
tttcctgatt ggttgtcgta tgtgcgttct cagactggca agccgctatt taccgtcggg    780
gaatattgga gctatgacat caacaagttg cacaattaca ttacgaaaac aaacggaacg    840
atgtctttgt ttgatgcccc gttacacaac aaatttata ccgcttccaa atcagggggc      900
gcatttgata tgcgcacgtt aatgaccaat actctcatga agatcaacc gacattggcc      960 gtcaccttcg ttgataatca tgacaccgag cccggccaag cgcttcagtc atgggtcgac    1020
ccatggttca aaccgttggc ttacgccttt attctaactc ggcaggaagg atacccgtgc    1080
gtcttttatg gtgactatta tggcattcca caatataaca ttccttcgct gaaaagcaaa    1140
atcgatccgc tcctcatcgc gcgcagggat tatgcttacg aacgcaaca tgattatctt     1200 gatcactccg acatcatcgg gtggacaagg gaaggggtca ctgaaaaacc aggatccggg    1260
ctggccgcac tgatcaccga tgggccggga ggaagcaaat ggatgtacgt tggcaaacaa    1320
cacgctggaa aagtgttcta tgaccttacc ggcaaccgga gtgacaccgt caccatcaac    1380
agtgatggat gggggaatt caaagtcaat ggcggttcgg tttcggtttg ggttcctaga     1440
aaaacgacc                                                             1449
```

<210> SEQ ID NO 27
<211> LENGTH: 1449
<212> TYPE: DNA
<213> ORGANISM: Artificial
<220> FEATURE:
<223> OTHER INFORMATION: sequence encoding 228 chimera

<400> SEQUENCE: 27

```
acaaatctta atgggacgct gatgcagtat tttgaatggt acacgcccaa tgacggccaa    60
cattggaagc gtctgcaaaa cgactcggca tatttggctg aacacggtat tactgccgtc   120
tggattcccc cggcatataa gggaacgagc caagcggatg tgggctacgg tgcttacgac   180
ctttatgatt taggggagtt tcatcaaaaa gggacggttc ggacaaagta cggcacaaaa   240
ggagagctgc aatctgcgat caaaagtctt cattcccgcg acattaacgt ttacggggat   300
gtggtcatca accacaaagg cggcgctgat gcgaccgaag atgtaaccgc ggttgaagtc   360
gatcccgctg accgcaaccg cgtaatttcc ggagaatacc taattaaagc ctggacacat   420
tttcattttc cggggcgcgg cagcacatac agcgatttta aatggcattg gtaccatttt   480
gacggaaccg attgggacga gtcccgaaag ctgaaccgca tctataagtt tcaaggaaag   540
gcttgggatt gggaagtttc cagtgaaaac ggcaactatg attatttgat gtatgccgac   600
atcgattatg accatcctga tgtcgtagca gaaattaaga gatggggcac ttggtatgcc   660
aatgagctcc aattggacgg tttccggctt gatgccgtca agcatattaa gttcagtttt   720
tttcctgatt ggttgtcgta tgtgcgttct cagactggca agccgctatt taccgtcggg   780
gaatattgga gctatgacat caacaagttg cacaattaca ttacgaaaac aaacggaacg   840
atgtctttgt ttgatgcccc gttacacaac aaatttata ccgcttccaa atcaggggc    900
gcatttgata tgcgcacgtt aatgaccaat actctcatga agatcaacc gacattggcc   960
gtcaccttcg ttgataatca tgacaccgag cccggccaag cgcttcagtc atgggtcgac  1020
ccatggttca aaccgttggc ttacgccttt attctaactc ggcaggaagg atacccgtgc  1080
gtcttttatg gtgactatta tggcattcca caatataaca ttccttcgct gaaaagcaaa  1140
atcgatccgc tcctcatcgc gcgcaggat tatgcttacg aacgcaaca tgattatctt  1200
gatcactccg acatcatcgg gtggacaagg gaaggggtca ctgaaaaacc aggatccggg  1260
ctggccgcac tgatcaccga tgggccggga ggaagcaaat ggatgtacgt tggcaaacaa  1320
cacgctggaa aagtgttcta tgaccttacc ggcaaccgga gtgacaccgt caccatcaac  1380
agtgatggat gggggaatt caaagtcaat ggcggttcgg tttcggtttg ggttcctaga  1440
aaaacgacc                                                          1449
```

<210> SEQ ID NO 28
<211> LENGTH: 1449
<212> TYPE: DNA
<213> ORGANISM: Artificial
<220> FEATURE:
<223> OTHER INFORMATION: sequence encoding 228SB chimera

<400> SEQUENCE: 28

```
gcgaatctta atgggacgct gatgcagtat tttgaatggt acacgcccaa tgacggccaa    60
cattggaagc gtctgcaaaa cgactcggca tatttggctg aacacggtat tactgccgtc   120
tggattcccc cggcatataa gggaacgagc caagcggatg tgggctacgg tgcttacgac   180
ctttatgatt taggggagtt tcatcaaaaa gggacggttc ggacaaagta cggcacaaaa   240
ggagagctgc aatctgcgat caaaagtctt cattcccgcg acattaacgt ttacggggat   300
gtggtcatca accacaaagg cggcgctgat gcgaccgaag atgtaaccgc ggttgaagtc   360
gatcccgctg accgcaaccg cgtaatttcc ggagaatacc taattaaagc ctggacacat   420
tttcattttc cggggcgcgg cagcacatac agcgatttta aatggcattg gtaccatttt   480
gacggaaccg attgggacga gtcccgaaag ctgaaccgca tctataagtt tcaaggaaag   540
```

```
gcttgggatt gggaagttga cacagaaaac ggcaactatg attatttgat gtatgccgac    600
atcgattatg accatcctga tgtcgtagca gaaattaaga gatggggcac ttggtatgcc    660
aatgagctcc aattggacgg tttccggctt gatgccgtca agcatattaa gttcagtttt    720
tttcctgatt ggttgtcgta tgtgcgttct cagactggca agccgctatt taccgtcggg    780
gaatattgga gctatgacat caacaagttg cacaattaca ttacgaaaac aaacggaacg    840
atgtctttgt ttgatgcccc gttacacaac aaatttttata ccgcttccaa atcaggggc    900 gcatttgata tgcgcacgtt aatgaccaat actctcatga agatcaacc gacattggcc    960 gtcaccttcg ttgataatca tgacaccgag cccggccaag cgcttcagtc atgggtcgac   1020
ccatggttca aaccgttggc ttacgccttt attctaactc ggcaggaagg atacccgtgc   1080
gtcttttatg gtgactatta tggcattcca caatataaca ttccttcgct gaaaagcaaa   1140
atcgatccgc tcctcatcgc gcgcagggat tatgcttacg gaacgcaaca tgattatctt   1200
gatcactccg acatcatcgg gtggacaagg gaaggggtca ctgaaaaacc aggatccggg   1260
ctggccgcac tgatcaccga tgggccggga ggaagcaaat ggatgtacgt tggcaaacaa   1320
cacgctggaa aagtgttcta tgaccttacc ggcaaccgga gtgacaccgt caccatcaac   1380
agtgatggat gggggggaatt caaagtcaat ggcggttcgg tttcggtttg ggttcctaga   1440
aaaacgacc                                                            1449

<210> SEQ ID NO 29
<211> LENGTH: 1449
<212> TYPE: DNA
<213> ORGANISM: Artificial
<220> FEATURE:
<223> OTHER INFORMATION: sequence encoding 249 chimera

<400> SEQUENCE: 29
acaaatctta atgggacgct gatgcagtat tttgaatggt acacgcccaa tgacggccaa     60
cattggaagc gtctgcaaaa cgactcggca tatttggctg aacacggtat tactgccgtc    120
tggattcccc cggcatataa gggaacgagc caagcggatg tgggctacgg tgcttacgac    180
ctttatgatt tagggagtt tcatcaaaaa gggacggttc ggacaaagta cggcacaaaa    240
ggagagctgc aatctgcgat caaaagtctt cattcccgcg acattaacgt ttacggggat    300
gtggtcatca accacaaagg cggcgctgat gcgaccgaag atgtaaccgc ggttgaagtc    360
gatcccgctg accgcaaccg cgtaatttcc ggagaatacc taattaaagc ctggacacat    420
tttcattttc cggggcgcgg cagcacatac agcgattta aatggcattg gtaccattt    480 gacggaaccg attgggacga gtcccgaaag ctgaaccgca tctataagtt tcaaggaaag    540
gcttgggatt gggaagtttc cagtgaaaac ggcaactatg attatttgat gtatgccgac    600
atcgattatg accatcctga tgtcgtagca gaaattaaga gatggggcac ttggtatgcc    660
aatgagctcc aattggacgg tttccgtctt gatgctgtca aacacattaa attttctttt    720
ttgcgggatt gggttaatca tgtcaggtct cagactggca agccgctatt taccgtcggg    780
gaatattgga gctatgacat caacaagttg cacaattaca ttacgaaaac aaacggaacg    840
atgtctttgt ttgatgcccc gttacacaac aaatttttata ccgcttccaa atcaggggc    900 gcatttgata tgcgcacgtt aatgaccaat actctcatga agatcaacc gacattggcc    960 gtcaccttcg ttgataatca tgacaccgag cccggccaag cgcttcagtc atgggtcgac   1020
ccatggttca aaccgttggc ttacgccttt attctaactc ggcaggaagg atacccgtgc   1080
```

```
gtcttttatg gtgactatta tggcattcca caatataaca ttccttcgct gaaaagcaaa    1140
atcgatccgc tcctcatcgc gcgcagggat tatgcttacg gaacgcaaca tgattatctt    1200
gatcactccg acatcatcgg gtggacaagg aagggggtca ctgaaaaacc aggatccggg    1260
ctggccgcac tgatcaccga tgggccggga ggaagcaaat ggatgtacgt tggcaaacaa    1320
cacgctggaa aagtgttcta tgaccttacc ggcaaccgga gtgacaccgt caccatcaac    1380
agtgatggat gggggggaatt caaagtcaat ggcggttcgg tttcggtttg ggttcctaga    1440
aaaacgacc                                                            1449
```

<210> SEQ ID NO 30
<211> LENGTH: 1449
<212> TYPE: DNA
<213> ORGANISM: Artificial
<220> FEATURE:
<223> OTHER INFORMATION: sequence encoding 249SB chimera

<400> SEQUENCE: 30

```
acaaatctta atgggacgct gatgcagtat tttgaatggt acacgcccaa tgacggccaa      60
cattggaagc gtctgcaaaa cgactcggca tatttggctg aacacggtat tactgccgtc     120
tggattcccc cggcatataa gggaacgagc caagcggatg tgggctacgg tgcttacgac     180
ctttatgatt taggggagtt tcatcaaaaa gggacggttc ggacaaagta cggcacaaaa     240
ggagagctgc aatctgcgat caaaagtctt cattcccgcg acattaacgt ttacggggat     300
gtggtcatca accacaaagg cggcgctgat gcgaccgaag atgtaaccgc ggttgaagtc     360
gatcccgctg accgcaaccg cgtaatttcc ggagaatacc taattaaagc ctggacacat     420
tttcattttc cggggcgcgg cagcacatac agcgatttta atggcattg gtaccatttt     480 gacgaaaccg attgggacga gtcccgaaag ctgaaccgca tctataagtt tcaaggaaag     540
gcttgggatt gggaagttga cacagaaaac ggcaactatg attatttgat gtatgccgac     600
atcgattatg accatcctga tgtcgtagca gaaattaaga gatggggcac ttggtatgcc     660
aatgagctcc aattggacgg tttccgtctt gatgctgtca acacattaa attttctttt     720 ttgcgggatt gggttaatca tgtcaggtct cagactggca agccgctatt taccgtcggg     780
gaatattgga gctatgacat caacaagttg cacaattaca ttacgaaaac aaacggaacg     840
atgtctttgt ttgatgcccc gttacacaac aaatttata ccgcttccaa atcaggggc     900 gcatttgata tgcgcacgtt aatgaccaat actctcatga agatcaacc gacattggcc     960 gtcaccttcg ttgataatca tgacaccgag cccggccaag cgcttcagtc atgggtcgac    1020
ccatggttca aaccgttggc ttacgccttt attctaactc ggcaggaagg ataccgtgc    1080 gtcttttatg gtgactatta tggcattcca caatataaca ttccttcgct gaaaagcaaa    1140
atcgatccgc tcctcatcgc gcgcagggat tatgcttacg gaacgcaaca tgattatctt    1200
gatcactccg acatcatcgg gtggacaagg aagggggtca ctgaaaaacc aggatccggg    1260
ctggccgcac tgatcaccga tgggccggga ggaagcaaat ggatgtacgt tggcaaacaa    1320
cacgctggaa aagtgttcta tgaccttacc ggcaaccgga gtgacaccgt caccatcaac    1380
agtgatggat gggggggaatt caaagtcaat ggcggttcgg tttcggtttg ggttcctaga    1440
aaaacgacc                                                            1449
```

<210> SEQ ID NO 31
<211> LENGTH: 1449
<212> TYPE: DNA
<213> ORGANISM: Artificial
<220> FEATURE:
<223> OTHER INFORMATION: sequence encoding 254 chimera

<400> SEQUENCE: 31

| | | |
|---|---|---|
| acaaatctta atgggacgct gatgcagtat tttgaatggt acacgcccaa tgacggccaa | 60 |
| cattggaagc gtctgcaaaa cgactcggca tatttggctg aacacggtat tactgccgtc | 120 |
| tggattcccc cggcatataa gggaacgagc caagcggatg tgggctacgg tgcttacgac | 180 |
| ctttatgatt taggggagtt tcatcaaaaa gggacggttc ggacaaagta cggcacaaaa | 240 |
| ggagagctgc aatctgcgat caaaagtctt cattcccgcg acattaacgt ttacggggat | 300 |
| gtggtcatca accacaaagg cggcgctgat gcgaccgaag atgtaaccgc ggttgaagtc | 360 |
| gatcccgctg accgcaaccg cgtaatttcc ggagaatacc taattaaagc ctggacacat | 420 |
| tttcattttc cggggcgcgg cagcacatac agcgatttta aatggcattg gtaccatttt | 480 |
| gacggaaccg attgggacga gtcccgaaag ctgaaccgca tctataagtt tcaaggaaag | 540 |
| gcttgggatt gggaagtttc cagtgaaaac ggcaactatg attatttgat gtatgccgac | 600 |
| atcgattatg accatcctga tgtcgtagca gaaattaaga gatggggcac ttggtatgcc | 660 |
| aatgagctcc aattggacgg tttccgtctt gatgctgtca aacacattaa attttctttt | 720 |
| ttgcgggatt gggttaatca tgtcagggaa aaaacgggga agccgctatt taccgtcggg | 780 |
| gaatattgga gctatgacat caacaagttg cacaattaca ttacgaaaac aaacggaacg | 840 |
| atgtctttgt ttgatgcccc gttacacaac aaatttttata ccgcttccaa atcaggggga | 900 |
| gcatttgata tgcgcacgtt aatgaccaat actctcatga agatcaacc gacattggcc | 960 |
| gtcaccttcg ttgataatca tgacaccgag cccggccaag cgcttcagtc atgggtcgac | 1020 |
| ccatggttca aaccgttggc ttacgccttt attctaactc ggcaggaagg atacccgtgc | 1080 |
| gtcttttatg gtgactatta tggcattcca caatataaca ttccttcgct gaaaagcaaa | 1140 |
| atcgatccgc tcctcatcgc gcgcagggat tatgcttacg aacgcaaca tgattatctt | 1200 |
| gatcactccg acatcatcgg gtggacaagg gaaggggtca ctgaaaaacc aggatccggg | 1260 |
| ctggccgcac tgatcaccga tgggccggga ggaagcaaat ggatgtacgt tgcaaacaa | 1320 |
| cacgctggaa aagtgttcta tgaccttacc ggcaaccgga gtgacaccgt caccatcaac | 1380 |
| agtgatggat gggggaattt caaagtcaat ggcggttcgg tttcggtttg ggttcctaga | 1440 |
| aaaacgacc | 1449 |

<210> SEQ ID NO 32
<211> LENGTH: 1449
<212> TYPE: DNA
<213> ORGANISM: Artificial
<220> FEATURE:
<223> OTHER INFORMATION: sequence encoding 254SB chimera

<400> SEQUENCE: 32

| | | |
|---|---|---|
| acaaatctta atgggacgct gatgcagtat tttgaatggt acacgcccaa tgacggccaa | 60 |
| cattggaagc gtctgcaaaa cgactcggca tatttggctg aacacggtat tactgccgtc | 120 |
| tggattcccc cggcatataa gggaacgagc caagcggatg tgggctacgg tgcttacgac | 180 |
| ctttatgatt taggggagtt tcatcaaaaa gggacggttc ggacaaagta cggcacaaaa | 240 |
| ggagagctgc aatctgcgat caaaagtctt cattcccgcg acattaacgt ttacggggat | 300 |
| gtggtcatca accacaaagg cggcgctgat gcgaccgaag atgtaaccgc ggttgaagtc | 360 |
| gatcccgctg accgcaaccg cgtaatttcc ggagaatacc taattaaagc ctggacacat | 420 |

| | |
|---|---|
| tttcattttc cggggcgcgg cagcacatac agcgatttta aatggcattg gtaccatttt | 480 |
| gacggaaccg attgggacga gtcccgaaag ctgaaccgca tctataagtt tcaaggaaag | 540 |
| gcttgggatt gggaagttga cacagaaaac ggcaactatg attatttgat gtatgccgac | 600 |
| atcgattatg accatcctga tgtcgtagca gaaattaaga gatggggcac ttggtatgcc | 660 |
| aatgagctcc aattggacgg tttccgtctt gatgctgtca aacacattaa attttctttt | 720 |
| ttgcgggatt gggttaatca tgtcagggaa aaacgggga agccgctatt taccgtcggg | 780 |
| gaatattgga gctatgacat caacaagttg cacaattaca ttacgaaaac aaacggaacg | 840 |
| atgtctttgt ttgatgcccc gttacacaac aaatttttata ccgcttccaa atcaggggc | 900 |
| gcatttgata tgcgcacgtt aatgaccaat actctcatga aagatcaacc gacattggcc | 960 |
| gtcaccttcg ttgataatca tgacaccgag cccggccaag cgcttcagtc atgggtcgac | 1020 |
| ccatggttca aaccgttggc ttacgccttt attctaactc ggcaggaagg ataccgtgc | 1080 |
| gtctttatg gtgactatta tggcattcca caatataaca ttccttcgct gaaaagcaaa | 1140 |
| atcgatccgc tcctcatcgc gcgcagggat tatgcttacg gaacgcaaca tgattatctt | 1200 |
| gatcactccg acatcatcgg gtggacaagg aaggggtca ctgaaaaacc aggatccggg | 1260 |
| ctggccgcac tgatcaccga tgggccggga ggaagcaaat ggatgtacgt tggcaaacaa | 1320 |
| cacgctggaa aagtgttcta tgaccttacc ggcaaccgga gtgacaccgt caccatcaac | 1380 |
| agtgatggat gggggaatt caaagtcaat ggcggttcgg tttcggtttg ggttcctaga | 1440 |
| aaaacgacc | 1449 |

<210> SEQ ID NO 33
<211> LENGTH: 1449
<212> TYPE: DNA
<213> ORGANISM: Artificial
<220> FEATURE:
<223> OTHER INFORMATION: sequence encoding 259 chimera

<400> SEQUENCE: 33

| | |
|---|---|
| acaaatctta atgggacgct gatgcagtat tttgaatggt acacgcccaa tgacggccaa | 60 |
| cattggaagc gtctgcaaaa cgactcggca tatttggctg aacacggtat tactgccgtc | 120 |
| tggattcccc cggcatataa gggaacgagc caagcggatg tgggctacgg tgcttacgac | 180 |
| ctttatgatt taggggagtt tcatcaaaaa gggacggttc ggacaaagta cggcacaaaa | 240 |
| ggagagctgc aatctgcgat caaaagtctt cattcccgcg acattaacgt ttacggggat | 300 |
| gtggtcatca accacaaagg cggcgctgat gcgaccgaag atgtaaccgc ggttgaagtc | 360 |
| gatcccgctg accgcaaccg cgtaatttcc ggagaatacc taattaaagc ctggacacat | 420 |
| tttcattttc cggggcgcgg cagcacatac agcgatttta aatggcattg gtaccatttt | 480 |
| gacggaaccg attgggacga gtcccgaaag ctgaaccgca tctataagtt tcaaggaaag | 540 |
| gcttgggatt gggaagtttc cagtgaaaac ggcaactatg attatttgat gtatgccgac | 600 |
| atcgattatg accatcctga tgtcgtagca gaaattaaga gatggggcac ttggtatgcc | 660 |
| aatgagctcc aattggacgg tttccgtctt gatgctgtca aacacattaa attttctttt | 720 |
| ttgcgggatt gggttaatca tgtcagggaa aaacgggga aggaaatgtt tacgtaggg | 780 |
| gaatattgga gctatgacat caacaagttg cacaattaca ttacgaaaac aaacggaacg | 840 |
| atgtctttgt ttgatgcccc gttacacaac aaatttttata ccgcttccaa atcaggggc | 900 |
| gcatttgata tgcgcacgtt aatgaccaat actctcatga aagatcaacc gacattggcc | 960 |
| gtcaccttcg ttgataatca tgacaccgag cccggccaag cgcttcagtc atgggtcgac | 1020 |

```
ccatggttca aaccgttggc ttacgccttt attctaactc ggcaggaagg atacccgtgc    1080
gtcttttatg gtgactatta tggcattcca caatataaca ttccttcgct gaaaagcaaa    1140
atcgatccgc tcctcatcgc gcgcaggat tatgcttacg aacgcaaca tgattatctt      1200 gatcactccg acatcatcgg gtggacaagg aagggtca ctgaaaaacc aggatccggg      1260
ctggccgcac tgatcaccga tgggccggga ggaagcaaat ggatgtacgt tggcaaacaa    1320
cacgctggaa aagtgttcta tgaccttacc ggcaaccgga gtgacaccgt caccatcaac   1380
agtgatggat gggggaatt caaagtcaat ggcggttcgg tttcggtttg ggttcctaga     1440
aaaacgacc                                                            1449
```

<210> SEQ ID NO 34
<211> LENGTH: 1449
<212> TYPE: DNA
<213> ORGANISM: Artificial
<220> FEATURE:
<223> OTHER INFORMATION: sequence encoding 259SB chimera

<400> SEQUENCE: 34

```
acaaatctta atgggacgct gatgcagtat tttgaatggt acacgcccaa tgacggccaa     60
cattggaagc gtctgcaaaa cgactcggca tatttggctg aacacggtat tactgccgtc    120
tggattcccc cggcatataa gggaacgagc caagcggatg tgggctacgg tgcttacgac    180
ctttatgatt tagggagtt tcatcaaaaa gggacggttc ggacaaagta cggcacaaaa     240
ggagagctgc aatctgcgat caaaagtctt cattcccgcg acattaacgt ttacgggat    300 gtggtcatca accacaaagg cggcgctgat gcgaccgaag atgtaaccgc ggttgaagtc    360
gatcccgctg accgcaaccg cgtaatttcc ggagaatacc taattaaagc ctggacacat    420 tttcatttc cggggcgcgg cagcacatac agcgattta aatggcattg gtaccatttt      480
gacggaaccg attgggacga gtcccgaaag ctgaaccgca tctataagtt tcaaggaaag    540
gcttgggatt gggaagttga cacagaaaac ggcaactatg attatttgat gtatgccgac    600
atcgattatg accatcctga tgtcgtagca gaaattaaga gatgggggcac ttggtatgcc   660 aatgagctcc aattggacgg tttccgtctt gatgctgtca aacacattaa attttcttttt    720 ttgcgggatt gggttaatca tgtcaggaa aaacgggga aggaaatgtt tacggtaggg    780
gaatattgga gctatgacat caacaagttg acaattaca ttacgaaaac aaacggaacg   840
atgtctttgt tgatgcccc gttacacaac aaattttata ccgcttccaa tcagggggc    900 gcatttgata tgcgcacgtt aatgaccaat actctcatga agatcaacc gacattggcc   960 gtcaccttcg ttgataatca tgacaccgag cccggccaag cgcttcagtc atgggtcgac   1020
ccatggttca aaccgttggc ttacgccttt attctaactc ggcaggaagg atacccgtgc    1080
gtcttttatg gtgactatta tggcattcca caatataaca ttccttcgct gaaaagcaaa    1140
atcgatccgc tcctcatcgc gcgcaggat tatgcttacg aacgcaaca tgattatctt      1200 gatcactccg acatcatcgg gtggacaagg aagggtca ctgaaaaacc aggatccggg      1260
ctggccgcac tgatcaccga tgggccggga ggaagcaaat ggatgtacgt tggcaaacaa    1320
cacgctggaa aagtgttcta tgaccttacc ggcaaccgga gtgacaccgt caccatcaac   1380
agtgatggat gggggaatt caaagtcaat ggcggttcgg tttcggtttg ggttcctaga     1440
aaaacgacc                                                            1449
```

<210> SEQ ID NO 35

```
<211> LENGTH: 22
<212> TYPE: DNA
<213> ORGANISM: Artificial
<220> FEATURE:
<223> OTHER INFORMATION: primer Fred550-F

<400> SEQUENCE: 35
aaccgcggtt gaagtcgatc cc                                                  22

<210> SEQ ID NO 36
<211> LENGTH: 22
<212> TYPE: DNA
<213> ORGANISM: Artificial
<220> FEATURE:
<223> OTHER INFORMATION: primer Fred610-R

<400> SEQUENCE: 36
cccggaaaat gaaaatgtgt cc                                                  22

<210> SEQ ID NO 37
<211> LENGTH: 22
<212> TYPE: DNA
<213> ORGANISM: Artificial
<220> FEATURE:
<223> OTHER INFORMATION: primer Ethyl 1130-F

<400> SEQUENCE: 37
cgcacgttaa tgaccaatac tc                                                  22

<210> SEQ ID NO 38
<211> LENGTH: 22
<212> TYPE: DNA
<213> ORGANISM: Artificial
<220> FEATURE:
<223> OTHER INFORMATION: primer Ethyl 1190-R

<400> SEQUENCE: 38
gcttggccgg gctcggtgtc at                                                  22

<210> SEQ ID NO 39
<211> LENGTH: 40
<212> TYPE: DNA
<213> ORGANISM: Artificial
<220> FEATURE:
<223> OTHER INFORMATION: primer SS187DT-200etc fwd

<400> SEQUENCE: 39
gcttgggatt gggaagttga cacagaaaac ggcaactatg                               40

<210> SEQ ID NO 40
<211> LENGTH: 40
<212> TYPE: DNA
<213> ORGANISM: Artificial
<220> FEATURE:
<223> OTHER INFORMATION: primer SS187DT-200etc rev

<400> SEQUENCE: 40
catagttgcc gttttctgtg tcaacttccc aatcccaagc                               40
```